(12) United States Patent
Garneau-Tsodikova et al.

(10) Patent No.: US 11,851,391 B2
(45) Date of Patent: Dec. 26, 2023

(54) ANTIFUNGAL COMPOUNDS AND METHODS OF FORMING THE SAME

(71) Applicant: University of Kentucky Research Foundation, Lexington, KY (US)

(72) Inventors: Sylvie Garneau-Tsodikova, Lexington, KY (US); David S. Watt, Lexington, KY (US); Nishad Thamban Chandrika, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 765 days.

(21) Appl. No.: 16/514,276

(22) Filed: Jul. 17, 2019

(65) Prior Publication Data
US 2020/0024224 A1    Jan. 23, 2020

Related U.S. Application Data

(60) Provisional application No. 62/699,732, filed on Jul. 17, 2018.

(51) Int. Cl.
| | | |
|---|---|---|
| C07C 281/18 | (2006.01) | |
| C07C 243/10 | (2006.01) | |
| A61P 31/10 | (2006.01) | |
| C07C 277/00 | (2006.01) | |

(52) U.S. Cl.
CPC ............ *C07C 243/10* (2013.01); *A61P 31/10* (2018.01); *C07C 277/00* (2013.01)

(58) Field of Classification Search
CPC ..... A61P 31/10; C07C 243/10; C07C 251/86; C07C 277/00; C07C 281/18
USPC .......................................... 514/565; 524/565
See application file for complete search history.

(56) References Cited

FOREIGN PATENT DOCUMENTS

JP        1180111      *  3/1999

OTHER PUBLICATIONS

Enomoto, Kazuhiro (STN-ZCAPLUS, AN-1999:206869 ZCAPLUS, DNo. 130:273914 Jpn. Kokai Tokkyo Koho, 38 pp; JP 11080111 A19990326).*
English translation of JP1108111 (Year: 1999).*
Shrestha, S. K., Kril, L., Green, K. D., Kwiatkowski, S., Sviripa, V., Nickell, J., Dwoskin, L., Watt, D. S., & Garneau-Tsodikova, S . (2017). Bis(N-amidinohydrazones) and N-(amidino)-N'-aryl-bishydrazones: New classes of antibacterial/antifungal agents. Bioorg. Med. Chem., 25(1), 58-66.
Thamban Chandrika, N., Dennis, E. K., Shrestha, S. K., Ngo, H. X., Green, K. D., Kwiatkowski, S., Deaciuc, A. G., Dwoskin, L. P., Watt, D. S., & Garneau-Tsodikova, S . (2019). N,N'-Diaryl-bishydrazones in a biphenyl platform: Broad spectrum antifungal agents. Eur. J. Med. Chem., 164, 273-281.

* cited by examiner

*Primary Examiner* — San Ming R Hui
(74) *Attorney, Agent, or Firm* — Stites & Harbison PLLC; Mandy Wilson Decker

(57) ABSTRACT

An antifungal composition and a method of treating a systemic fungal infection are provided herein. The antifungal composition includes a diaryl bishydrazone. The method includes administering a therapeutically effective amount of the diaryl bishydrazone to a subject in need thereof.

8 Claims, 39 Drawing Sheets

1: R = H or Me; R' = C(=NH)NH₂
2: R = H or Me; R' = Ar

3: R = H or Me

7a,b: X = Ph (quant., 75%)
8a,b: X = o-NO₂Ph (49%, 68%)
9a-c: X = o-OMePh (63%, 69%, 58%)
10a,b: X = o-FPh (53%, 45%)
11a-c: X = m-OMePh (79%, 75%, 47%)
12a,b: X = m-FPh (48%, 66%)
13b: X = p-CNPh (67%)
14a: X = p-CF₃Ph (60%)
15a-c: X = p-OMePh (38%, 72%, 73%)
16b: X = p-O(i-Pr)Ph (18%)
17a-c: X = p-FPh (9%, 34%, 44%)
18a,b: X = p-ClPh (92%, 77%)
19a,b: X = p-BrPh (72%, 73%)
20a,b: X = o,p-diFPh (27%, 42%)
21a,b: X = o,m-diFPh (61%, 39%)
22a,b: X = m,m-diFPh (34%, 41%)
23b: X = t-Bu (63%)
24a-c: X = C(N=H)NH₂ (93%, 69%, 85%)

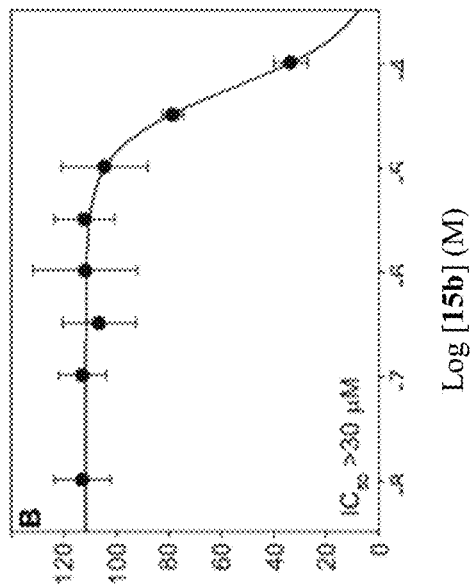
FIG. 6A
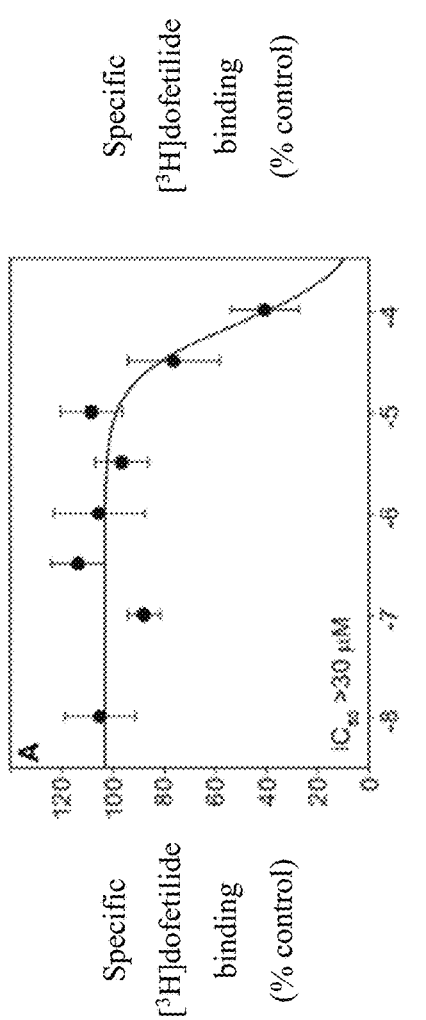
FIG. 6B
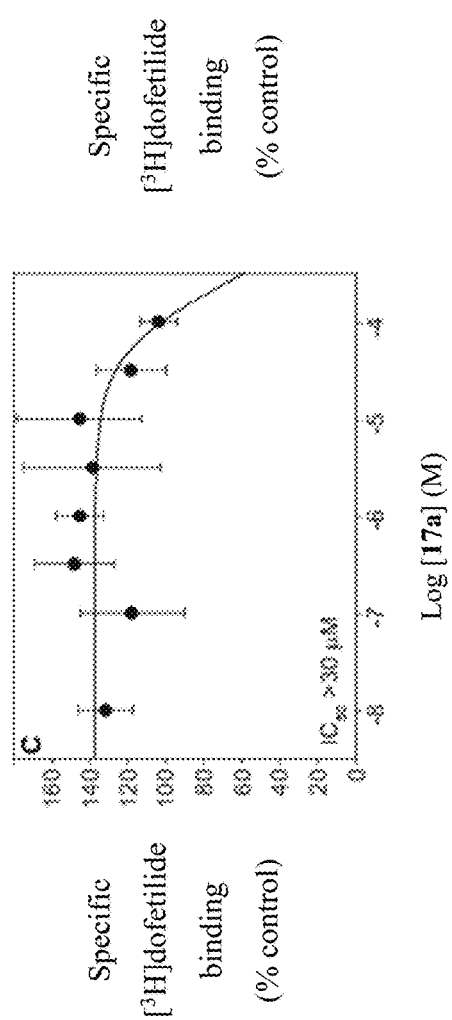
FIG. 6C
FIG. 6D

ANTIFUNGAL COMPOUNDS AND METHODS OF FORMING THE SAME

RELATED APPLICATIONS

This application claims the benefit of U.S. Provisional Application Ser. No. 62/699,732, filed Jul. 17, 2018, the entire disclosure of which is incorporated herein by this reference.

GOVERNMENT INTEREST

This invention was made with government support under grant numbers CA172379 and GM110787 awarded by the National Institute of Health (NIH), as well as grant number W81XWH-16-1-0635 awarded by the Department of Defense (DOD), Prostate Cancer Research Program. The Government has certain rights in the invention.

TECHNICAL FIELD

The present disclosure is directed to antifungal compounds and methods of forming the same. More specifically, the present disclosure is directed to antifungal hydrazone compounds and methods for making and using the same.

BACKGROUND

The growing practice of organ and hematopoietic cell transplantation and the increasing use of immunosuppressive, antiviral, and antineoplastic therapies has opened the door to adventitious systemic fungal infections. The high mortality rates for mycoses such as candidiasis and aspergillosis underscore the need for new antifungal therapies. However, the development of new systemic antifungal agents involves many challenges, in which a balance must be found between the scope and potency of any new agents versus the need for acceptable pharmacokinetic, pharmacodynamic, and toxicology profiles consistent with modern medicines. Compounding these challenges are the proclivity of opportunistic and dimorphic fungi to develop resistance and the growing concerns about the financial burden associated with the use of new antifungal drugs.

Accordingly, a continuing need exists for the development of specific antifungal agents for the treatment and prevention of fungal diseases and infections.

SUMMARY

The presently-disclosed subject matter meets the above-identified needs, as will become evident to those of ordinary skill in the art after a study of information provided in this document. Advantages of the present disclosure include antifungal agents and pharmaceutical compositions including same for the treatment or prevention of a fungal condition in a subject in need thereof.

This summary describes several embodiments of the presently-disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this summary or not. To avoid excessive repetition, this summary does not list or suggest all possible combinations of such features.

Provided herein, in some embodiments, is an antifungal composition comprising a compound according to Formula (I):

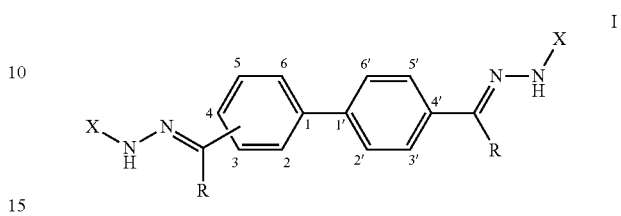

or a pharmaceutically acceptable salt thereof; wherein each R is independently selected from the group consisting of H and a lower alkyl; and each X is independently selected from the group consisting of phenyl, a substituted phenyl, an aromatic heterocycle, and a substituted aromatic heterocycle.

In some embodiments the lower alkyl of R is methyl. In some embodiments, the aromatic heterocycle or the substituted aromatic heterocycle comprises one or more heteroatoms selected from the group consisting nitrogen, oxygen, sulfur, and combinations thereof. In some embodiments, the substituted phenyl or substituted aromatic heterocycle comprises a substitution including nitro, an alkyl, an alkoxy, a halogen, cyano, a carboxylic acid or its derivatives, a sulfonic acid or its derivatives, aryl sulfoxides, aryl sulfones, a trihalomethyl, and combinations thereof. In one embodiment, the derivatives of carboxylic acid include esters or amides. In one embodiment, the derivatives of sulfonic acid include sulfonamides. In one embodiment, the aryl sulfoxides include $S(=O)C_6H_4Z$. In one embodiment, the aryl sulfones include $S(=O)_2C_6H_4Z$. In another embodiment, Z includes an alkyl, alkoxy, and/or halogen.

In some embodiments, the substituent of the first ring according to Formula I is in the 3 position. In some embodiments, the substituent of the first ring according to Formula I is in the 4 position. In one embodiment, the R in the substituent of the first ring is methyl. In some embodiments, at least one X is a substituted phenyl. In one embodiment, the substituted phenyl includes more than one substitution. In another embodiment, the substituted phenyl is disubstituted. In a further embodiment, the disubstituted phenyl is halogen substituted. In a further embodiment, the disubstituted phenyl is difluorophenyl.

Also provided herein, in some embodiments, is a method of treating a systemic fungal infection, the method comprising administering to a subject in need thereof a therapeutically effective amount of a compound according to Formula (I):

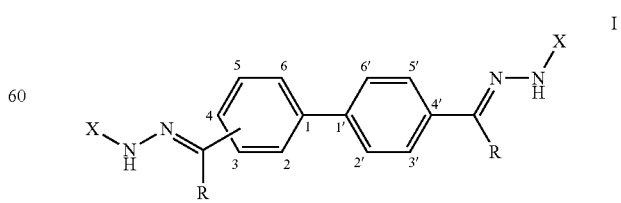

or a pharmaceutically acceptable salt thereof; wherein each R is independently selected from the group consisting of H and a lower alkyl; and each X is independently selected from the group consisting of phenyl, a substituted phenyl, an aromatic heterocycle, and a substituted aromatic heterocycle. In some embodiments, the systemic fungal condition is a fungal disease or a fungal infection. In some embodiments, at least one X is a substituted phenyl. In some embodiments, both X are substituted phenyl.

Additional advantages of the present invention will become apparent to those skilled in this art from the following detailed description, wherein only the preferred embodiment of the invention is shown and described, simply by way of illustration of the best mode contemplated of carrying out the invention. As will be realized, the invention is capable of other and different embodiments, and its several details are capable of modifications in various obvious respects, all without departing from the invention. Accordingly, the drawings and description are to be regarded as illustrative in nature, and not as restrictive.

BRIEF DESCRIPTION OF THE DRAWINGS

FIGS. 6A-F show graphs illustrating $IC_{50}$ curves for hERG interaction by compounds (A) 15a, (B) 15b, (C) 17a, (D) 17c, (E) 24a, and (F) amitriptyline, which are presented as mean±SDEV.

DETAILED DESCRIPTION OF THE DISCLOSURE

Figure 1:
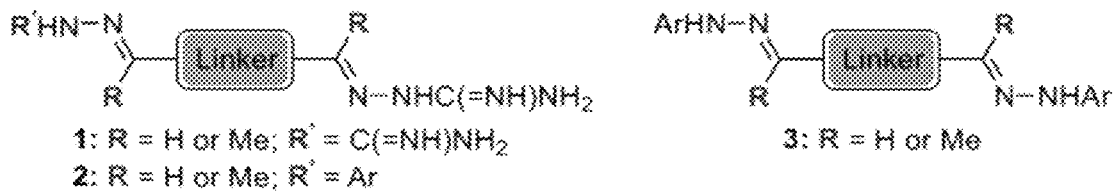
FIG. 1 shows representative structures for bishydrazones bearing N-amidino or N-aryl groups.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the terms used herein are believed to be well understood by those of ordinary skill in the art, certain definitions are set forth to facilitate explanation of the presently-disclosed subject matter.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, and in some embodiments±0.1% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or cannot occur, and that the description includes instances where said event or circumstance occurs and instances where it does not.

As used herein, the term "subject" can be a vertebrate, such as a mammal, a fish, a bird, a reptile, or an amphibian. Thus, the subject of the herein disclosed methods can be a human, non-human primate, domesticated animal (e.g., cat, dog, etc.), livestock (e.g., cattle, horses, pigs, sheep, goats, etc.), or laboratory animals (e.g., mouse, rabbit, rat, guinea pig, fruit fly, etc.). The term does not denote a particular age or sex. Thus, adult and newborn subjects, as well as fetuses, whether male or female, are intended to be covered.

A patient refers to a subject afflicted with a disease or disorder. The term "patient" includes human and veterinary subjects. In some aspects of the disclosed methods, the subject has been diagnosed with a need for treatment of one or more disorders, such as, but not limited to, a fungal infection or disease associated with a fungus.

The term "treat" and "treatment" refer to both therapeutic treatment and prophylactic or preventative measures, wherein the object is to prevent or slow down (lessen) an undesired pathological change or disorder, such as the development or spread of fungi. For purpose of this disclosure, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a specific condition.

As used herein, the phrase "identified to be in need of treatment for a disorder," or the like, refers to selection of a subject based upon need for treatment of the disorder. For example, a subject can be identified as having a need for treatment of a disorder (e.g., a disorder related to a fungal infection) based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target protein(s), or other biological entity together in such a manner that the compound can affect the activity of the target, either directly; e.g., by interacting with the target protein(s) itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition.

As used herein, the term a "therapeutically effective amount" refers to an amount that is sufficient to achieve the desired therapeutic result or to have an effect on undesired symptoms, but is generally insufficient to cause adverse side effects. For example, the phrase "therapeutically effective amount" means an amount of a compound of the present disclosure that (1) treats or prevents the particular disease, condition, or disorder; (2) attenuates, ameliorates, or eliminates one or more symptoms of the particular disease, condition, or disorder; or (3) prevents or delays the onset of one or more symptoms of the particular disease, condition, or disorder described herein. In the case of fungal infection, the therapeutically effective amount of the drug may be to inhibit the growth and/or reproduction of fungal cells and/or decrease the number of fungi and/or relieve to some extent one or more of the symptoms associated with a fungal condition such as a fungal disease or infection in a subject.

The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components.

Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14$^{th}$ edition), the Physicians' Desk Reference (64$^{th}$ edition), and The Pharmacological Basis of Therapeutics (12$^{th}$ edition), and they include, without limitation, medicaments; vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiasthmatic agents, anticonvulsants, antihistamines, antinauseants, antineoplastics, antipruritics, antipyretics; antispasmodics, cardiovascular preparations (including calcium channel blockers, beta-blockers, beta-agonists and antiarrythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mineral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "IC$_{50}$" is intended to refer to the concentration of a substance (e.g., a compound or a drug) that is required for 50% inhibition of a biological process, or component of a process, including a protein, subunit, organelle, ribonucleoprotein, etc. For example, IC$_{50}$ refers to the half maximal (50%) inhibitory concentration (IC) of a substance as determined in a suitable assay. For example, an IC$_{50}$ for inhibiting DCN1-UBC12 interaction can be determined in an in vitro assay system.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable mediajust prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. For example, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "R" is used herein as a generic symbol to represent various specific substituents. This symbol can be any substituent, not limited to those disclosed herein, and when it is defined to be certain substituents in one instance, it can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkenyl.

The term "alkyl" as used herein is a branched or unbranched saturated hydrocarbon group of 1 to 24 carbon atoms, such as methyl, ethyl, propyl, isopropyl, butyl, isobutyl, s-butyl, t-butyl, pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group is acyclic. The alkyl group can be branched or unbranched. The alkyl group can also be substituted or unsubstituted. A "lower alkyl" group is an alkyl group containing from one to six (e.g., from one to four) carbon atoms. Throughout the specification "alkyl" is generally used to refer to both unsubstituted alkyl groups and substituted alkyl groups; however, substituted alkyl groups are also specifically referred to herein by identifying the specific substituent(s) on the alkyl group. When "alkyl" is used in one instance and a specific term is used in another, it is not meant to imply that the term "alkyl" does not also refer to the specific term. This practice is also used for other groups described herein.

The term "amide" as used herein is represented by the formula —$C(O)N(R^1)(R^2)$, where each of $R^1$ and $R^2$ independently includes H or hydrocarbyl, or $R^1$ and $R^2$ are taken together with the N atom to which they are attached to complete a heterocycle having from 4 to 8 atoms in the ring structure The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The terms "alkoxy" and "alkoxyl" as used herein to refer to an alkyl or cycloalkyl group bonded through an ether linkage; that is, an "alkoxy" group can be defined as —$OR^1$ where $R^1$ is alkyl or cycloalkyl as defined above. "Alkoxy" also includes polymers of alkoxy groups as just described; that is, an alkoxy can be a polyether such as —$OR^1$—$OR^2$ or —OR $(OR^2)_a$—$OR^3$, where "a" is an integer of from 1 to 200 and $R^1$, $R^2$, and $R^3$ are alkyl and/or cycloalkyl groups.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd, Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, phenyl, naphthalene, biphenyl, anthracene, other polycyclic variants, and the like. The aryl group can be substituted or unsubstituted. The term "substituted aryl" or "substituted aryl group," as used herein, refers to an aryl group where one or more hydrogen atoms has been replaced by an electron-withdrawing or electron-donating group. Unless stated otherwise, use of the term "aryl" or "aryl group" is intended to include "substituted aryl" or "substituted aryl group" throughout the instant disclosure.

The term "biaryl" is a specific type of aryl group and is included in the definition of "aryl." Biaryl refers to two aryl groups that are bound together via a fused ring structure, as in naphthalene, or are attached via one or more carbon-carbon bonds, as in biphenyl.

The term "carboxylic acid" as used herein is represented by the formula —C(O)OH.

The term "cyano" as used herein is represented by the formula —CN.

The term "ester" as used herein is represented by the formula —OC(O)R¹ or —C(O)OR¹, where R¹ can be alkyl, cycloalkyl, alkenyl, cycloalkenyl, alkynyl, cycloalkynyl, aryl, or heteroaryl group as described herein.

The terms "halo," "halogen," or "halide," as used herein can be used interchangeably and refer to F, Cl, Br, or I.

The term "heteroaryl," as used herein refers to an aromatic group that has at least one heteroatom incorporated within the ring of the aromatic group. Examples of heteroatoms include, but are not limited to, nitrogen, oxygen, sulfur, and phosphorus, where N-oxides, sulfur oxides, and dioxides are permissible heteroatom substitutions. Heteroaryl groups can be monocyclic, or alternatively fused ring systems. Heteroaryl groups include, but are not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, pyrazolopyrimidinyl, 1,2-oxazol-4-yl, 1,2-oxazol-5-yl, 1,3-oxazolyl, 1,2,4-oxadiazol-5-yl, 1,2,3-triazolyl, 1,3-thiazol-4-yl, pyridinyl, and pyrimidin-5-yl.

The terms "heterocycle" or "heterocyclyl," as used herein can be used interchangeably and refer to single and multicyclic aromatic or non-aromatic ring systems in which at least one of the ring members is other than carbon. Thus, the term is inclusive of, but not limited to, "heterocycloalkyl," "heteroaryl," "bicyclic heterocycle," and "polycyclic heterocycle." Heterocycle includes pyridine, pyrimidine, furan, thiophene, pyrrole, isoxazole, isothiazole, pyrazole, oxazole, thiazole, imidazole, oxazole, including, 1,2,3-oxadiazole, 1,2,5-oxadiazole and 1,3,4-oxadiazole, thiadiazole, including, 1,2,3-thiadiazole, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridine, pyridazine, pyrimidine, pyrazine, triazine, including 1,2,4-triazine and 1,3,5-triazine, tetrazine, including 1,2,4,5-tetrazine, pyrrolidine, piperidine, piperazine, morpholine, azetidine, tetrahydropyran, tetrahydrofuran, dioxane, and the like. The heterocycle group can be substituted or unsubstituted.

The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus.

The term "nitro" as used herein is represented by the formula —NO₂.

The term "sulfonic acid" as used herein is represented by the formula —SO₃H.

The term "sulfonamide" as used herein is represented by the formula —S(O)₂N(R¹)(R²), where each of R¹ and R² independently includes H or hydrocarbyl, or R¹ and R² are taken together with the N atom to which they are attached to complete a heterocycle having from 4 to 8 atoms in the ring structure.

The presently-disclosed subject matter includes antifungal compounds having antifungal activity and pharmaceutical compositions including such compounds together with a pharmaceutically acceptable carrier. The antifungal compounds of the present disclosure are useful as antifungal agents and can inhibit the growth and reproduction of fungal cells and/or decrease the number of fungi. Accordingly, the antifungal compounds of the present disclosure can be used to treat or prevent a systemic fungal condition, e.g., a fungal disease or infection, in a subject in need thereof. Subject as used herein refer to mammals and in particular to humans and domestic animals.

In some embodiments, the antifungal compounds include hydrazone compounds. In some embodiments, the hydrazone compounds include diaryl bishydrazones, such as, but not limited to, those according to Formula I:

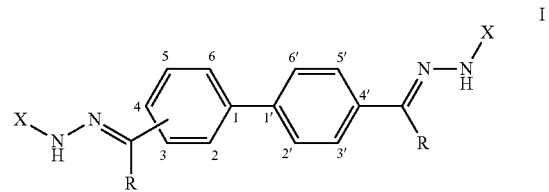

or a pharmaceutically acceptable salt thereof, where each R independently includes H or a lower alkyl, e.g., a $C_{1-6}$ alkyl such as a methyl or ethyl group; and each X independently includes phenyl, a substituted phenyl, an aromatic heterocycle, or a substituted aromatic heterocycle. The aromatic heterocycle and/or substituted aromatic heterocycle may include any suitable heteroatom, such as, but not limited to, nitrogen (e.g., pyridyl), oxygen (e.g., pyranyl), or sulfur. Additionally or alternatively, the aromatic heterocycle and/or substituted aromatic heterocycle may include multiple heteroatoms, with each heteroatom being the same (e.g., pyridizinyl) or different (e.g., oxazinyl).

In one embodiment, the substitution on the substituted phenyl or substituted aromatic heterocycle includes, but is not limited to, nitro, an alkyl (e.g., methyl, ethyl, propyl, etc.), an alkoxy (e.g., methoxy, isopropoxy), a halogen (fluoro, chloro, bromo), cyano, carboxylic acid or its derivatives (e.g., esters or amides), sulfonic acid or its derivatives (e.g., sulfonamides), aryl sulfoxides (e.g., S(=O)C₆H₄Z, where Z is alkyl (e.g., methyl, ethyl, propyl), an alkoxy (e.g., methoxy, isopropoxy), or a halogen (e.g., fluoro, chloro, bromo)), aryl sulfones (e.g., S(=O)₂C₆H₄Z, where Z is alkyl (e.g., methyl, ethyl, propyl), an alkoxy (e.g., methoxy, isopropoxy), or a halogen (e.g., fluoro, chloro, bromo)), or a trihalomethyl (e.g., trifluoromethyl). In another embodiment, the substitution on the substituted phenyl or substituted aromatic heterocycle is in the ortho, meta, or para position. In a further embodiment, the substituted phenyl and/or substituted aromatic heterocycle includes more than one substitution (e.g., disubstituted, trisubstituted), with the substitutions being in the same position (i.e., ortho, ortho; meta, meta) or in different positions (i.e., ortho, meta; ortho, para; meta, para). For example, the substituted phenyl may include difluorophenyl, with the fluoro groups in the ortho, para; ortho, meta; ortho, ortho; meta, para; or meta, meta position. The multi-substituted phenyl also need not include the same substitutions, such that each substitution may independently include any of the substitutions disclosed herein.

Suitable compounds according to Formula I include, but are not limited to, N,N'-Diaryl-bishydrazones of [1,1'-biphenyl]-3,4'-dicarboxaldehyde, [1,1'-biphenyl]-4,4'-dicarboxaldehyde, 4,4'-bisacetyl-1,1-biphenyl, and/or 4,4'-bisacetyl-1,1-biphenyl; 4,4'-bis((E)-1-(2-(4-fluorophenyl)hydrazono)ethyl)-1,1'-biphenyl; and/or combinations thereof. For example, suitable compounds according to Formula I include, but are not limited to:

| Compound Number | Structure | Substituents |
|---|---|---|
| 7a | 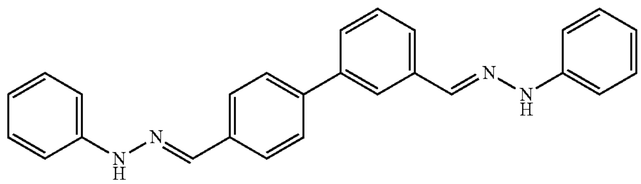 [SMILES: C(=N\Nc1ccccc1)/c1ccc(-c2cccc(/C=N/Nc3ccccc3)c2)cc1] | 3<br>X = Ph<br>R = H |
| 7b | 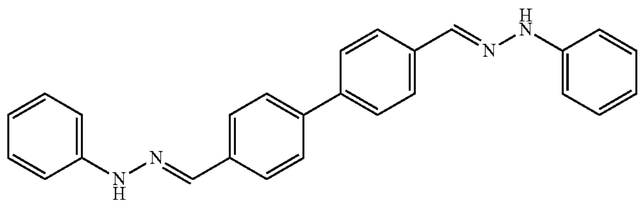 [SMILES: C(=N\Nc1ccccc1)/c1ccc(-c2ccc(/C=N/Nc3ccccc3)cc2)cc1] | 4<br>X = Ph<br>R = H |
| 8a | 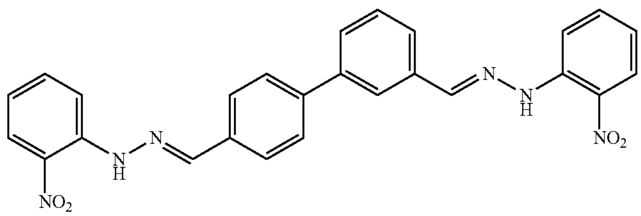 [SMILES: O=[N+]([O-])c1ccccc1N/N=C/c1ccc(-c2cccc(/C=N/Nc3ccccc3[N+](=O)[O-])c2)cc1] | 3<br>X = o-NO$_2$Ph<br>R = H |
| 8b | 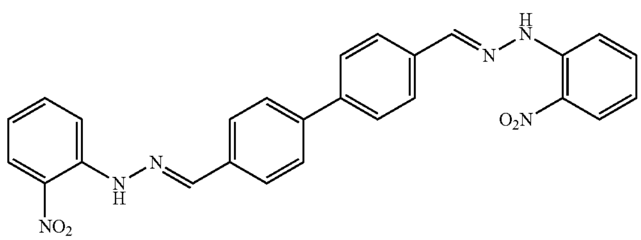 [SMILES: O=[N+]([O-])c1ccccc1N/N=C/c1ccc(-c2ccc(/C=N/Nc3ccccc3[N+](=O)[O-])cc2)cc1] | 4<br>X = o-NO$_2$Ph<br>R = H |
| 9a | 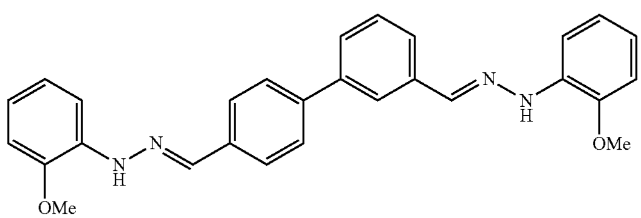 [SMILES: COc1ccccc1N/N=C/c1ccc(-c2cccc(/C=N/Nc3ccccc3OC)c2)cc1] | 3<br>X = o-OMePh<br>R = H |
| 9b | 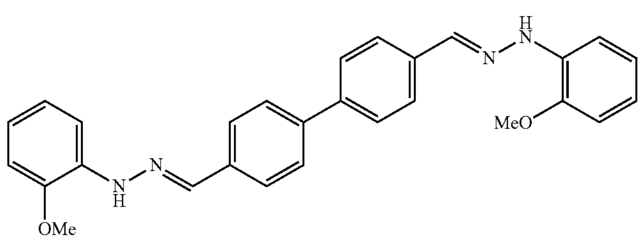 [SMILES: COc1ccccc1N/N=C/c1ccc(-c2ccc(/C=N/Nc3ccccc3OC)cc2)cc1] | 4<br>X = o-OMePh<br>R = H |
| 9c | 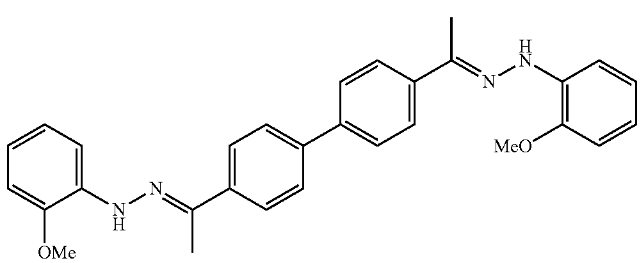 [SMILES: COc1ccccc1N/N=C(\C)c1ccc(-c2ccc(/C(C)=N/Nc3ccccc3OC)cc2)cc1] | 4<br>X = o-OMePh<br>R = Me |

-continued

| Compound Number | Structure | Substituents |
|---|---|---|
| 10a | 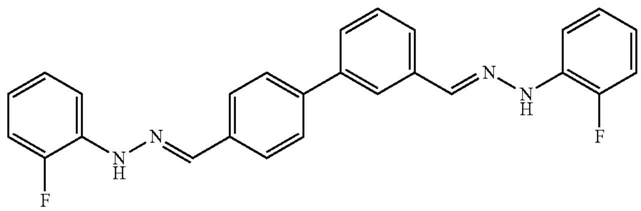 [SMILES: Fc1ccccc1N/N=C/c1ccc(-c2cccc(/C=N/Nc3ccccc3F)c2)cc1] | 3<br>X = o-FPh<br>R = H |
| 10b | 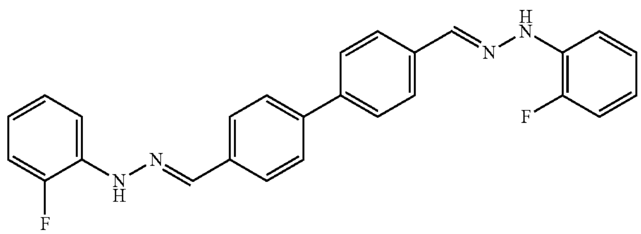 [SMILES: Fc1ccccc1N/N=C/c1ccc(-c2ccc(/C=N/Nc3ccccc3F)cc2)cc1] | 3<br>X = o-FPh<br>R = H |
| 11a | 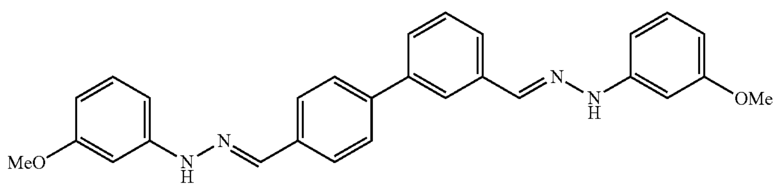 [SMILES: COc1cccc(N/N=C/c2ccc(-c3cccc(/C=N/Nc4cccc(OC)c4)c3)cc2)c1] | 3<br>X = m-OMePh<br>R = H |
| 11b | 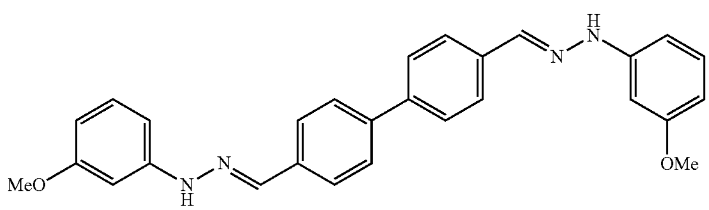 [SMILES: COc1cccc(N/N=C/c2ccc(-c3ccc(/C=N/Nc4cccc(OC)c4)cc3)cc2)c1] | 4<br>X = m-OMePh<br>R = H |
| 11c | 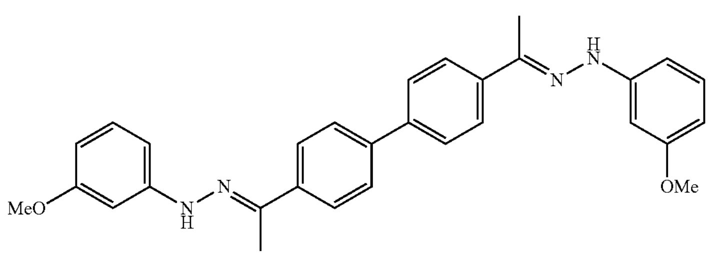 [SMILES: COc1cccc(N/N=C(\C)c2ccc(-c3ccc(/C(C)=N/Nc4cccc(OC)c4)cc3)cc2)c1] | 4<br>X = m-OMePh<br>R = Me |
| 12a | 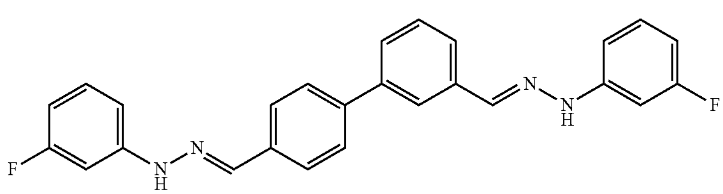 [SMILES: Fc1cccc(N/N=C/c2ccc(-c3cccc(/C=N/Nc4cccc(F)c4)c3)cc2)c1] | 3<br>X = m-FPh<br>R = H |
| 12b | 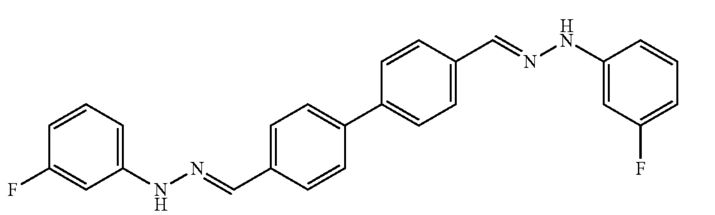 [SMILES: Fc1cccc(N/N=C/c2ccc(-c3ccc(/C=N/Nc4cccc(F)c4)cc3)cc2)c1] | 4<br>X = m-FPh<br>R = H |

-continued

| Compound Number | Structure | Substituents |
|---|---|---|
| 13b | 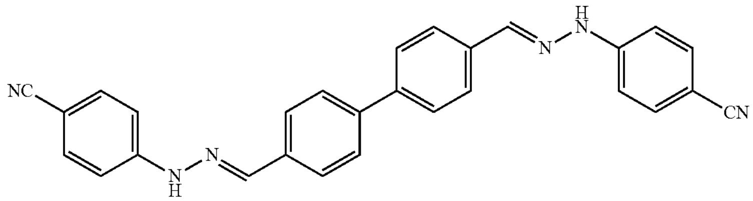 [SMILES: N#Cc1ccc(N/N=C/c2ccc(-c3ccc(/C=N/Nc4ccc(C#N)cc4)cc3)cc2)cc1] | 4<br>X = p-CNPh<br>R = H |
| 14a | 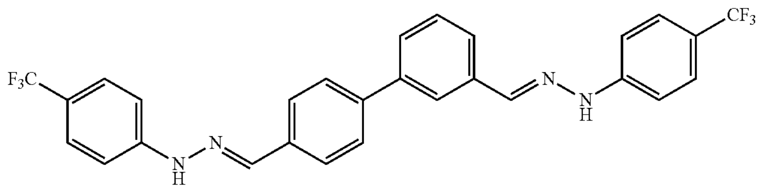 [SMILES: FC(F)(F)c1ccc(N/N=C/c2ccc(-c3cccc(/C=N/Nc4ccc(C(F)(F)F)cc4)c3)cc2)cc1] | 3<br>X = p-CF$_3$Ph<br>R = H |
| 15a | 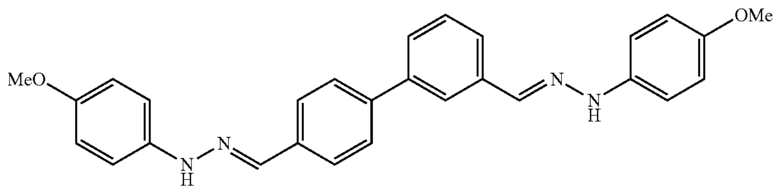 [SMILES: COc1ccc(N/N=C/c2ccc(-c3cccc(/C=N/Nc4ccc(OC)cc4)c3)cc2)cc1] | 3<br>X = p-OMePh<br>R = H |
| 15b | 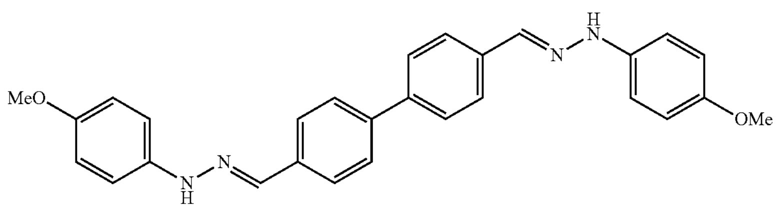 [SMILES: COc1ccc(N/N=C/c2ccc(-c3ccc(/C=N/Nc4ccc(OC)cc4)cc3)cc2)cc1] | 4<br>X = p-OMePh<br>R = H |
| 15c | 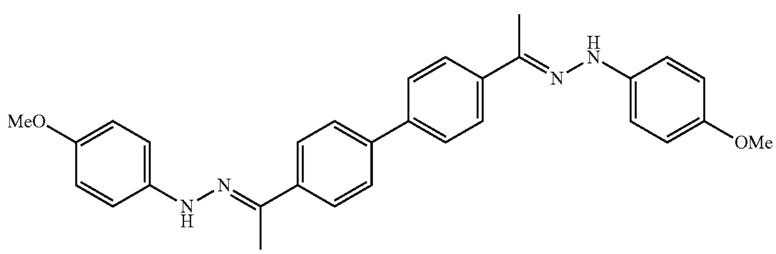 [SMILES: COc1ccc(N/N=C(\C)c2ccc(-c3ccc(/C(C)=N/Nc4ccc(OC)cc4)cc3)cc2)cc1] | 4<br>X = p-OMePh<br>R = Me |
| 16b | 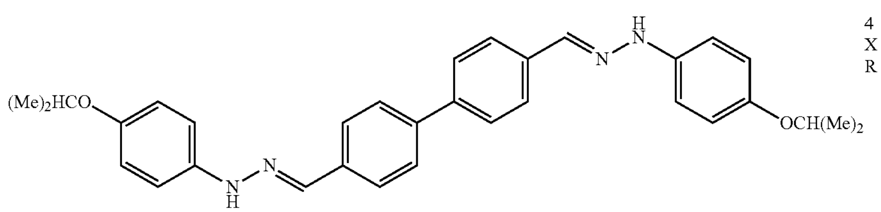 | 4<br>X = p-O(i-Pr)Ph<br>R = H |
| 17a | 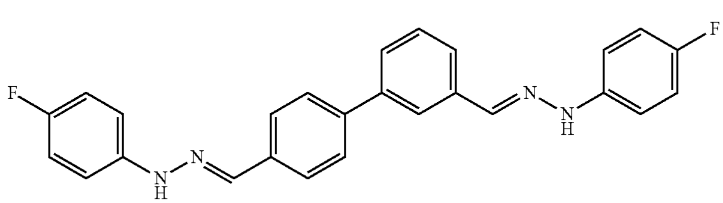 [SMILES: Fc1ccc(N/N=C/c2ccc(-c3cccc(/C=N/Nc4ccc(F)cc4)c3)cc2)cc1] | 3<br>X = p-FPh<br>R = H |

-continued

| Compound Number | Structure | Substituents |
|---|---|---|
| 17b | 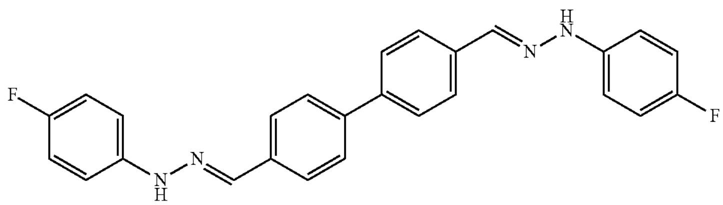 [SMILES: Fc1ccc(N/N=C/c2ccc(-c3ccc(/C=N/Nc4ccc(F)cc4)cc3)cc2)cc1] | 4<br>X = p-FPh<br>R = H |
| 17c | 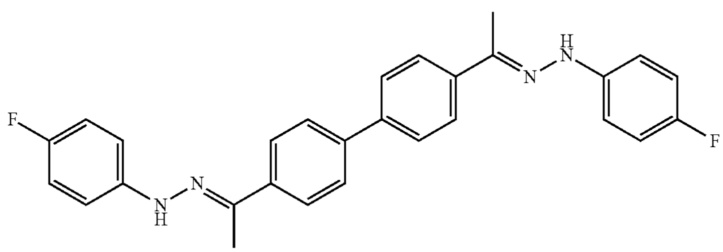 [SMILES: C/C(=N\Nc1ccc(F)cc1)c1ccc(-c2ccc(/C(C)=N/Nc3ccc(F)cc3)cc2)cc1] | 4<br>X = p-FPh<br>R = Me |
| 18a | 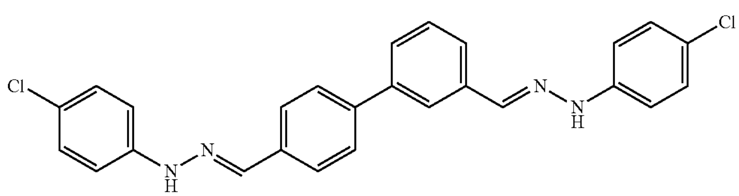 [SMILES: Clc1ccc(N/N=C/c2ccc(-c3cccc(/C=N/Nc4ccc(Cl)cc4)c3)cc2)cc1] | 3<br>X = p-ClPh<br>R = H |
| 18b | 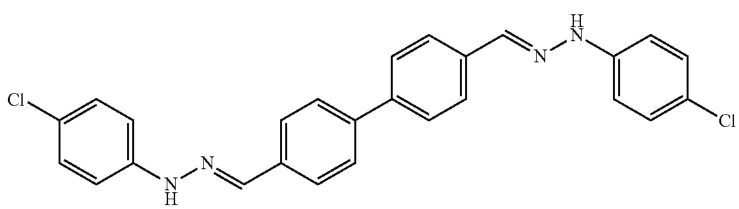 [SMILES: Clc1ccc(N/N=C/c2ccc(-c3ccc(/C=N/Nc4ccc(Cl)cc4)cc3)cc2)cc1] | 4<br>X = p-ClPh<br>R = H |
| 19a | 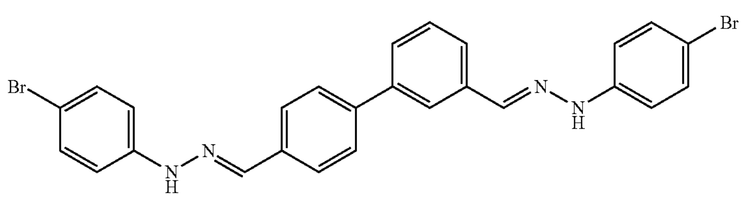 [SMILES: Brc1ccc(N/N=C/c2ccc(-c3cccc(/C=N/Nc4ccc(Br)cc4)c3)cc2)cc1] | 3<br>X = p-BrPh<br>R = H |
| 19b | 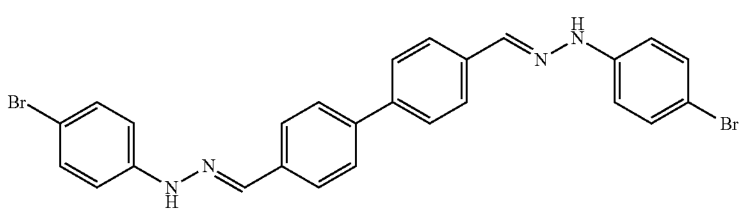 [SMILES: Brc1ccc(N/N=C/c2ccc(-c3ccc(/C=N/Nc4ccc(Br)cc4)cc3)cc2)cc1] | 4<br>X = p-BrPh<br>R = H |
| 20a | 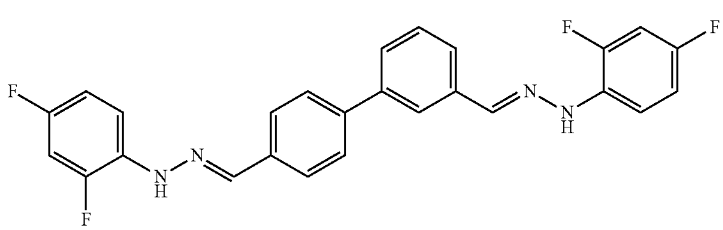 [SMILES: Fc1ccc(N/N=C/c2ccc(-c3cccc(/C=N/Nc4ccc(F)cc4F)c3)cc2)c(F)c1] | 3<br>X = o,p-diFPh<br>R = H |

-continued

| Compound Number | Structure | Substituents |
|---|---|---|
| 20b | 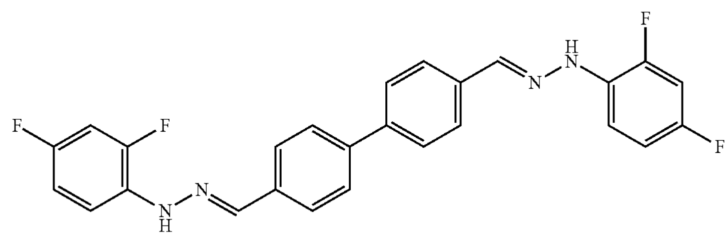 [SMILES: Fc1ccc(N/N=C/c2ccc(-c3ccc(/C=N/Nc4ccc(F)cc4F)cc3)cc2)c(F)c1] | 4<br>X = o,p-diFPh<br>R = H |
| 21a | 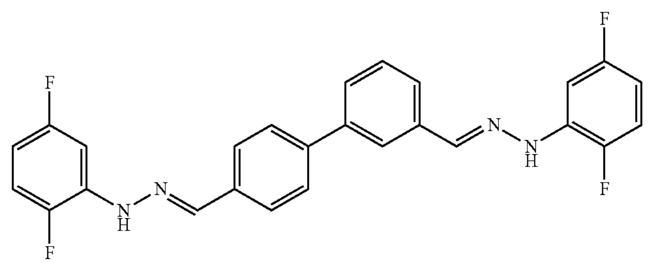 [SMILES: Fc1ccc(F)c(N/N=C/c2ccc(-c3cccc(/C=N/Nc4cc(F)ccc4F)c3)cc2)c1] | 3<br>X = o,m-diFPh<br>R = H |
| 21b | 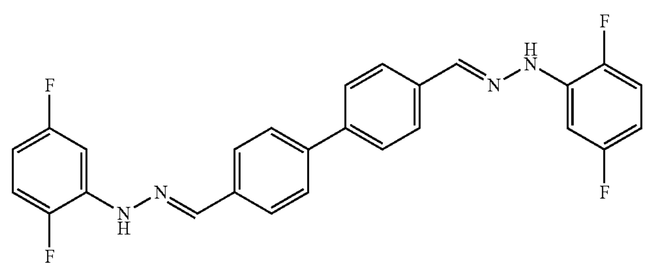 [SMILES: Fc1ccc(F)c(N/N=C/c2ccc(-c3ccc(/C=N/Nc4cc(F)ccc4F)cc3)cc2)c1] | 3<br>X = o,m-diFPh<br>R = H |
| 22a | 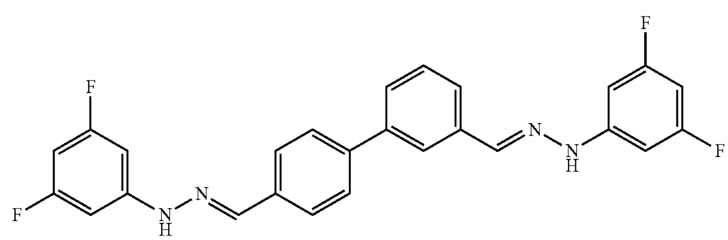 [SMILES: Fc1cc(F)cc(N/N=C/c2ccc(-c3cccc(/C=N/Nc4cc(F)cc(F)c4)c3)cc2)c1] | 3<br>X = m,m-diFPh<br>R = H |
| 22b | 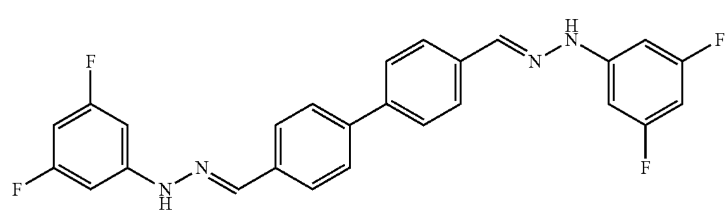 [SMILES: Fc1cc(F)cc(N/N=C/c2ccc(-c3ccc(/C=N/Nc4cc(F)cc(F)c4)cc3)cc2)c1] | 4<br>X = m,m-diFPh<br>R = H |
| 23b | 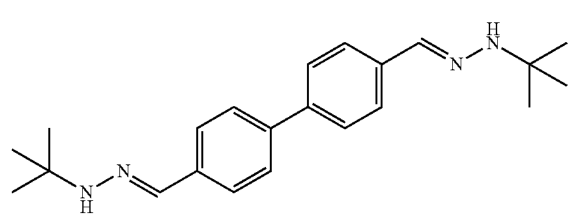 [SMILES: CC(C)(C)N/N=C/c1ccc(-c2ccc(/C=N/NC(C)(C)C)cc2)cc1] | 4<br>X = t-Bu<br>R = H |

| Compound Number | Structure | Substituents |
|---|---|---|
| 24a | 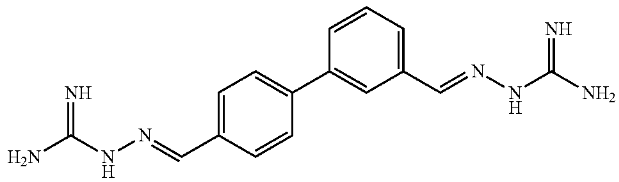 [SMILES: N=C(N)N/N=C/c1ccc(-c2cccc(/C=N/NC(=N)N)c2)cc1] | 3<br>X = C(N=H)NH$_2$<br>R = H |
| 24b | 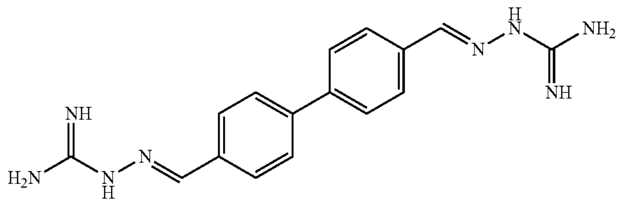 [SMILES: N=C(N)N/N=C/c1ccc(-c2ccc(/C=N/NC(=N)N)cc2)cc1] | 4<br>X = C(N=H)NH$_2$<br>R = H |
| 24c | 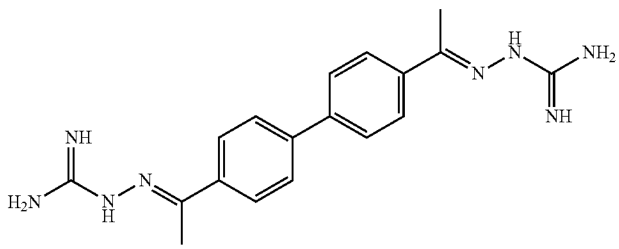 [SMILES: C/C(=N\NC(=N)N)c1ccc(-c2ccc(/C(C)=N/NC(=N)N)cc2)cc1] | 4<br>X = C(N=H)NH$_2$<br>R = Me |

Although described in detail below with respect to N,N'-Diaryl-bishydrazones of [1,1'-biphenyl]-3,4'-dicarboxaldehyde, [1,1'-biphenyl]-4,4'-dicarboxaldehyde, 4,4'-bisacetyl-1,1-biphenyl, and/or 4,4'-bisacetyl-1,1-biphenyl, as will be understood by those skilled in the art, the disclosure is not so limited and may include any other compound according to Formula I as discussed herein.

In some embodiments, the compounds disclosed herein form broad spectrum systemic antifungal agents. For example, in one embodiment, the compounds disclosed herein exhibit excellent antifungal activity against a broad spectrum of filamentous and non-filamentous fungi. In another embodiment, the compounds disclosed herein provide the broad spectrum antifungal activity without displaying any antibacterial activity. By providing antifungal activity without displaying antibacterial activity, the compounds disclosed herein reduce or eliminate concerns regarding antibiotic resistance as a result of antifungal treatment. In a further embodiment, the compounds disclosed herein display reduced hemolysis as compared to control antifungal agents, are fungistatic, and/or possess no mammalian cytotoxicity and/or toxicity with respect to hERG inhibition.

Also provided herein, in some embodiments, is a method of treating a systemic fungal condition, e.g., a fungal disease or fungal infection, by administering to a subject in need thereof a therapeutically effective amount of a compound according to Formula (I), a pharmaceutically acceptable salt thereof, or a pharmaceutically acceptable composition including a compound according to Formula (I) or a pharmaceutically acceptable salt thereof together with a pharmaceutically acceptable carrier. For example, in one embodiment, the method for treating a fungal condition includes administering to a subject in need thereof a therapeutically effective amount of any one or more of N,N'-Diaryl-bishydrazones of [1,1'-biphenyl]-3,4'-dicarboxaldehyde, [1,1'-biphenyl]-4,4'-dicarboxaldehyde, 4,4'-bisacetyl-1,1-biphenyl, or 4,4'-bisacetyl-1,1-biphenyl, pharmaceutically acceptable salts thereof, or a pharmaceutically acceptable composition including one or more of N,N'-Diaryl-bishydrazones of [1,1'-biphenyl]-3,4'-dicarboxaldehyde, [1,1'-biphenyl]-4,4'-dicarboxaldehyde, 4,4'-bisacetyl-1,1-biphenyl, or 4,4'-bisacetyl-1,1-biphenyl, or pharmaceutically acceptable salts thereof together with a pharmaceutically acceptable carrier.

The presently-disclosed subject matter is further illustrated by the following specific but non-limiting examples. The following examples may include compilations of data that are representative of data gathered at various times during the course of development and experimentation related to the presently-disclosed subject matter.

EXAMPLES

Example 1

This Example describes the formation of various compounds according to the instant disclosure, along with their activity as compared to existing compounds.

In recent years, the instant inventors, along with others, have investigated derivatives of chemical scaffolds that include aminoglycosides, benzimidazoles, azoles, haloperidol, and ebselen/ebsulfur as potential antifungal agents. Most recently, the instant inventors reported the development of bishydrazones 1 and 2 (FIG. 1) bearing either N-amidino and/or N-aryl groups, respectively, as new classes of antibacterial and antifungal agents. Although these first-generation bishydrazones 1 and 2 displayed good activity against various bacterial and fungal strains, the instant inventors also observed some unwanted inhibition of the human Ether-à-go-go-related (hERG) potassium ion channel associated with QT interval prolongation in the electrocardiogram and adverse cardiac events.

However, the instant inventors have discovered that alkoxy-substituted N,N'-diaryl groups attached to bishydrazones 3 (FIG. 1) on either 3,4'-biphenyl or 4,4'-biphenyl platforms eliminate this potential hERG toxicity associated with the previous bishydrazones. The alkoxy-substituted N,N'-diaryl-bishydrazones 3 exhibited particularly effective control of a broad spectrum of fungi relative to the previously reported bishydrazones 2, displayed minimal antibacterial activity, and possessed minimal hemolysis and toxicity with respect to hERG inhibition.

Results and Discussion

Synthesis of N,N'-diaryl-bishydrazones.

Figure 2:
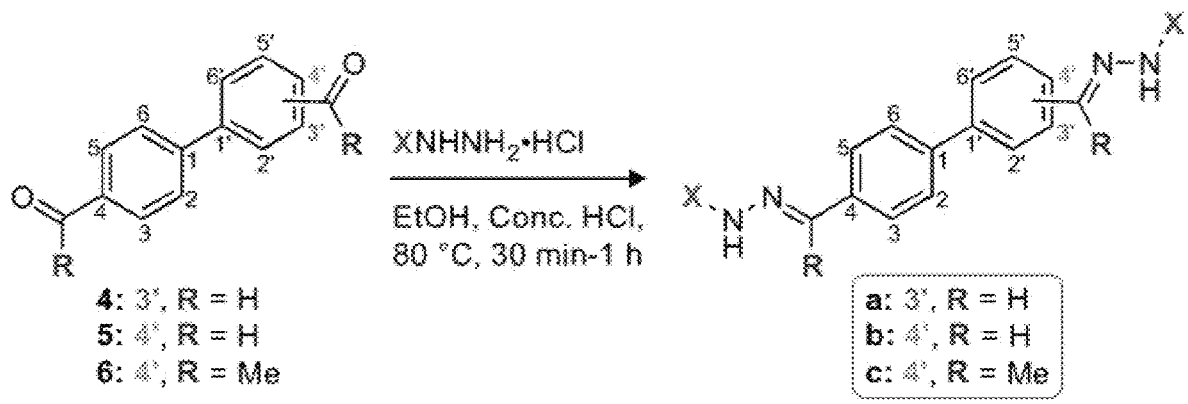
FIG. 2 shows a synthetic scheme for the preparation of compounds 7a-24c.

The acid-catalyzed condensation of [1,1'-biphenyl]-3,4'-dicarboxaldehyde (4), [1,1'-biphenyl]-4,4'-dicarboxaldehyde (5), or 4,4'-bisacetyl-1,1-biphenyl (6) with two equivalents of N-arylhydrazines at 80° C. furnished the N,N'-diaryl-bishydrazones 7-22 (FIG. 2). For comparison with these aryl-substituted bishydrazones, several bishydrazones with N,N'-dialkyl or N,N'-diamidino substituents were included in place of the N,N'-diaryl groups. The condensations of either tert-butylhydrazine or N-aminoguanidine secured the N,N'-dialkyl-bishydrazone 23b or the N,N'-diamidino-bishydrazones 24a-c, respectively. Yields varied over a considerable range, but no effort was invested in yield optimization. The (E,E)-stereochemistry of the bishydrazones 7-24 was anticipated on the basis of steric considerations and consistent with literature precedent in which heating benzaldehydes or acetophenones with arylhydrazines in an acidic medium produced the thermodynamically favored product.

Antibacterial Activity.

The activity of N,N'-diaryl-bishydrazones 7-22 was explored against various bacterial strains, including *Listeria monocytogenes*, methicillin-resistant *Staphylococcus aureus*, and vancomycin-resistant enterococci. In contrast with the N,N'-diamidino-bishydrazones 24a-c as well as related compounds in our prior study that displayed good antibacterial activity against these same strains, neither the N,N'-diaryl-bishydrazones 7-22 nor the N,N'-di-tert-butyl-bishydrazone 23b displayed antibacterial activity.

Antifungal Activity.

The activity of N,N'-diaryl-bishydrazones 7-22 was tested against a panel of seven strains of *C. albicans*: ATCC 10231(R) (A), ATCC 64124(R) (B), ATCC MYA-2876(S) (C), ATCC 90819(R) (D), ATCC MYA-2310(S) (E), ATCC MYA-1237(R) (F), and ATCC MYA-1003(R) (G). The activity of these bishydrazones 7-22 was also explored against a panel of three non-*albicans Candida* strains: *C. glabrata* ATCC 2001 (H), *C. krusei* ATCC 6258 (I), and *C. parapsilosis* ATCC 22019 (J). Finally, the activity of these bishydrazones 7-22 was explored against three *Aspergillus* strains: *A. flavus* ATCC MYA-3631 (K), *A. nidulans* ATCC 38163 (L), and *A. terreus* ATCC MYA-3633 (M). A concentration range of 0.03-31.3 µg/mL (Table 1) was used, along with commercially available antifungal agents, caspofungin (CAS) and voriconazole (VOR), as positive controls. MIC-0 values (i.e., no visible growth) were reported for the N,N'-diaryl-bishydrazones 7-22 and the control CAS, and MIC-2 values (i.e., 50% growth inhibition) were reported for VOR against all fungal strains tested with the exception of strain A. The limited solubility of several N,N'-diaryl-bishydrazones (i.e., 8a, 8b, 9a, 9b, 11a, 11b, and 14a) precluded determination of MIC values. For the bishydrazones with good solubility, antifungal activity was defined as excellent (<3.9 µg/mL), moderate (7.8-15.6 µg/mL), or poor (≥31.3 µg/mL) based on MIC values (Table 1).

TABLE 1

MIC values (in µg/mL) determined for compounds 7a-24c as well as for two control antifungal agents (CAS and VOR) against various yeast strains and filamentous fungi.

| Cpd # | Yeast strains | | | | | | | | | | Filamentous fungi | | |
|---|---|---|---|---|---|---|---|---|---|---|---|---|---|
| | A | B | C | D | E | F | G | H | I | J | K | L | M |
| 7a | 1.95 | 31.3 | 31.3 | 31.3 | 31.3 | 31.3 | 3.9 | >31.3 | 7.8 | >31.3 | 3.9 | 1.95 | 15.6 |
| 7b | 7.8 | >31.3 | >31.3 | 31.3 | >31.3 | >31.3 | >31.3 | >31.3 | >31.3 | >31.3 | 3.9 | 1.95 | 15.6 |
| 9c | 15.6 | >31.3 | >31.3 | >31.3 | >31.3 | >31.3 | 31.3 | >31.3 | 31.3 | 31.3 | >31.3 | >31.3 | >31.3 |
| 10a | 7.8 | 7.8 | >31.3 | 15.6 | 31.3 | >31.3 | 7.8 | >31.3 | 1.95 | 15.6 | 3.9 | 7.8 | >31.3 |
| 10b | 3.9 | >31.3 | 15.6 | 31.3 | >31.3 | >31.3 | 15.6 | >31.3 | 3.9 | >31.3 | >31.3 | 31.3 | >31.3 |
| 11c | 0.98 | 0.98 | 15.6 | 31.3 | 15.6 | 31.3 | 3.9 | 15.6 | 0.98 | 15.6 | >31.3 | >31.3 | >31.3 |
| 12a | 1.95 | >31.3 | 7.8 | 15.6 | >31.3 | 15.6 | 7.8 | >31.3 | 1.95 | 31.3 | 3.9 | 7.8 | >31.3 |
| 12b | 7.8 | >31.3 | >31.3 | >31.3 | >31.3 | >31.3 | >31.3 | >31.3 | 15.6 | 3.9 | 31.3 | >31.3 | >31.3 |
| 13b | >31.3 | >31.3 | >31.3 | >31.3 | >31.3 | >31.3 | 31.3 | >31.3 | >31.3 | >31.3 | >31.3 | >31.3 | 31.3 |
| 15a | 1.95 | 15.6 | 3.9 | 3.9 | 7.8 | 3.9 | 7.8 | 7.8 | 3.9 | >31.3 | >31.3 | 31.3 | >31.3 |
| 15b | 7.8 | 3.9 | 7.8 | 7.8 | 3.9 | 15.6 | 7.8 | 7.8 | 7.8 | 15.6 | >31.3 | 7.8 | >31.3 |
| 15c | 15.6 | 15.6 | 15.6 | 31.3 | 15.6 | 7.8 | 7.8 | 7.8 | 15.6 | >31.3 | >31.3 | >31.3 | >31.3 |
| 16b | >31.3 | >31.3 | >31.3 | >31.3 | >31.3 | >31.3 | >31.3 | >31.3 | >31.3 | >31.3 | >31.3 | >31.3 | >31.3 |
| 17a | 1.59-3.9 | 15.6 | 7.8 | >31.3 | 7.8 | 15.6 | 3.9 | >31.3 | >31.3 | 31.3 | 15.6 | 3.9 | >31.3 |
| 17b | 7.8 | 15.6 | 7.8 | 31.3 | 15.6 | 7.8 | 7.8 | 15.6 | 1.95 | 31.3 | 7.8 | 7.8 | >31.3 |
| 17c | 1.95 | 3.9 | 3.9 | 7.8 | 1.95 | 7.8 | 7.8 | 15.6 | 1.95 | 15.6 | >31.3 | 7.8 | >31.3 |
| 18a | 7.8 | 7.8 | 15.6 | 31.3 | 15.6 | 3.9 | 15.6 | 3.9 | 15.6 | 31.3 | 3.9 | >31.3 | >31.3 |
| 18b | >31.3 | >31.3 | >31.3 | >31.3 | >31.3 | >31.3 | >31.3 | >31.3 | 31.3 | 31.3 | >31.3 | >31.3 | 31.3 |
| 19a | 31.3 | 31.3 | 31.3 | >31.3 | >31.3 | 7.8 | 31.3 | 7.8 | >31.3 | >31.3 | 31.3 | >31.3 | >31.3 |
| 19b | >31.3 | >31.3 | >31.3 | >31.3 | >31.3 | >31.3 | >31.3 | >31.3 | >31.3 | 31.3 | >31.3 | >31.3 | >31.3 |
| 20a | 3.9 | 7.8 | 15.6 | 15.6 | 15.6 | 7.8 | 7.8 | 15.6 | 1.95 | 31.3 | 7.8 | 7.8 | 31.3 |
| 20b | 7.8 | >31.3 | >31.3 | 31.3 | >31.3 | >31.3 | >31.3 | >31.3 | >31.3 | >31.3 | >31.3 | >31.3 | >31.3 |
| 21a | >31.3 | >31.3 | >31.3 | >31.3 | >31.3 | >31.3 | >31.3 | >31.3 | >31.3 | >31.3 | >31.3 | >31.3 | >31.3 |
| 21b | 31.3 | >31.3 | >31.3 | >31.3 | >31.3 | >31.3 | >31.3 | >31.3 | >31.3 | >31.3 | >31.3 | >31.3 | >31.3 |
| 22a | 3.9 | 15.6 | 31.3 | >31.3 | >31.3 | 31.3 | 31.3 | >31.3 | >31.3 | >31.3 | >31.3 | >31.3 | >31.3 |
| 22b | 15.6 | >31.3 | >31.3 | >31.3 | >31.3 | >31.3 | >31.3 | >31.3 | >31.3 | >31.3 | >31.3 | >31.3 | >31.3 |
| 23b | 31.3 | 31.3 | >31.3 | >31.3 | 31.3 | >31.3 | 15.6 | 31.3 | >31.3 | >31.3 | 31.3 | 31.3 | >31.3 |
| 24a | 1.95-3.9 | 3.9 | 3.9 | >31.3 | 3.9 | 7.8 | >31.3 | 3.9 | 1.95 | 1.95 | >31.3 | 7.8 | 7.8 |

TABLE 1-continued

MIC values (in µg/mL) determined for compounds 7a-24c as well as for two control antifungal agents (CAS and VOR) against various yeast strains and filamentous fungi.

| Cpd # | Yeast strains | | | | | | | | | | Filamentous fungi | | |
|---|---|---|---|---|---|---|---|---|---|---|---|---|---|
| | A | B | C | D | E | F | G | H | I | J | K | L | M |
| 24b | 31.3 | >31.3 | >31.3 | >31.3 | >31.3 | >31.3 | 15.6 | >31.3 | 15.6 | 3.9 | >31.3 | >31.3 | >31.3 |
| 24c | 3.9 | 3.9 | 15.6 | 3.9 | 15.6 | 15.6 | 15.6 | 7.8 | 3.9 | 1.95 | >31.3 | 15.6 | >31.3 |
| CAS | 0.975 | 0.24 | 0.06 | 0.12 | 0.12 | 0.24 | 0.48 | 0.06 | 0.48 | 1.95 | >31.3 | >31.3 | >31.3 |
| VOR | 0.975 | 0.24 | 0.06 | 0.12 | 0.12 | 0.24 | 0.48 | 0.06 | 0.48 | 1.95 | >31.3 | >31.3 | >31.3 |

Yeast strains: A = *Candida albicans* ATCC 10231(R), B = *C. albicans* ATCC 64124(R), C = *C. albicans* ATCC MYA-2876(S), D = *C. albicans* ATCC 90819(R), E = *C. albicans* ATCC MYA-2310(S), F = *C. albicans* ATCC MYA-1237(R), G = *C. albicans* ATCC MYA-1003(R), H = *Candida glabrata* ATCC 2001, I = *Candida krusei* ATCC 6258, J = *Candida parapsilosis* ATCC 22019.
Note:
Here, the (S) and (R) indicate that ATCC reports these strains to be susceptible (S) and resistant (R) to ITC and FLC.
Filamentous fungi: K = *Aspergillus flavus* ATCC MYA-3631, L = *Aspergillus nidulans* ATCC 38163, M = *Aspergillus terreus* ATCC MYA-3633.
Known antifungal agents: CAS = caspofungin, VOR = voriconazole.
[a] For yeast strains: MIC-0 values are reported for all compounds tested and CAS and VOR against strain. A. MIC-2 value is reported for VOR against strains B-J. For filamentous fungi (strains K-M), MIC-0 values are reported for all compounds.
Note:
The MIC values for compounds 8a, 8b, 9a, 9b, 11a, 11b, and 14a were not determined as these compounds are not soluble.

The MIC data in Table 1 identified the N,N'-diarylbishydrazones 13b, 16b, 18b, 19b, 21a, and 21b to be inactive as antifungal agents, and this finding led us to discount bishydrazones with a symmetrical 4,4'-substitution pattern (series b, FIG. 2) in the biphenyl platform in favor of those with an unsymmetrical 3,4'-substitution pattern (series a, FIG. 2). Consistent with this generalization that a symmetrical 4,4'-substitution pattern produced largely inactive compounds, bishydrazones 9c, 20b, 22b, and 23b also displayed poor activity against all fungal strains tested with exception of 9c, 20b, and 22b against strain A (15.6 µg/mL, 7.8 µg/mL and 15.6 µg/mL, respectively) and 23b against strain H (15.6 µg/mL). Also consistent with this generalization, bishydrazone 19a with an unsymmetrical 3,4'-substitution pattern displayed moderate activity against two strains F and H (7.8 µg/mL), and bishydrazone 22a displayed excellent activity against strain A (3.9 µg/mL) and moderate activity (15.6 µg/mL) against strain B.

Turning to the bishydrazones that displayed activity against multiple strains, bishydrazone 7a exhibited excellent activity against strains A, G, K, and L (1.95-3.9 µg/mL) and moderate activity against strains I and M (7.8-15.6 µg/mL). Bishydrazone 7b displayed excellent activity (1.95-3.9 µg/mL) against strains K and L, and bishydrazones 10a and 10b displayed excellent activity (1.953.9 µg/mL) against strains I and K and against strains A and I, respectively. Compound 11c exhibited excellent activity (0.98-3.9 µg/mL) against strains A, B, G, and I as well as moderate activity (15.6 µg/mL) against strains C, E, H, and J. Similarly, compound 12a displayed excellent activity (1.95-3.9 µg/mL) against strains A, I, and K as well as moderate activity (7.8-15.6 µg/mL) against strains C, D, F, G, and L. Bishydrazone 12b exhibited excellent activity (3.9 µg/mL) against strain J, but only moderate activity (7.8-15.6 µg/mL) against strains A and I, a finding again in accord with the generalization regarding a preference for bishydrazones with an unsymmetrically substituted biphenyl platform.

Finally, in addition to bishydrazone 12a mentioned above, the bishydrazones 15a-c, 17a-c, 18a, and 20a possessed the breadth of activity that was desired and displayed overall antifungal activity against all the strains tested. Bishydrazones 15a and 17c were among the best of the series and displayed excellent activity (1.95-3.9 µg/mL) against strains A, C, D, F, and I and against strains A, B, C, E, and I, respectively. Even though bishydrazones 15a and 17c were superior in terms of their activity, bishydrazones 15b, 17a, 18a, and 20a also exhibited good activity against the majority of the fungal strains tested. Bishydrazone 15b displayed excellent activity (3.9 µg/mL) against strains B and E and exhibited moderate activity (7.8-15.6 µg/mL) against strains A, C, D, F, G, H, I, J, and L. In addition, bishydrazones 17a, 18a, and 20a also displayed excellent activity (1.95-3.9 µg/mL) against strains A, G, and L; G and J; and A and I, respectively. Among the bishydrazones 15 and 17, bishydrazone 15c only exhibited moderate activity (7.8-15.6 µg/mL) against strains A-C and E-I, whereas compound 17b displayed excellent activity (1.95 µg/mL) against strain I as well as moderate activity (7.8-15.6 µg/mL) against strains A-C, E-H, K, and L. In comparison with the FDA approved antifungal agents, CAS and VOR, some of these bishydrazones exhibited comparable or superior activity against strains A, I, and J and superior activity against the filamentous strains K-M.

Sar Analysis.

These latter findings required a refinement of the initial generalization regarding the preference for an unsymmetrical substitution pattern in the biphenyl platform over a symmetrical substitution pattern in driving the observed antifungal activities in these bishydrazones. In cases where the R group is a hydrogen (series a, FIG. 2), the most active bishydrazones (e.g., 12a, 15a, 17a, 18a and 20a) possessed the unsymmetrical 3,4'-substitution pattern in the biphenyl platform, but in cases where the R group is a methyl (series c, FIG. 2), the most active bishydrazones possessed the symmetrical 4,4'-substitution pattern in the biphenyl platform. As for any generalization, there were exceptions such as the bishydrazones with symmetrically substituted biphenyl platforms (e.g., 15b and 17b) in which presumably the substituents on the aryl rings overrode any disadvantage in activity conferred by the symmetrical substitution pattern on the biphenyl platform. As a further illustration of this point, several bishydrazones where the R group is a methyl (series c, FIG. 2) possessed excellent activity (e.g., 15c and 17c) despite the symmetrical nature of the 4,4'-biphenyl platform.

Among the substitutents on the N-aryl groups, the bishydrazones with para-fluorophenyl, para-chlorophenyl and para-methoxyphenyl groups possessed the best spectrum of activity against various strains and the most potent activity as judged by their MIC values. Other regioisomers, such as the meta-fluorophenyl analogue 12a, displayed good activity, including promising activity against several filamentous fungi (strains K and L), but overall, the meta-fluorophenyl analogue 12a displayed a spectrum slightly less promising than that of the corresponding para-fluorophenyl analogues 15a-c. In addition, the meta-fluorophenyl analogue 12a displayed good activity only in the biphenyl platform with 3,4'-substitution (series a), and introducing the meta-fluorophenyl group in other platforms (series b and c) led to inactive compounds. The addition of multiple fluoro groups (i.e., N,N'-bis-ortho,para-difluorophenyl-bishydrazone 20a versus N,N'-di-para-fluorophenyl-bishydrazone 17a led to a modest improvement in activity against three strains (D, F, and K), but otherwise comparable activity. The ortho, meta- and meta, meta-difluorophenyl analogues 21a,b and 22a,b, respectively, showed no activity.

Other para-substituted N-aryl groups, including the para-bromo-, para-cyano-, para-trifluoromethyl-, and para-isopropoxyphenyl groups, led to N,N'-diaryl-bishydrazones with diminished activity in both scope and potency. Other ortho- and meta-substituted N-aryl groups, such as the ortho-fluoro-, ortho-methoxy, meta-methoxy-, and ortho-nitrophenyl groups, led to N,N'-diaryl-bishydrazones either with diminished solubility or diminished activity in both scope and potency. Finally, the two bishydrazones 23b and 24a-c with N,N'-dialkyl groups and N,N'-diamidino groups, respectively were inactive in the case of 23b and marginally active in the cases of 24a-c.

Antibiofilm Activity.

Biofilms are complex communities of one or more species of microorganisms encased in extracellular polymeric substances and attached to not only a solid surface but also to each other. Because of their complex, matrix-like nature, antifungal agents are often unable to reach the pathogens embedded in these networks. The antibiofilm activity of 4,4'-bis((E)-1-(2-(4-fluorophenyl)hydrazono)ethyl)-1,1'-biphenyl (17c) and VOR were evaluated against biofilms of *C. albicans* ATCC 10231 (strain A) and *C. albicans* ATCC 64124 (strain B) by a tetrazolium salt XTT reduction assay (Table 2). The $SMIC_{50}$ and $SMIC_{99}$ values (i.e., drug concentration required to inhibit the metabolic activity of the biofilm by 50% and 99%, respectively) for bishydrazone 17c and VOR ranged from 8 to 16 μg/mL for the $SMIC_{50}$ and were >32 μg/mL for the $SMIC_{99}$. The SMIC values for bishydrazone 17c against the biofilm formed by strains A and B increased by 4- to 16-fold and 4- to 8-fold, respectively, as compared to their corresponding planktonic MIC values. This increase reflected some resistance of *Candida* biofilms against the bishydrazone 17c. VOR displayed a similar trend against the biofilms formed by strains A and B. The results suggested that bishydrazone 17c would require a higher concentration to eliminate pre-formed biofilms of *C. albicans* strains A and B.

TABLE 2

Antibiofilm activity of compound 17c and VOR against *C. albicans* 10231 (strain A) and *C. albicans* 64124 (strain B) biofilms.

| | C. albicans 10231 (strain A) | | C. albicans 64124 (strain B) | |
|---|---|---|---|---|
| Cpd # | $SMIC_{50}$ (μg/mL) | $SMIC_{99}$ (μg/mL) | $SMIC_{50}$ (μg/mL) | $SMIC_{99}$ (μg/mL) |
| 17c | 8 | >32 | 16 | >32 |
| VOR | 16 | >32 | 16 | >32 |

Cytotoxicity.

Figure 3A:
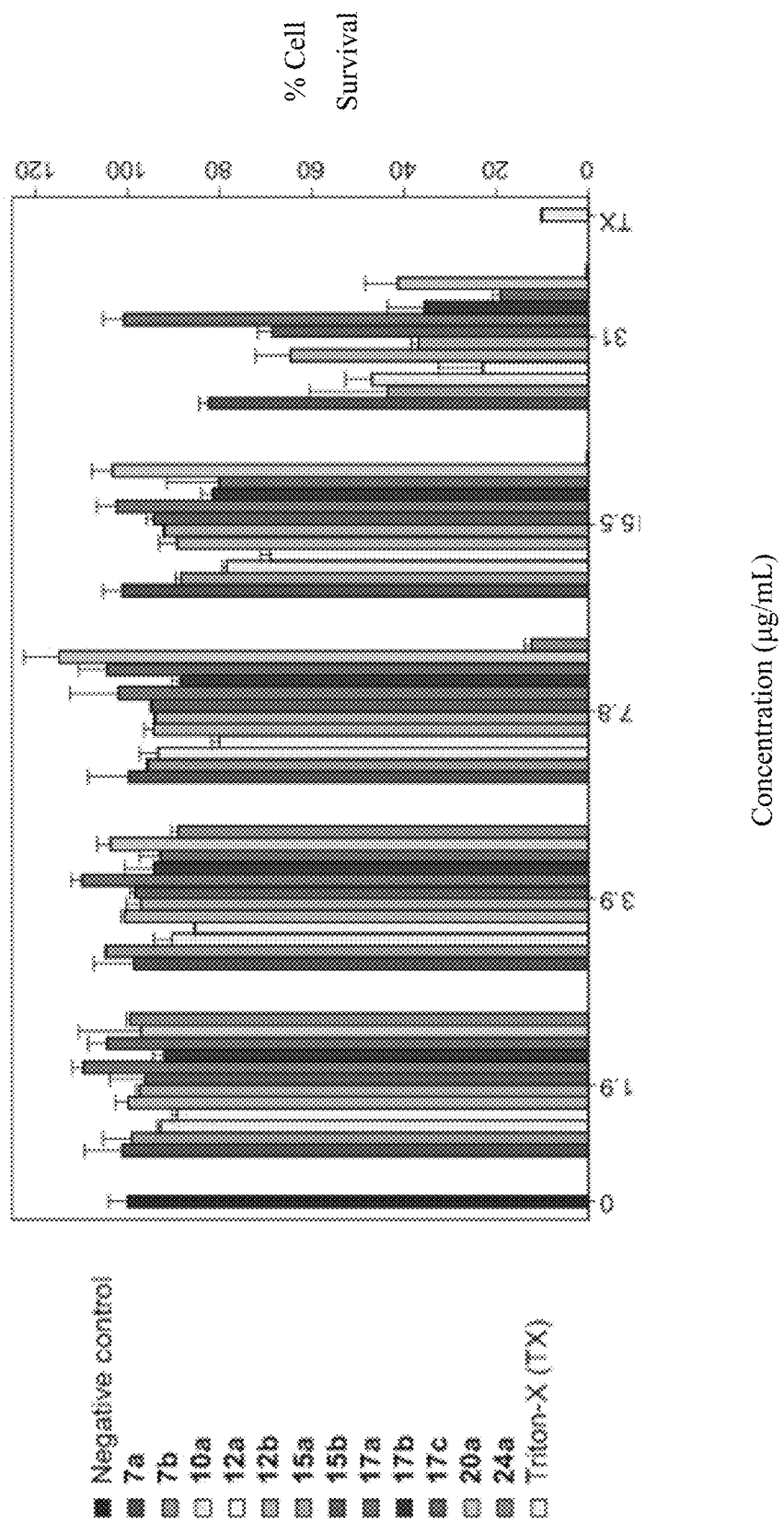
FIGS. 3A-B show graphs illustrating mammalian cell cytotoxicity of compounds 7a, 7b, 10a, 12a, 12b, 15a, 15b, 17a, 17b, 17c, 20a, and 24a against (A) lung cancer A549 and (B) normal BEAS-2B cell lines.
Figure 3B:
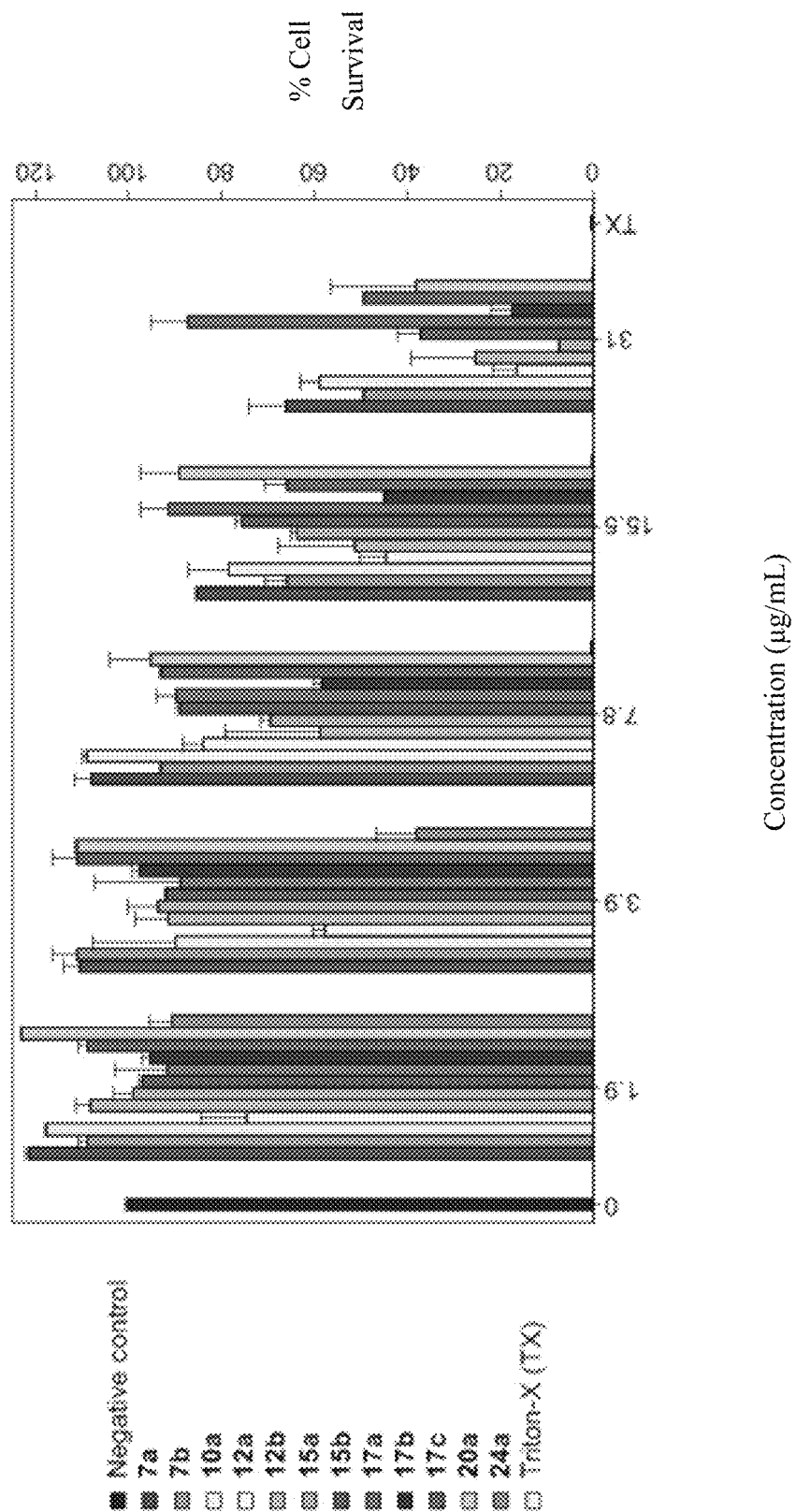

Having established the potent antifungal activity of the N,N'-diaryl-bishydrazones, it was important to consider their potential toxicity towards mammalian cells. The toxicity profile of N,N'-diaryl-bishydrazones 7a,b, 10a, 12a,b, 15a,b, 17a-c, 20a and N,N'-diamidino-bishydrazone 24a was investigated against two mammalian cell lines A549 and BEAS-2B (FIGS. 3A-B). In general, against these cell lines a concentration-dependent toxicity was observed for these bishydrazones. When tested against the A459 cell line at 31 μg/mL, the most active bishydrazones 15a,b and 17a were found to be generally non-toxic. Similarly, the bishydrazones 12a, 17c, and 20a displayed no toxicity against A549 at 15.5 μg/mL. Against the BEAS-2B cell line, a similar trend was observed with the bishydrazones 15a,b, 17c, and 20a found to be non-toxic at 15.5 μg/mL. Bishydrazone 17a was non-toxic at 31 μg/mL against the BEAS-2B cell line. It is important to note that the non-toxic nature of N,N'-diaryl-bishydrazones when compared to N,N'-diamidino-bishydrazone 24a combined with their excellent MIC values can be used to make a case for their further evaluation.

Hemolysis Assay.

Figure 4:
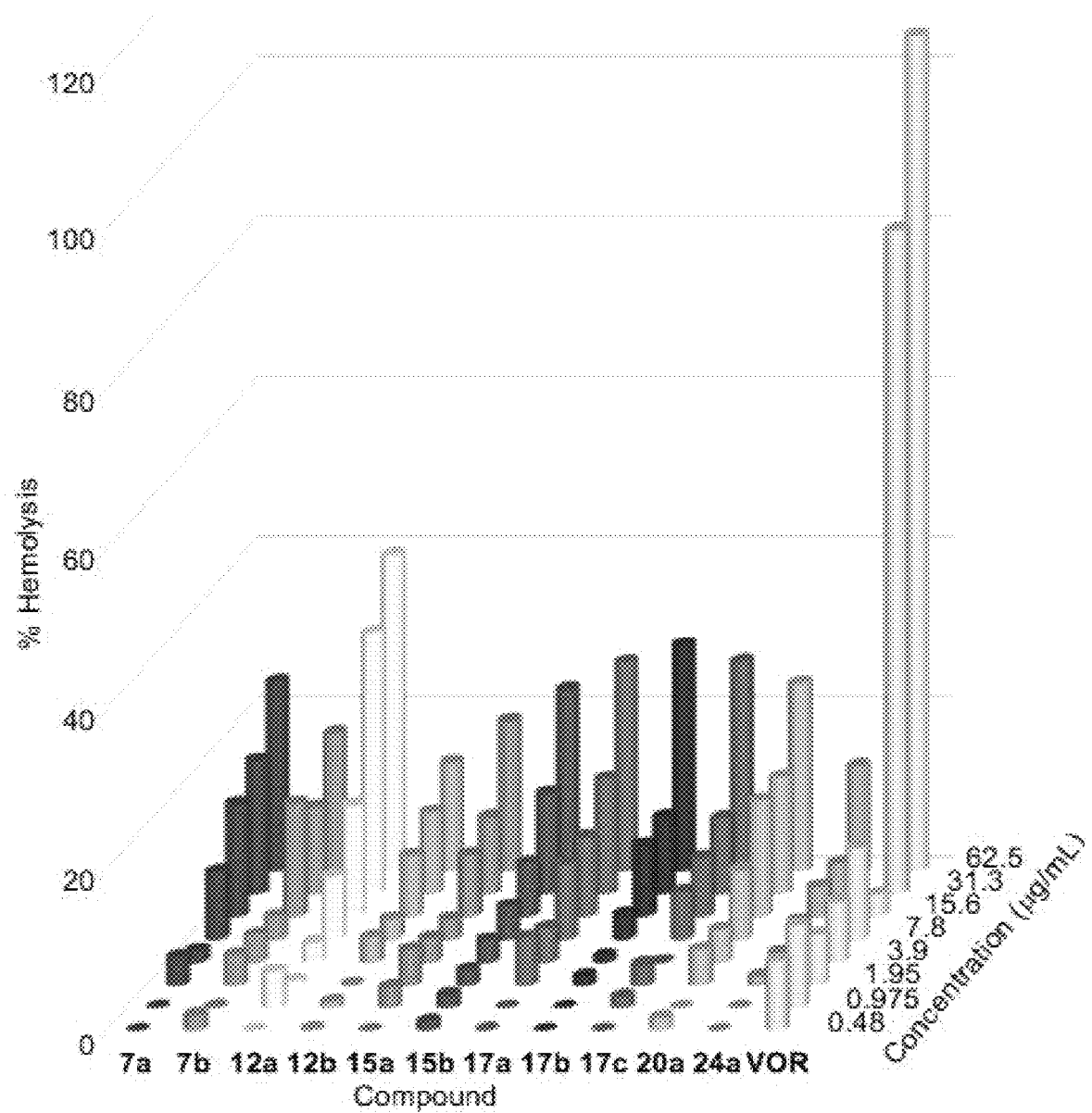
FIG. 4 shows a 3D bar graph depicting the dose-dependent hemolytic activity of 7a, 7b, 12a, 12b, 15a, 15b, 17a, 17b, 17c, 20a, 24a, and VOR against mRBCs. mRBCs were treated and incubated for 1 h at 37° C. with bishydrazones and VOR at concentrations ranging from 0.48 to 62.5 μg/mL. Triton X-100 (1% v/v) was used as a positive control (100% hemolysis, not shown).
Figure 5A:
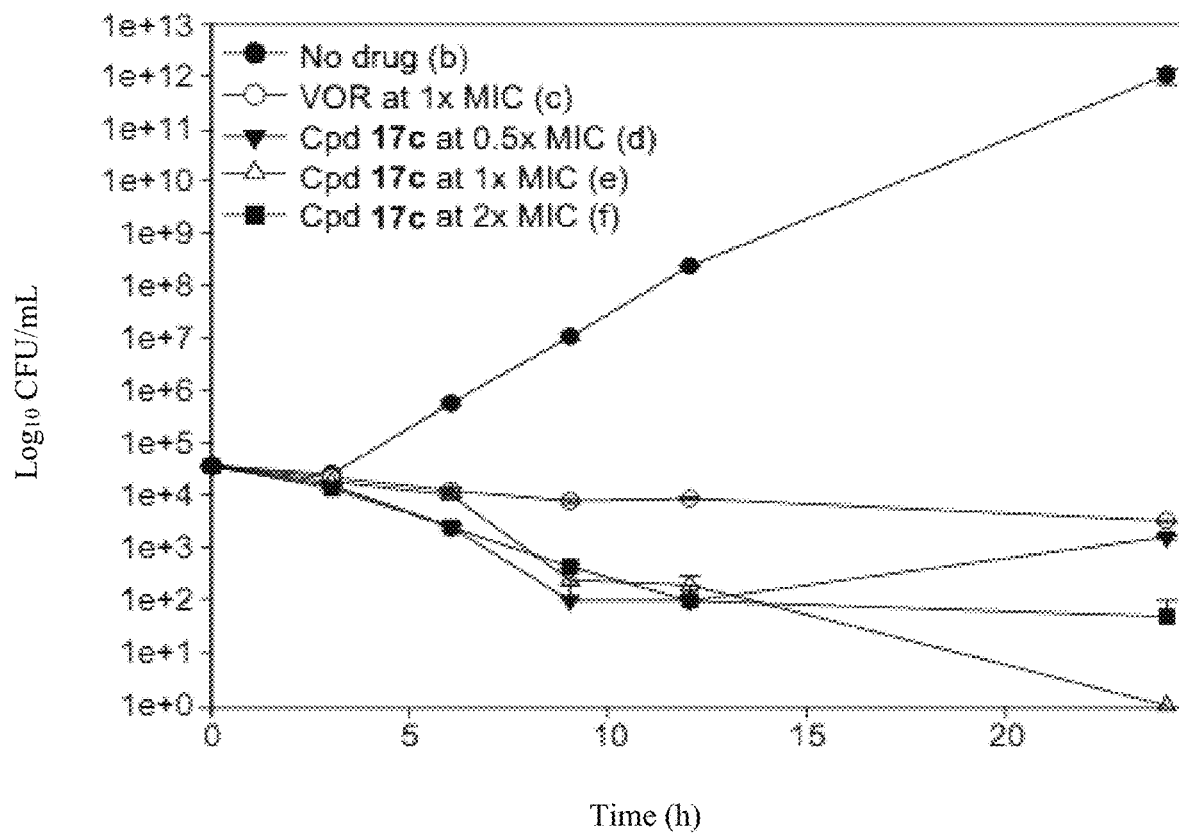
FIGS. 5A-D show graphs and images illustrating antifungal activity of VOR and compound 17c against *C. albicans* ATCC 10231 (strain A) and *C. albicans* ATCC 64124 (strain B). (A) Shows a graph illustrating time-kill curves for VOR and compound 17c against *C. albicans* ATCC 10231 (strain A). (B) Shows an image illustrating the cultures of (A) treated with resazurin after 24 hours for fungal growth detection. (C) Shows a graph illustrating time-kill curves for VOR and compound 17c against *C. albicans* ATCC 64124 (strain B). (D) Shows an image illustrating the cultures of (C) treated with resazurin after 24 hours for fungal growth detection. For (A) and (C), fungal strains were treated with no drug (black circles), VOR at 1×MIC (white circle), and compound 17c at 0.5×MIC (inverted black triangle), 1×MIC (white triangle), and 2×MIC (black square). For (B) and (D), a=sterile control; b=no drug; c=VOR at 1×MIC; d=compound 17c at 0.5×MIC; e=compound 17c at 1×MIC; and f=compound 17c at 2×MIC.
Figure 5B:
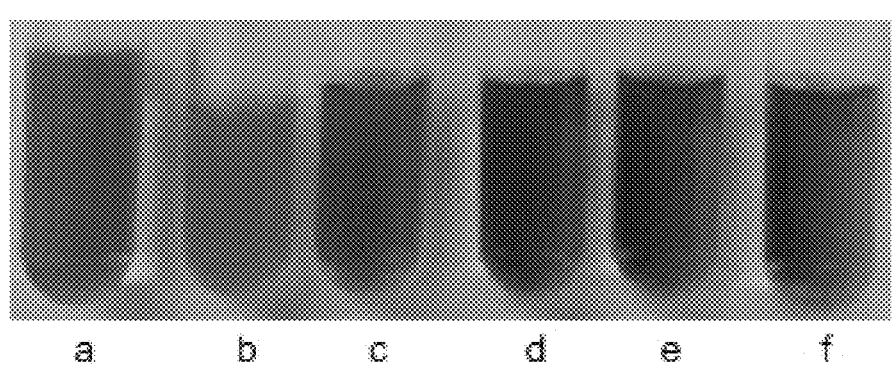
Figure 5C:
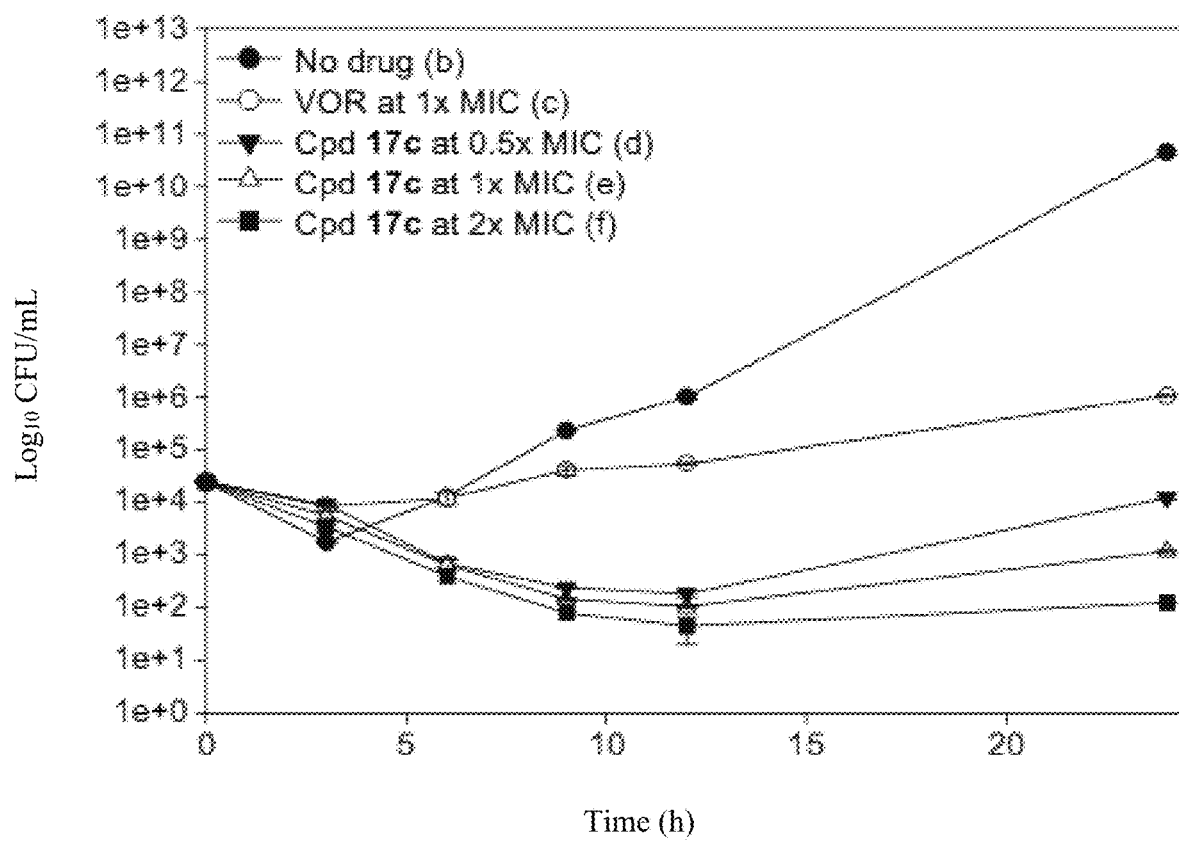
Figure 5D:
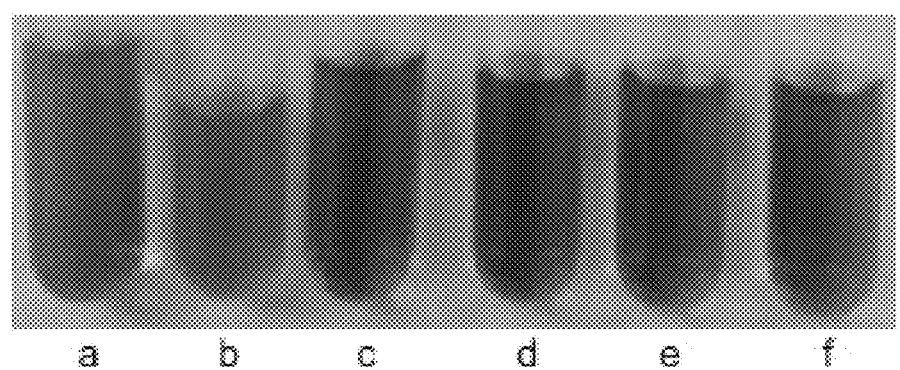
Figure 6F:
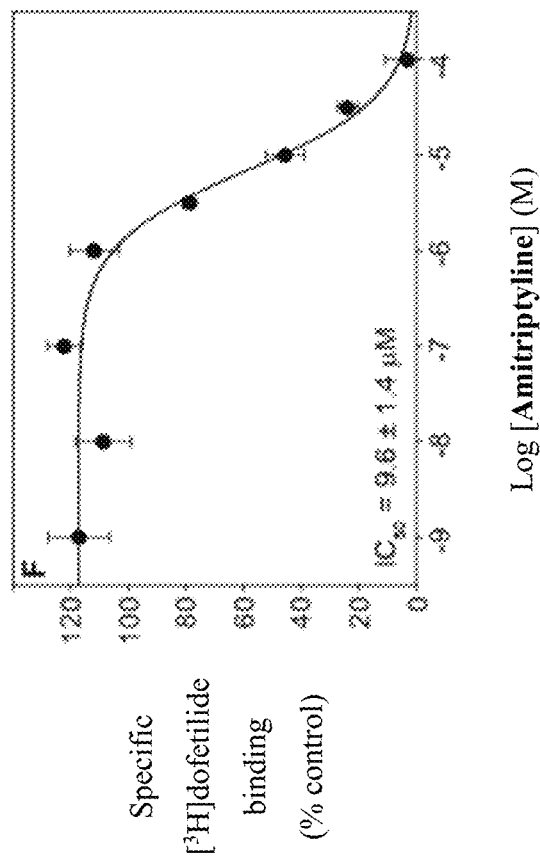
Figure 6E:
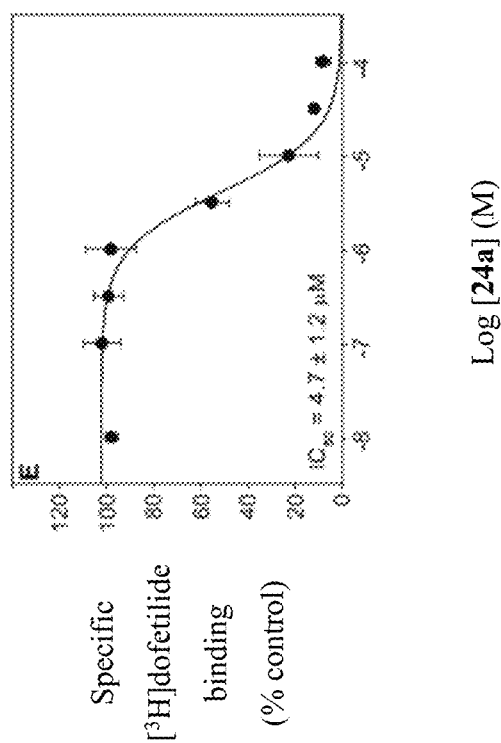

Although the N,N'-diaryl-bishydrazones 7a,b, 12a,b, 15a, b, 17a-c, and 20a and the N,N'-diamidino-bishydrazone 24a showed potent antifungal activities and limited toxicity, it was important to establish that these agents showed selectivity for fungal cells over mammalian cells. Thus, the hemolytic activity for these bishydrazones was investigated against murine red blood cells (mRBCs). Overall, these compounds displayed little or no hemolysis of mRBCs for concentrations as high as 15.6 μg/mL (FIG. 4 and Table 3). Bishydrazones 7a,b displayed <25% and <20% hemolysis at concentration of 62.5 μg/mL which are 1- to 32-fold higher than their overall MIC values. Bishydrazones 12b displayed lower hemolysis levels (<20% at 62.5 μg/mL) than those observed for 12a (<20% at 15.6 μg/mL). In addition, at 62.5 μg/mL, bishydrazones 12b, 15a,b and 17a-c only lysed less than 20% to 30% of mRBCs. These values were again 1 to 32-fold higher than the overall MIC values reported in Table 1 for these bishydrazones. Finally, bishydrazone 20a displayed <25% hemolysis (1- to 32-fold of its overall MIC values) and bishydrazone 24a at concentrations of 62.5 μg/mL displayed <20% hemolysis (1- to 32-fold of its overall MIC values).

TABLE 3

Percentage of hemolysis caused by the compounds and VOR against mouse erythrocytes with the error bars (±SDEV).

| | Concentration (μg/mL) | | | | | | | |
|---|---|---|---|---|---|---|---|---|
| Cpd # | 0.48 | 0.975 | 1.95 | 3.9 | 7.8 | 15.6 | 31.3 | 62.5 |
| 7a | 0 | 0 | 3.5 ± 3.3 | 1.5 ± 0.9 | 8.5 ± 5.1 | 14.1 ± 0.1 | 16.7 ± 0.9 | 23.6 ± 2.8 |
| 7b | 2.0 ± 2.8 | 0.1 ± 0.1 | 3.7 ± 1.6 | 3.4 ± 1.7 | 2.9 ± 1.1 | 14.1 ± 6.0 | 10.8 ± 0.6 | 17.2 ± 5.0 |
| 12a | 0 | 4.6 ± 2.5 | 0.6 ± 0.6 | 2.5 ± 2.7 | 7.9 ± 0.1 | 13.9 ± 0.1 | 32.6 ± 9.6 | 39.5 ± 12.1 |
| 12b | 0.2 ± 0.3 | 0.8 ± 0.9 | 0 | 3.2 ± 3.0 | 2.6 ± 1.6 | 7.7 ± 3.1 | 10.3 ± 0.2 | 13.6 ± 9.2 |
| 15a | 0 | 2.6 ± 3.4 | 4.5 ± 1.7 | 3.0 ± 1.6 | 2.6 ± 2.8 | 7.8 ± 3.3 | 9.6 ± 1.7 | 18.8 ± 0.1 |
| 15b | 1.2 ± 1.7 | 1.6 ± 2.3 | 1.9 ± 0.3 | 2.8 ± 0.6 | 4.2 ± 3.1 | 6.7 ± 2.0 | 12.6 ± 4.7 | 22.7 ± 6.1 |

TABLE 3-continued

Percentage of hemolysis caused by the compounds and VOR against mouse erythrocytes with the error bars (±SDEV).

| Cpd # | Concentration (µg/mL) | | | | | | | |
|---|---|---|---|---|---|---|---|---|
| | 0.48 | 0.975 | 1.95 | 3.9 | 7.8 | 15.6 | 31.3 | 62.5 |
| 17a | 0.1 ± 0.1 | 0 | 6.0 ± 2.1 | 4.3 ± 1.6 | 9.5 ± 3.3 | 9.9 ± 2.1 | 14.4 ± 0.9 | 26.1 ± 11.1 |
| 17b | 0 | 0 | 1.1 ± 1.5 | 0.7 ± 1.1 | 3.2 ± 3.0 | 9.0 ± 8.5 | 9.6 ± 6.7 | 28.3 ± 4.1 |
| 17c | 0 | 1.4 ± 1.1 | 2.6 ± 0.9 | 2.6 ± 2.7 | 5.9 ± 0.3 | 7.4 ± 1.1 | 9.5 ± 2.2 | 26.2 ± 7.7 |
| 20a | 1.6 ± 2.2 | 0 | 4.5 ± 2.3 | 4.2 ± 2.8 | 8.6 ± 1.6 | 14.6 ± 1.6 | 14.6 ± 0.7 | 23.5 ± 1.6 |
| 24a | 0 | 0 | 1.1 ± 2.2 | 1.2 ± 1.7 | 2.3 ± 0.5 | 3.8 ± 0.5 | 3.8 ± 1.7 | 13.1 ± 0.2 |
| VOR | 8.7 ± 5.4 | 10.3 ± 2.1 | 6.3 ± 1.9 | 7.5 ± 0.5 | 11.4 ± 10.9 | 2.8 ± 1.3 | 83.0 ± 4.5 | 100.0 ± 2.3 |

Time-Kill Studies.

To determine the fungistatic or fungicidal nature of the compounds, time-kill assays were next performed over a 24-hour period with 4,4'-bis((E)-1-(2-(4-fluorophenyl)hydrazono)ethyl)-1,1'-biphenyl (17c). The bishydrazone 17c and VOR, which served as a positive control, were tested against fungal strains C. albicans ATCC 10231 (A) and C. albicans ATCC 64124 (B) (FIGS. 5A-D). Against strain A, bishydrazone 17c was fungistatic and displayed levels of fungal growth reduction better than the control drug VOR at the same concentrations. Even at concentrations one-half of the MIC value, bishydrazone 17c displayed a greater reduction in fungal growth than concentrations of VOR equal to the MIC value. The bishydrazone 17c also displayed fungistatic activity against strain B at concentrations up to twice its MIC value. At concentrations equal to or even one-half of the MIC value, bishydrazone 17c displayed a greater reduction in fungal growth against strain B than concentrations of VOR equal to the MIC value. Overall, the bishydrazone 17c performed better in time-kill studies than the control drug VOR.

hERG Binding Studies.

Finally, N,N'-diaryl-bishydrazones 15a,b, 17a, and 17c as well as N,N'-diamidino-bishydrazone 24a were selected for evaluation of their hERG affinity. Inhibition of hERG channel can result in cardiac arrest, which emphasizes the importance of evaluation for hERG affinity for developing drug candidates according to the U. S Food and Drug administration (FDA) and European Medicines Agency (EMA). [$^3$H]-dofetilide binding assay was performed using HEK-293 cell membranes expressing the hERG channel to evaluate the activity of N,N'-diaryl-bishydrazones 15a,b, 17a, 17c and N,N'-diamidino-bishydrazone 24a for hERG affinity (FIGS. 6A-F). Amitriptyline (final concentration, 1 mM) was used as the positive control and exhibited an $IC_{50}$ value (9.6±1.4 µM) that was in agreement with published values. Compounds exhibiting $IC_{50}$ values of less than 1 µM have high affinity for hERG channel; compounds exhibiting $IC_{50}$ values in the range of 1-10 µM have moderate affinity; and compounds exhibiting $IC_{50}$ values of greater than 10 µM have low affinity for hERG channel. The $IC_{50}$ values for hERG inhibition of [$^3$H]-dofetilide binding for N,N'-diaryl-bishydrazones 15a,b and 17a, and 17c were >30 µM and therefore showed no hERG inhibition. By way of comparison, the $IC_{50}$ value for the N,N'-diamidino-bishydrazone 24a was 4.66±1.66 µM that indicated an intermediate level of inhibition. It is important to point out that the second generation N,N'-diaryl-bishydrazones 15a,b, 17a, and 17c displayed low affinity for hERG channel. Combined with the fact that they are non-toxic against mammalian cells, these compounds are better as antifungal agents than the previously reported first generation of N,N'-diamidino-bishydrazones.

CONCLUSIONS

In summary, a straightforward synthesis of N,N'-diaryl-bishydrazones 7-22 with (E,E)-stereochemistry that utilizes the acid-catalyzed condensation of [1,1'-biphenyl]-3,4'-dicarboxaldehyde (4), [1,1'-biphenyl]-4,4'-dicarboxaldehyde (5), or 4,4'-bisacetyl-1,1-biphenyl (6) (FIG. 2) has been developed. An N,N'-dialkyl and an N,N'-diamidino-bishydrazone was also included for comparison purposes. Neither the N,N'-diaryl-bishydrazones 7-22 or the N,N'-dialkyl-bishydrazone 23b displayed antibacterial activity. A detailed study (Table 1) of the antifungal activity of the N,N'-diaryl-bishydrazones 7-22 was performed against a panel of seven strains of C. albicans. Commercially available antifungal agents, caspofungin (CAS) and voriconazole (VOR), were used as positive controls.

This study of structure-activity relationships identified three leading candidates based on MIC values: the N,N'-di-para-fluorophenyl-bishydrazones 17a-c that displayed excellent activity against both yeast strains and filamentous fungi; the N,N'-di-para-methoxyphenyl-bishydrazones 15a-c that displayed excellent activity against a range of yeast strains but only modest effects against filamentous fungi; and the N,N'-di-para-chlorophenyl-bishydrazone 18a with a 3,4'-substitution pattern in the biphenyl platform that displayed excellent activity only against yeast strains. Among these three leading candidates, the order of preference in terms of both scope and potency for the N-aryl groups in these bishydrazones would be as follows: para-fluorophenyl>para-methoxyphenyl>para-chloro. With respect to certain candidates, the order of preference among the biphenyl platforms and the R substituent (FIG. 2) would be as follows: for para-fluorophenyl: 4,4', $CH_3$ (series c)>3, 4', H (series a)≈4,4', H (series b); for para-methoxyphenyl: 3,4', H (series a)≈4,4', H (series b)>4,4', $CH_3$ (series c); and for para-chlorophenyl: 3,4', H (series a)>>4,4', H (series b)>4,4', $CH_3$ (series c).

Although scope and potency represent important criteria in the development of new antifungal agents, other factors crucial to the progression of these agents were also examined. In a study of the effect of these bishydrazones on the hemolysis of mRBCs, a lack of hemolytic activity of N,N'-diaryl-bishydrazones 7a,b, 12a,b, 15a,b, 17a-c, and 20a and N,N'-diamidino-bishydrazone 24a (Table 3) was observed in comparison with the FDA-approved drug VOR (83% and 100% lysis of mRBCs at 31.3 µg/mL and 62.5 µg/mL, respectively). A time-kill assay over a 24-hour period using 4,4'-bis((E)-1-(2-(4-fluorophenyl)hydrazono)ethyl)-1,1'-biphenyl (17c) and VOR against fungal strains *C. albicans* ATCC 10231 (A) and *C. albicans* ATCC 64124 (B) (FIGS. 5A-D) indicated that bishydrazone 17c was more fungistatic than the control drug VOR at the same concentrations or even at reduced concentrations. Finally, drug candidates must avoid hERG activation to progress toward Investigational New Drug (IND) status, and using a dofetilide binding assay, it was found that N,N'-diaryl-bishydrazones 15a,b and 17a,b possessed the desired property of not inhibiting the human hERG potassium ion channel using a [$^3$H]-dofetilide binding assay to evaluate the interaction of a subset of these bishydrazones with hERG. In summary, N,N'-diaryl-bishydrazones display promise as a new family of systemic antifungal agents, and additional studies of these agents will be reported in due course.

Example 2

This Example describes the detailed synthesis of various compounds disclosed herein.

Materials and Instrumentation.

All the chemicals used in this study were purchased from Sigma-Aldrich (St. Louis, MO), AK Scientific (Union City, CA), Acros Organics (New Jersey, US), TCI America (Portland, OR), Oakwood Chemicals (Estill, SC), Combi-Blocks (San Diego, CA), Accela Chembio (San Diego, CA), and Chem-Impex (Wood Dale, IL), and used without any further purification. Chemical reactions were monitored by TLC (Merck, Silica gel 60 F254) and visualization was achieved using UV light. Compounds were purified by $SiO_2$ flash chromatography (Dynamic Adsorbents Inc., Flash $SiO_2$ gel 32-63μ) or by filtration of pure solids. $^1$H and $^{13}$C NMR spectra were recorded on Varian 400 MHz or 500 MHz spectrometers. All reactions were carried out under nitrogen atmosphere and all yields reported represent isolated yields. After synthesizing compounds 8a,b, 9a,b, 11a,b, and 14a, the compounds were found to be insoluble and therefore were not included in any of the biological assays performed in this study.

Preparation of Compounds 7a-24c

Preparation of Compound 7a

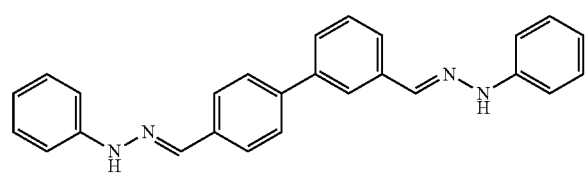 [SMILES: C(=N\Nc1ccccc1)/c1ccc(-c2cccc(/C=N/Nc3ccccc3)c2)cc1]

Figure 7:
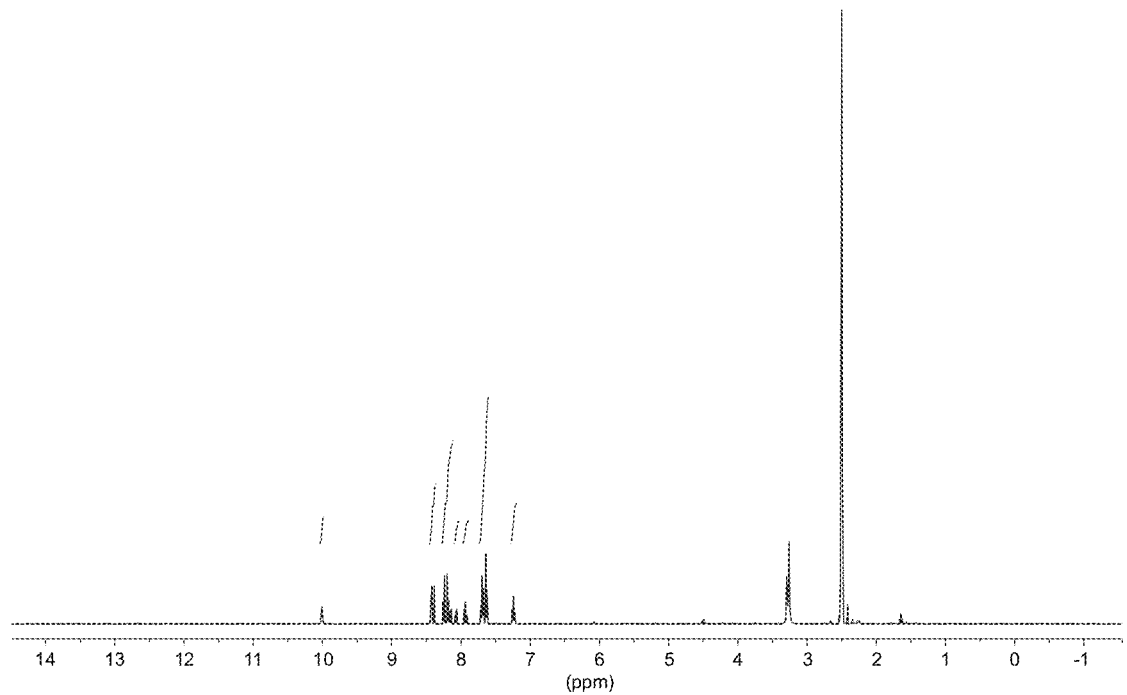
FIG. 7 shows a graph illustrating $^1$H NMR spectrum for compound 7a in $(CD_3)_2SO$ (400 MHz).
Figure 8:
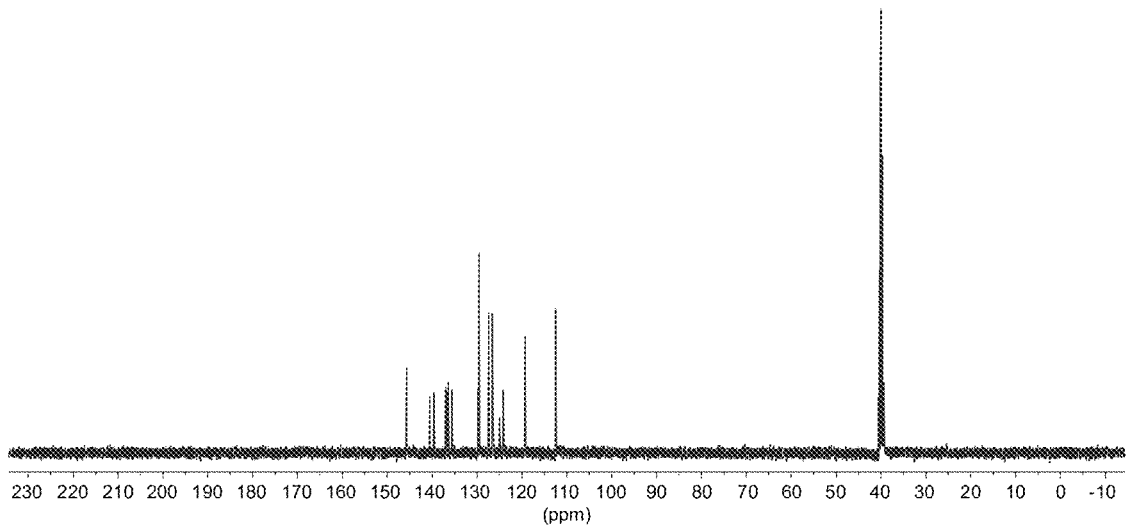
FIG. 8 shows a graph illustrating $^{13}$C NMR spectrum for compound 7a in $(CD_3)_2SO$ (100 MHz).

To a solution of [1,1'-biphenyl]-3,4'-dicarbaldehyde (210 mg, 1 mmol) in EtOH (10 mL), phenylhydrazine (0.30 mL, 3 mmol) and a catalytic amount of concentrated HCl (0.04 mL) were added. The reaction mixture was stirred at 90° C. for 1 h and the resulting solution was filtered. The residue obtained was washed with $CH_2Cl_2$ (5 mL), EtOAc (5 mL), MeOH (5 mL), and hot EtOH (5 mL) to afford compound 7a (390 mg, quantitative yield) as yellow solid: $^1$H NMR (400 MHz, $(CD_3)_2SO$, FIG. 7) δ 10.02 (s, 1H), 10.01 (s, 1H), 8.43 (s, 1H), 8.42 (s, 1H), 8.39 (s, 1H), 8.25 (d, J=8.4 Hz, 2H), 8.20 (d, J=8.8 Hz, 2H), 8.15 (d, J=8.0 Hz, 1H), 8.07 (d, J=8.0 Hz, 1H), 7.94 (t, J=8.0 Hz, 1H), 7.70 (t, J=7.6 Hz, 2H), 7.69 (t, J=7.6 Hz, 2H), 7.63 (d, J=7.6 Hz, 2H), 7.25 (d, J=6.8 Hz, 1H), 7.24 (d, J=6.8 Hz, 1H); $^{13}$C NMR (100 MHz, $(CD_3)_2SO$, FIG. 8) δ 145.2, 140.1, 139.2, 136.6, 136.2, 136.0, 135.2, 129.3, 129.2, 127.0, 126.2, 126.0, 124.6, 123.8, 118.8, 112.1, 112.0.

Preparation of Compound 7b

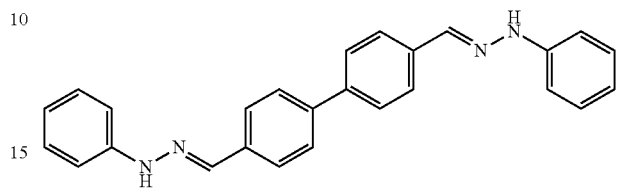

Figure 9:
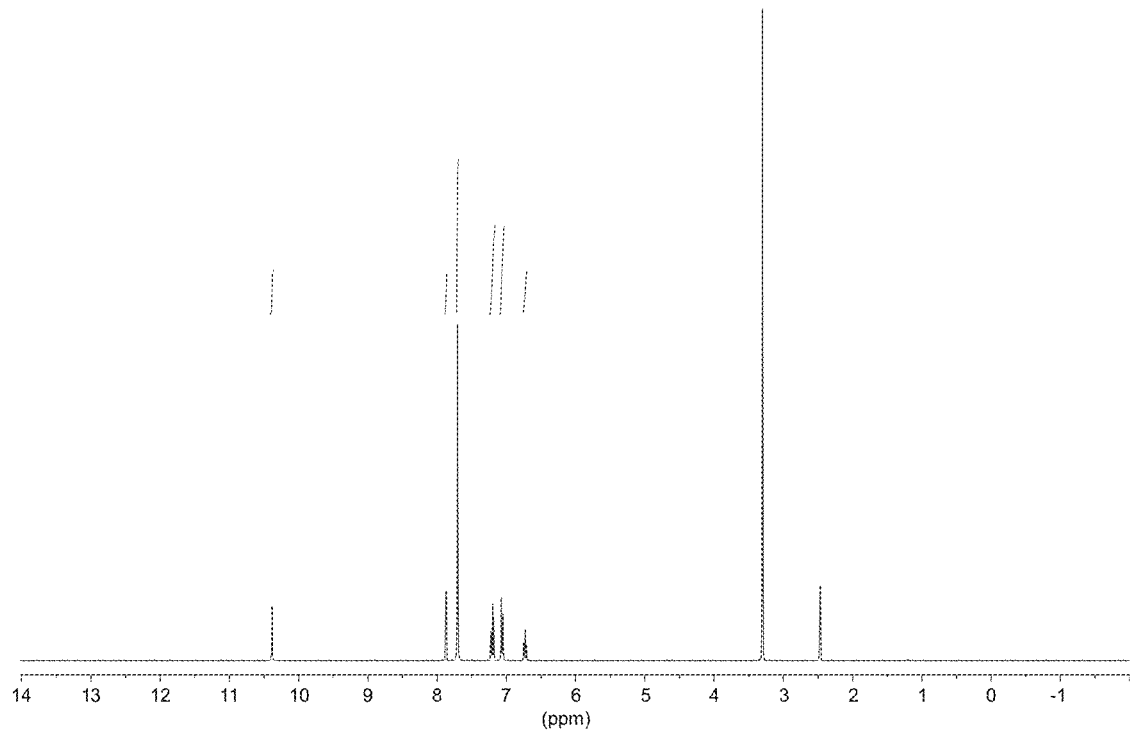
FIG. 9 shows a graph illustrating $^1$H NMR spectrum for compound 7b in $(CD_3)_2SO$ (400 MHz).
Figure 10:
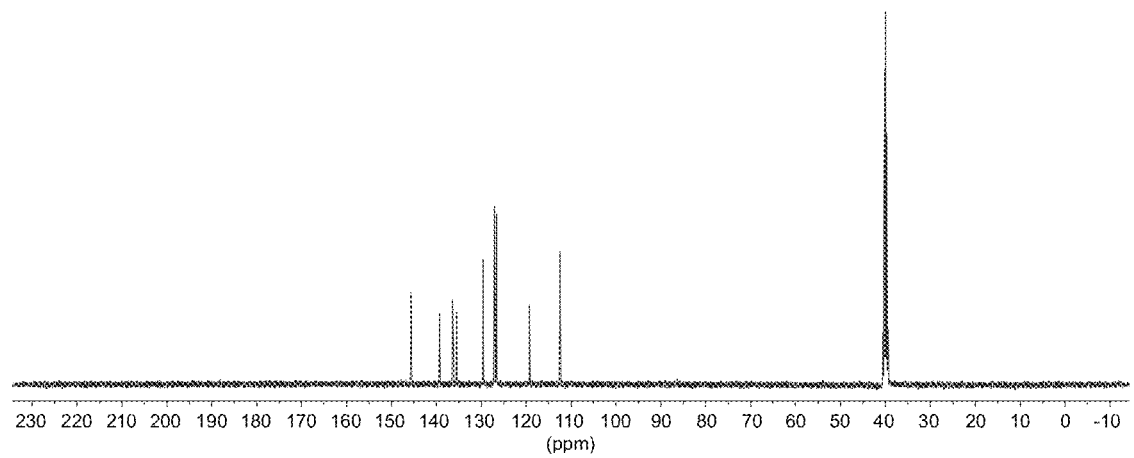
FIG. 10 shows a graph illustrating $^{13}$C NMR spectrum for compound 7b in $(CD_3)_2SO$ (100 MHz).

To a solution of [1,1'-biphenyl]-4,4'-dicarboxaldehyde (250 mg, 1.19 mmol) in EtOH (10 mL), phenylhydrazine (385 mg, 3.57 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 7b (350 mg, 75%) as yellow solid: $^1$H NMR (400 MHz, $(CD_3)_2SO$, FIG. 9) δ 10.38 (s, 2H), 7.87 (s, 2H), 7.71 (br s, 8H), 7.20 (t, J=8.4 Hz, 4H), 7.07 (d, J=7.3 Hz, 4H), 6.73 (t, J=7.3 Hz, 2H); $^{13}$C NMR (100 MHz, $(CD_3)_2SO$, FIG. 10) δ 145.6, 139.2, 136.4, 135.5, 129.6, 127.1, 126.6, 119.3, 112.5.

Preparation of Compound 8a

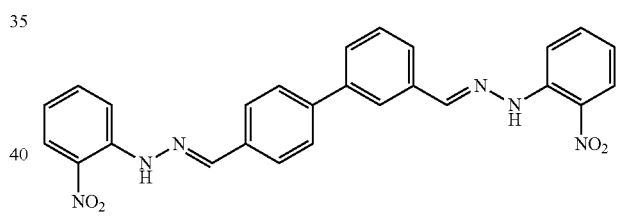

To a solution of [1,1'-biphenyl]-3,4'-dicarboxaldehyde (40 mg, 0.19 mmol) in EtOH (3 mL), 2-nitrophenylhydrazine hydrochloride (87 mg, 0.57 mmol) and a catalytic amount of concentrated HCl (0.04 mL) were added. The reaction mixture was stirred at 80° C. for 30 min and the resulting solution quenched with $H_2O$ (20 mL) and filtered. The residue obtained was washed with hot EtOH (20 mL) to afford compound 8a (45 mg, 49%) as a yellow solid, which was insoluble.

Preparation of Compound 8b

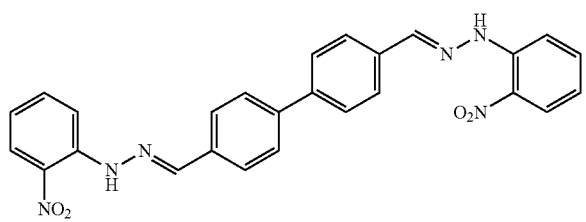 [SMILES: O=[N+]([O-])c1ccccc1N/N=C/c1ccc(-c2ccc(/C=N/Nc3ccccc3[N+](=O)[O-])cc2)cc1]

To a solution of [1,1'-biphenyl]-4,4'-dicarboxaldehyde (100 mg, 0.48 mmol) in EtOH (8 mL), 2-nitrophenylhydrazine hydrochloride (218 mg, 1.43 mmol) and a catalytic amount of concentrated HCl (0.04 mL) were added. The reaction mixture was stirred at 80° C. for 30 min and the resulting solution was filtered. The residue obtained was washed with hot EtOH (20 mL) to afford compound 8b (156 mg, 68%) as an orange solid, which was insoluble.

Preparation of Compound 9a

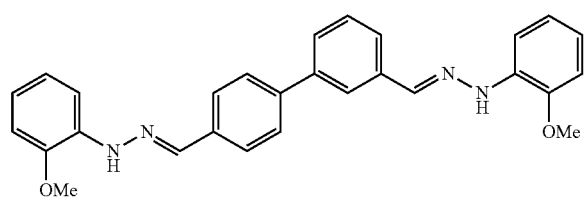 [SMILES: COc1ccccc1N/N=C/c1ccc(-c2cccc(/C=N/Nc3ccccc3OC)c2)cc1]

To a solution of [1,1'-biphenyl]-3,4'-dicarboxaldehyde (50 mg, 0.24 mmol) in EtOH (3 mL), 2-methoxyphenylhydrazine hydrochloride (104 mg, 0.59 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 9a (68 mg, 63%) as a brown solid, which was insoluble.

Preparation of Compound 9b

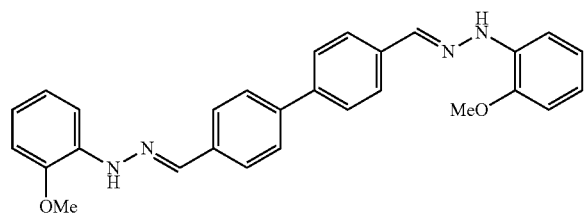 [SMILES: COc1ccccc1N/N=C/c1ccc(-c2ccc(/C=N/Nc3ccccc3OC)cc2)cc1]

To a solution of [1,1'-biphenyl]-4,4'-dicarboxaldehyde (80 mg, 0.38 mmol) in EtOH (4 mL), 2-methoxyphenylhydrazine hydrochloride (166 mg, 0.95 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 9b (118 mg, 69%) as a brown solid, which was insoluble.

Preparation of Compound 9c

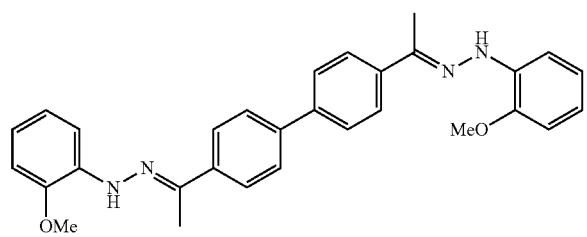 [SMILES: COc1ccccc1N/N=C(\C)c1ccc(-c2ccc(/C(C)=N/Nc3ccccc3OC)cc2)cc1]

Figure 11:
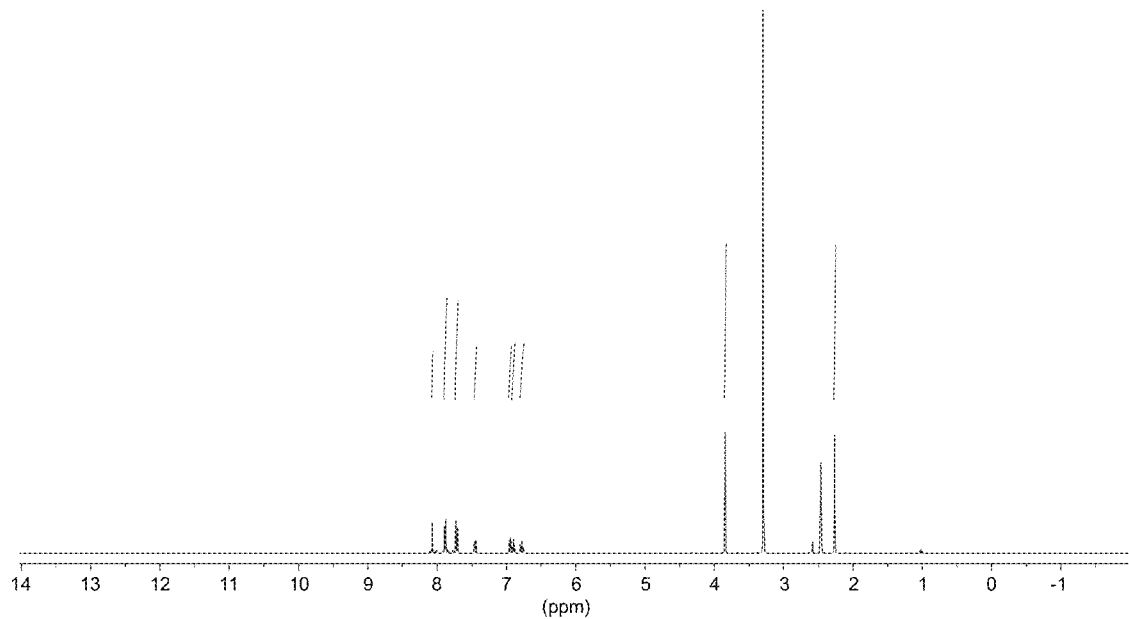
FIG. 11 shows a graph illustrating $^1$H NMR spectrum for compound 9c in $(CD_3)_2SO$ (400 MHz).
Figure 12:
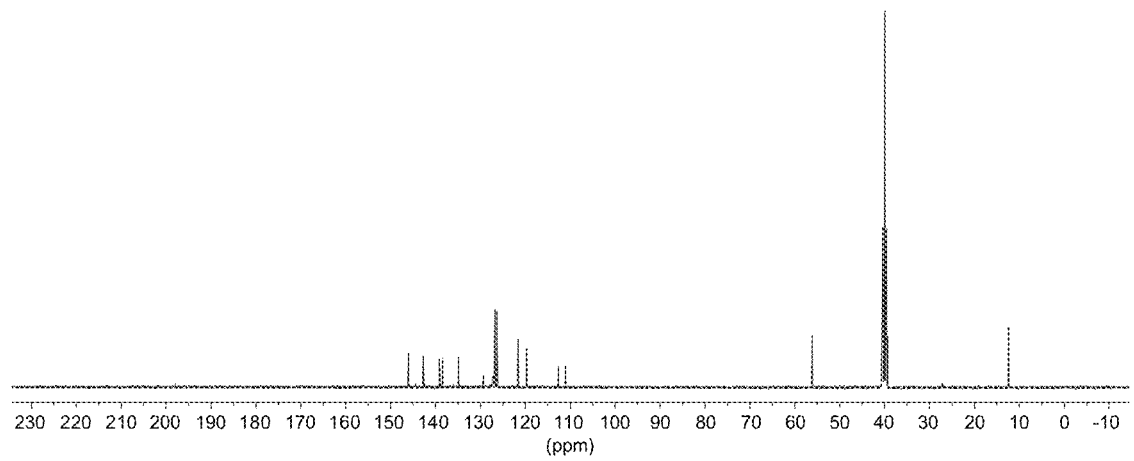
FIG. 12 shows a graph illustrating $^{13}$C NMR spectrum for compound 9c in $(CD_3)_2SO$ (100 MHz).

To a solution of 4,4'-diacetylbiphenyl (50 mg, 0.21 mmol) in EtOH (3 mL), 2-methoxyphenylhydrazine hydrochloride (92 mg, 0.52 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 9c (58 mg, 58%) as a yellow solid: $^1$H NMR (400 MHz, (CD$_3$)$_2$SO, FIG. 11) δ 8.07 (s, 2H), 7.88 (d, J=8.6 Hz, 4H), 7.72 (d, J=8.6 Hz, 4H), 7.44 (dd, J$_1$=7.8 Hz, J$_2$=1.6 Hz, 2H), 6.95 (dd, J$_1$=8.0 Hz, J$_2$=1.3 Hz, 2H), 6.90 (td, J$_1$=7.7 Hz, J$_2$=1.3 Hz, 2H), 6.77 (dd, J$_1$=7.7 Hz, J$_2$=1.6 Hz, 2H), 3.84 (s, 6H), 2.26 (s, 6H); $^{13}$C NMR (100 MHz, (CD$_3$)$_2$SO, FIG. 12) δ 146.0, 142.7, 139.1. 138.4, 134.9, 126.8, 126.3, 121.6, 119.7, 112.7, 111.1, 56.1, 12.4.

Preparation of Compound 10a

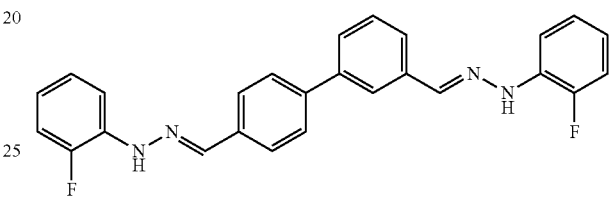

Figure 13:
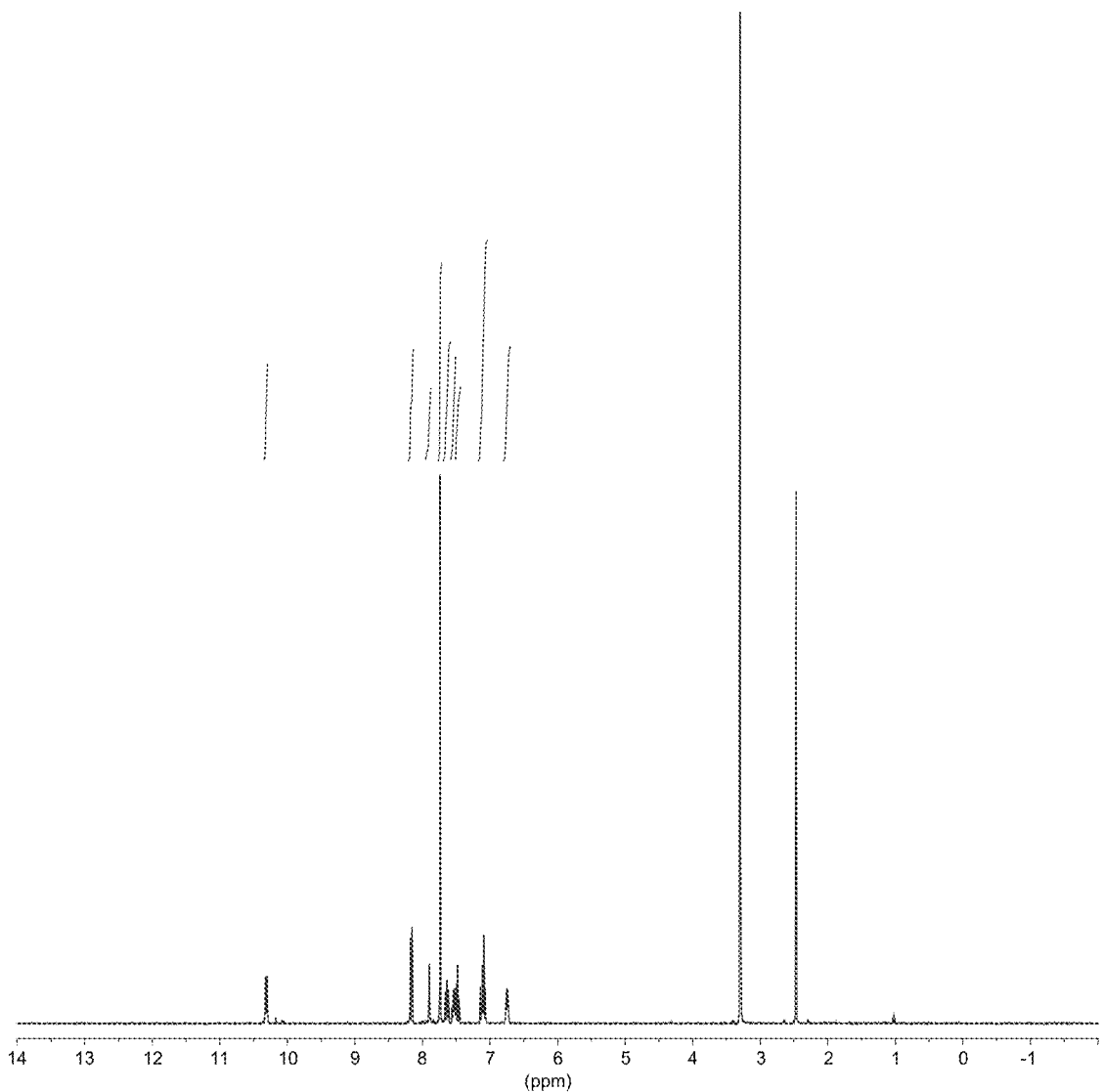
FIG. 13 shows a graph illustrating $^1$H NMR spectrum for compound 10a in $(CD_3)_2SO$ (400 MHz).
Figure 14:
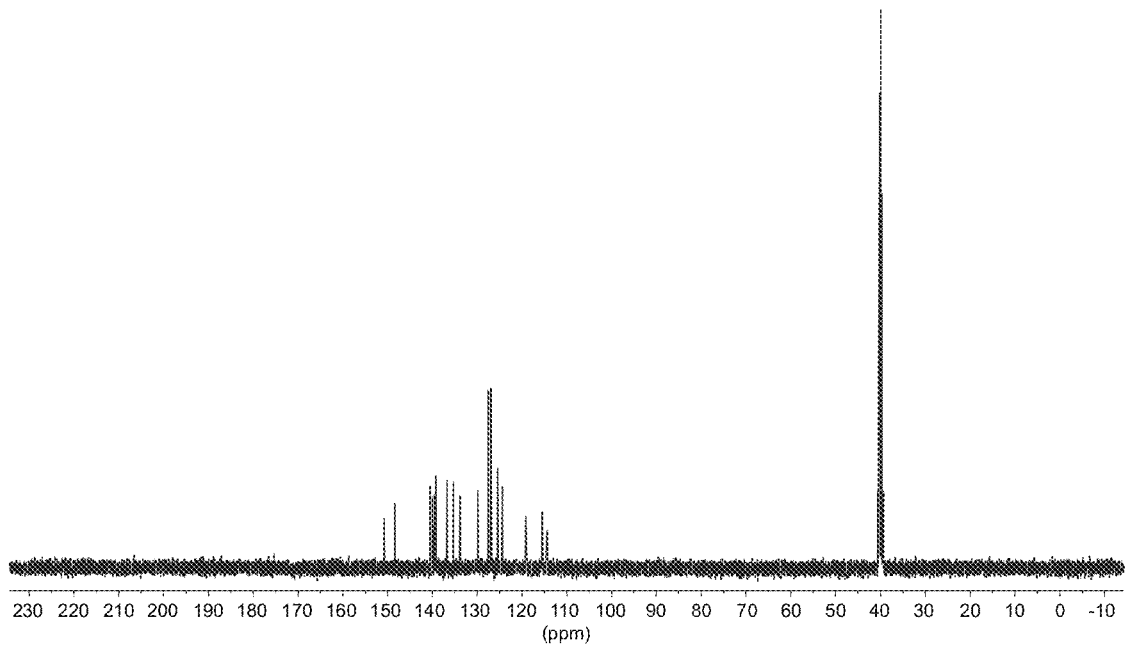
FIG. 14 shows a graph illustrating $^{13}$C NMR spectrum for compound 10a in $(CD_3)_2SO$ (100 MHz).

To a solution of [1,1'-biphenyl]-3,4'-dicarbaldehyde (210 mg, 1 mmol) in EtOH (20 mL), 2-fluorophenylhydrazine hydrochloride (480 mg, 3 mmol) and a catalytic amount of concentrated HCl (0.04 mL) were added. The reaction mixture was stirred at 90° C. for 1 h and the resulting solution was filtered. The residue obtained was washed with 2 N HCl (20 mL) and hot EtOH (20 mL) to afford compound 10a (225 mg, 53%) as a yellow solid: $^1$H NMR (400 MHz, (CD$_3$)$_2$SO, FIG. 13) δ 10.04 (s, 1H), 10.03 (s, 1H), 8.21 (s, 1H), 8.19 (s, 1H), 7.93 (s, 1H), 7.80-7.74 (m, 4H), 7.67 (t, J=9.6 Hz, 2H), 7.59-7.54 (m, 2H), 7.51 (t, J=8.0 Hz, 1H), 7.17 (d, J=8.4 Hz, 2H), 7.12 (t, J=8.4 Hz, 2H), 6.81-6.75 (m, 2H); $^{13}$C NMR (100 MHz, (CD$_3$)$_2$SO, FIG. 14) δ 150.3, 147.9 140.1, 139.6, 139.1, 138.8, 136.3, 134.9, 133.4, 133.3, 129.4, 127.1, 126.55, 126.47, 125.04, 125.01, 124.0, 118.73, 118.66, 115.1, 115.0, 114.0, 113.9.

Preparation of Compound 10b

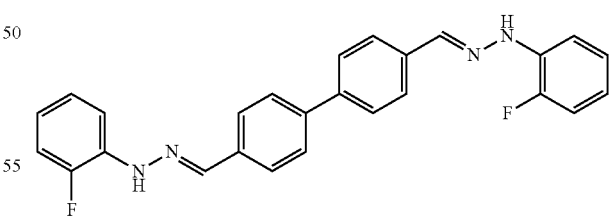

Figure 15:
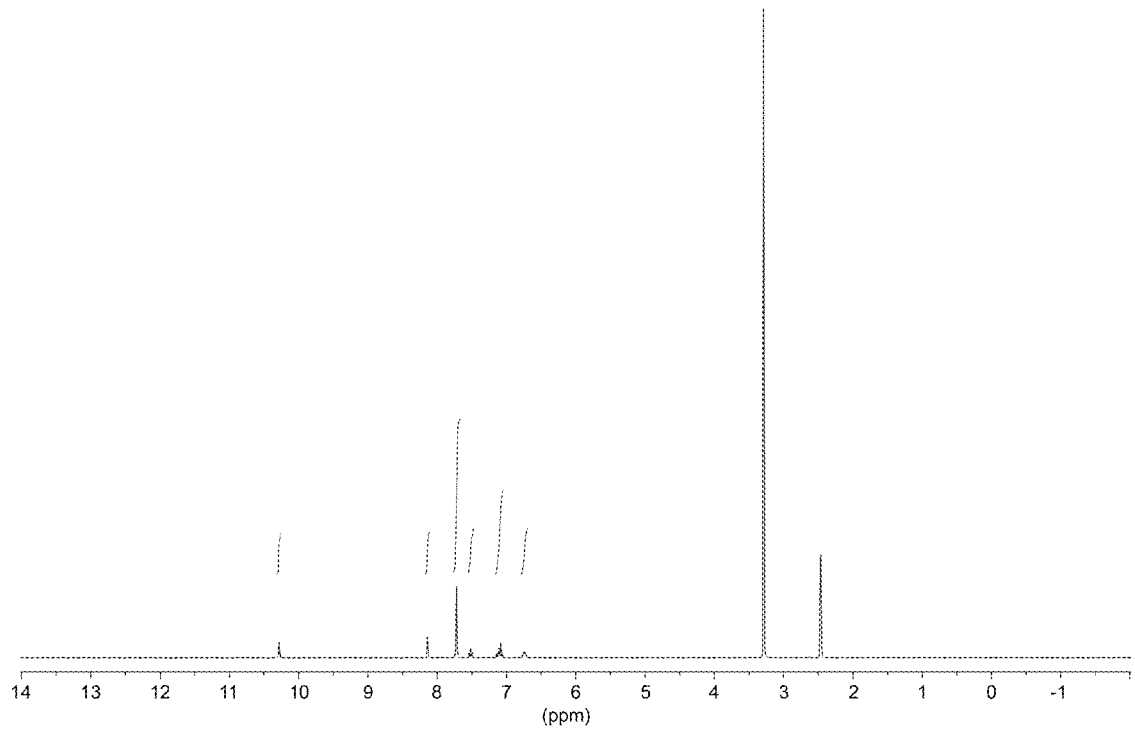
FIG. 15 shows a graph illustrating $^1$H NMR spectrum for compound 10b in $(CD_3)_2SO$ (400 MHz).

To a solution of [1,1'-biphenyl]-4,4'-dicarboxaldehyde (100 mg, 0.48 mmol) in EtOH (8 mL), 2-fluorophenylhydrazine hydrochloride (232 mg, 1.43 mmol) and a catalytic amount of concentrated HCl (0.04 mL) were added. The reaction mixture was stirred at 80° C. for 30 min and the resulting solution was filtered. The residue obtained was washed with hot EtOH (20 mL) to afford compound 10b (92 mg, 45%) as a yellow solid: $^1$H NMR (400 MHz, (CD$_3$)$_2$SO, FIG. 15) δ 10.29 (s, 2H), 8.14 (s, 2H), 7.72 (br s, 8H), 7.51

Figure 16:
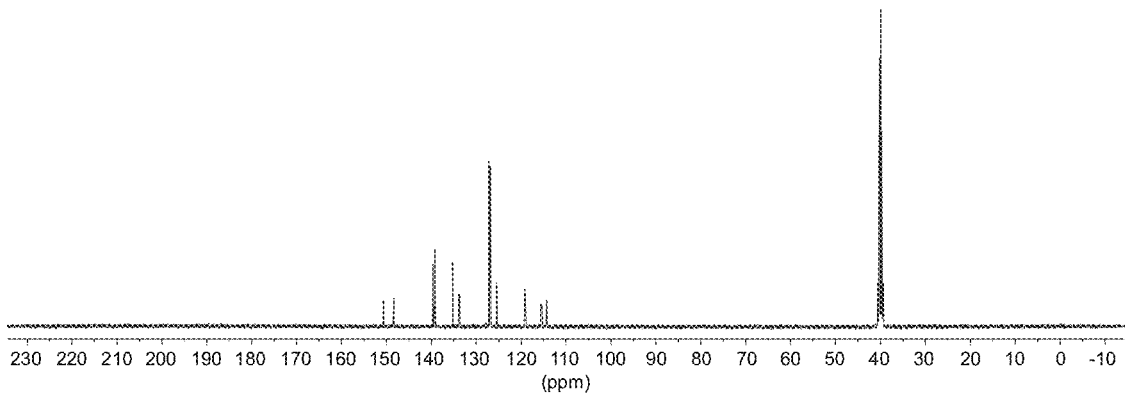
FIG. 16 shows a graph illustrating $^{13}$C NMR spectrum for compound 10b in $(CD_3)_2SO$ (100 MHz).

(t, J=8.8 Hz, 2H), 7.12 (d, J=7.8 Hz, 2H), 7.09 (t, J=8.0 Hz, 2H), 6.74 (m, 2H); $^{13}$C NMR (100 MHz, (CD$_3$)$_2$SO, FIG. 16) δ 150.7, 148.3, 139.6, 139.2, 135.2, 133.8, 133.7, 127.2, 126.9, 125.5, 125.4, 119.15, 119.08, 115.6, 115.4, 114.33, 114.29.

Preparation of Compound 11a

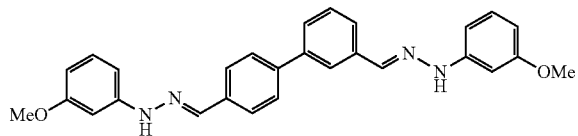 [SMILES: COc1cccc(N/N=C/c2ccc(-c3cccc(/C=N/Nc4cccc(OC)c4)c3)cc2)c1]

To a solution of [1,1'-biphenyl]-3,4'-dicarboxaldehyde (50 mg, 0.24 mmol) in EtOH (3 mL), 3-methoxyphenylhydrazine hydrochloride (104 mg, 0.59 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 11a (85 mg, 79%) as a brown solid, which was insoluble.

Preparation of Compound 11b

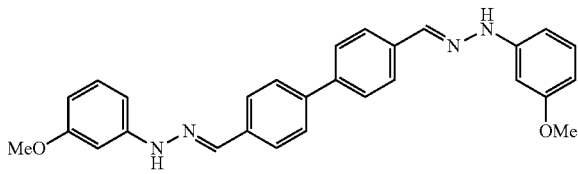 [SMILES: COc1cccc(N/N=C/c2ccc(-c3ccc(/C=N/Nc4cccc(OC)c4)cc3)cc2)c1]

To a solution of [1,1'-biphenyl]-4,4'-dicarboxaldehyde (80 mg, 0.38 mmol) in EtOH (4 mL), 3-methoxyphenylhydrazine hydrochloride (166 mg, 0.95 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 11b (128 mg, 75%) as a brown solid, which was insoluble.

Preparation of Compound 11c

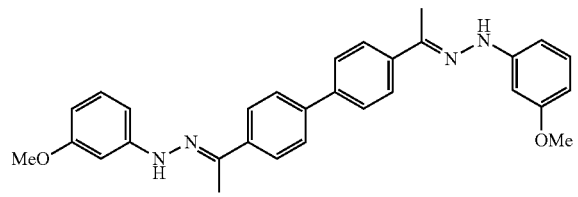 [SMILES: COc1cccc(N/N=C(\C)c2ccc(-c3ccc(/C(C)=N/Nc4cccc(OC)c4)cc3)cc2)c1]

Figure 17:
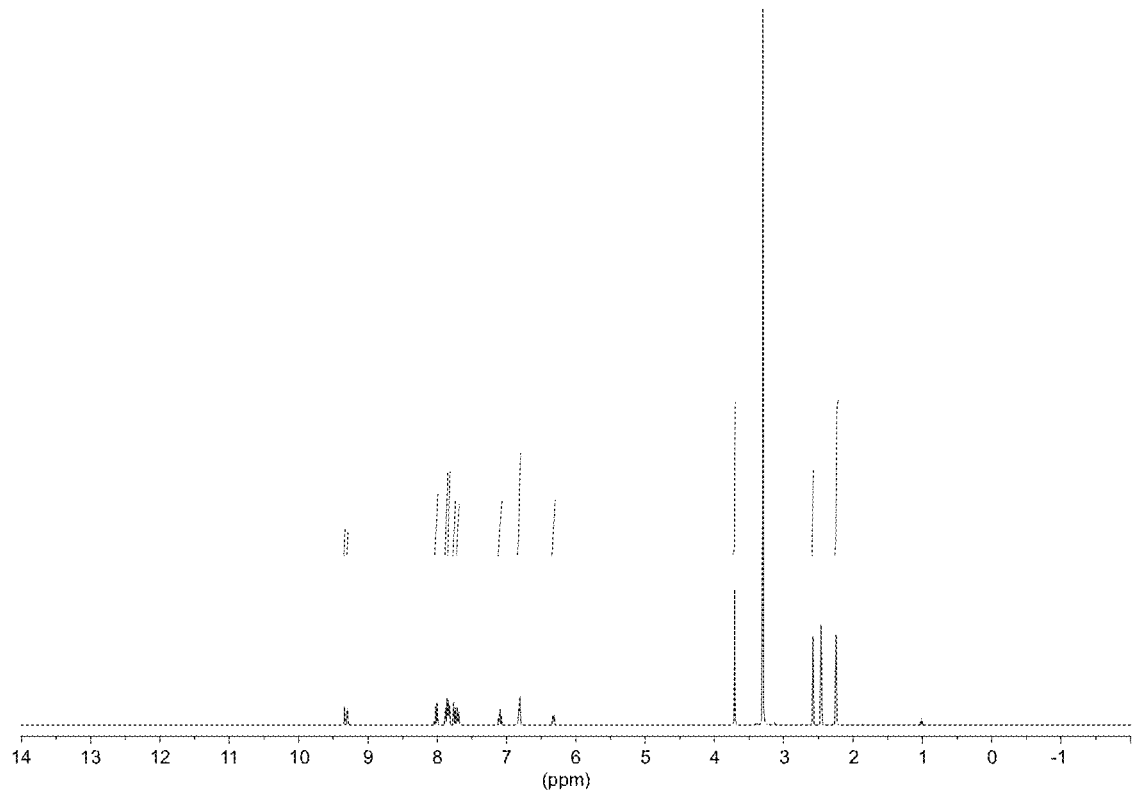
FIG. 17 shows a graph illustrating $^1$H NMR spectrum for compound 11c in $(CD_3)_2SO$ (400 MHz).
Figure 18:
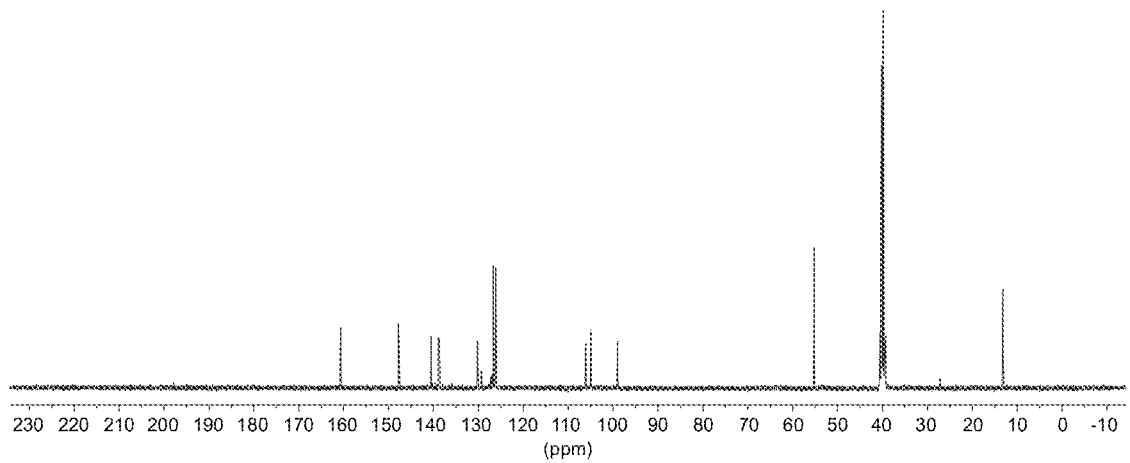
FIG. 18 shows a graph illustrating $^{13}$C NMR spectrum for compound 11c in $(CD_3)_2SO$ (100 MHz).

To a solution of 4,4'-diacetylbiphenyl (100 mg, 0.42 mmol) in EtOH (5 mL), 3-methoxyphenylhydrazine hydrochloride (183 mg, 1.45 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 11c (94 mg, 47%) as a yellow solid: $^1$HNMR (400 MHz, (CD$_3$)$_2$SO, FIG. 17) δ 9.30 (s, 2H), 7.84 (d, J=8.3 Hz, 4H), 7.70 (d, J=8.6 Hz, 4H), 7.09 (t, J=8.3 Hz, 2H), 6.84-6.78 (m, 4H), 6.32 (ddd, J$_1$=8.1 Hz, J$_2$=2.4 Hz, J$_3$=1.1 Hz, 2H), 3.71 (s, 6H), 2.24 (s, 6H); $^{13}$C NMR (100 MHz, (CD$_3$)$_2$SO, FIG. 18) δ 160.6, 147.7, 140.5, 138.9, 138.7, 130.2, 126.7, 126.1, 106.1, 104.9, 99.0, 55.2, 13.2.

Preparation of Compound 12a

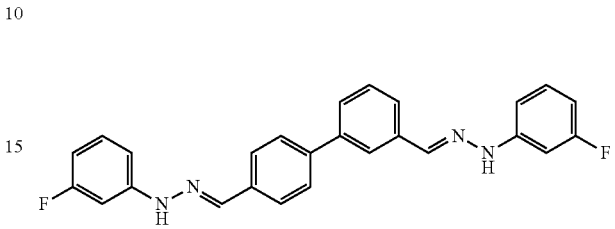

Figure 19:
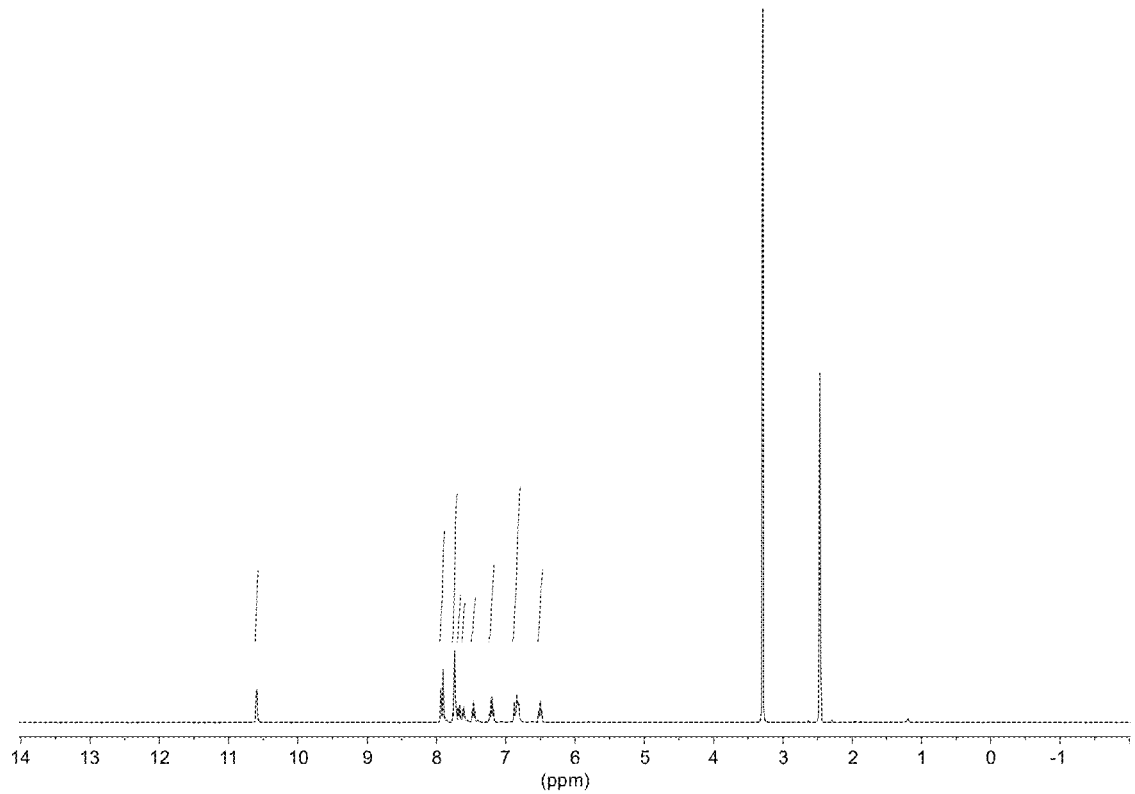
FIG. 19 shows a graph illustrating $^1$H NMR spectrum for compound 12a in $(CD_3)_2SO$ (400 MHz).
Figure 20:
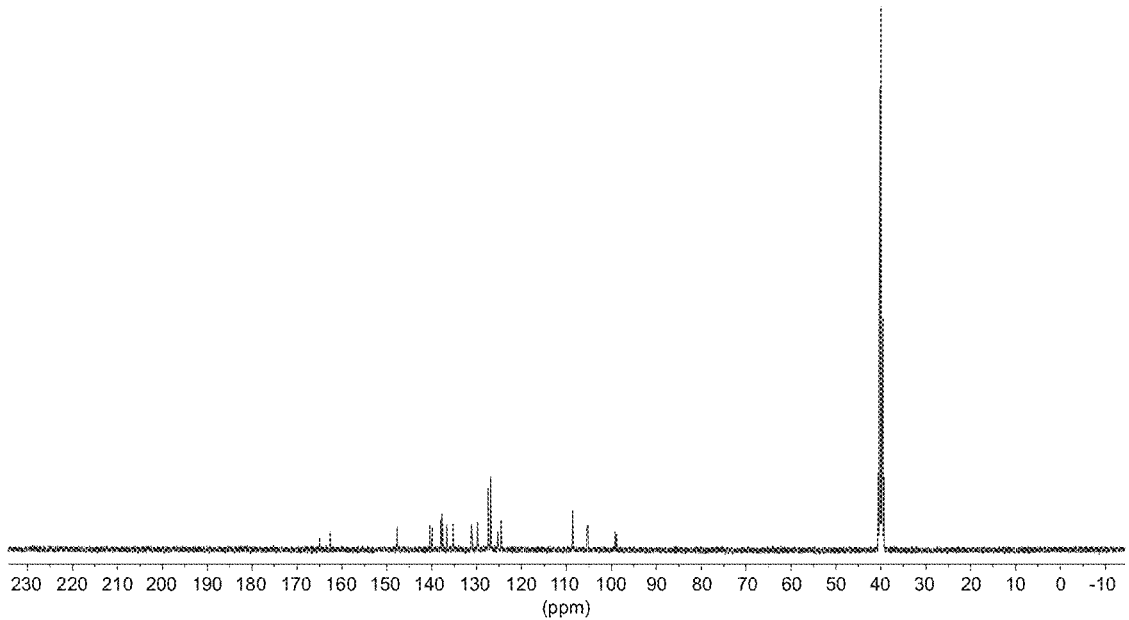
FIG. 20 shows a graph illustrating $^{13}$C NMR spectrum for compound 12a in $(CD_3)_2SO$ (100 MHz).

To a solution of [1,1'-biphenyl]-3,4'-dicarboxaldehyde (40 mg, 0.19 mmol) in EtOH (3 mL), 3-fluorophenylhydrazine hydrochloride (93 mg, 0.57 mmol) and a catalytic amount of concentrated HCl (0.04 mL) were added. The reaction mixture was stirred at 80° C. for 30 min and the resulting solution quenched with H$_2$O (20 mL) and filtered. The residue obtained was washed with hot EtOH (20 mL) to afford compound 12a (39 mg, 48%) as a yellow solid: $^1$H NMR (400 MHz, (CD$_3$)$_2$SO, FIG. 19) δ 10.60 (s, 1H), 10.59 (s, 1H), 7.92 (m, 3H), 7.73 (m, 4H), 7.67 (d, J=7.7 Hz, 1H), 7.61 (d, J=8.2 Hz, 1H), 7.46 (t, J=7.7 Hz, 1H), 7.22 (d, J=7.7 Hz, 1H), 7.18 (d, J=7.7 Hz, 1H), 6.90-6.78 (m, 4H), 6.50 (td, J$_1$=8.5 Hz, J$_1$=2.6 Hz, 2H); $^{13}$C NMR (100 MHz, (CD$_3$)$_2$SO, FIG. 20) δ 165.0, 162.6, 147.7, 147.6, 140.5, 139.9, 138.0, 137.7, 136.6, 135.2, 131.2, 131.1, 129.8, 127.4, 126.9, 125.3, 124.5, 108.6, 105.4, 105.2, 99.1, 98.8.

Preparation of Compound 12b

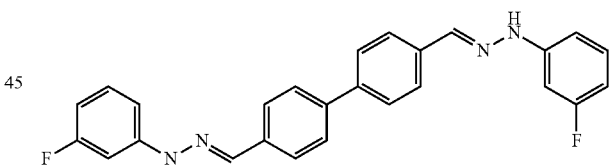

Figure 21:
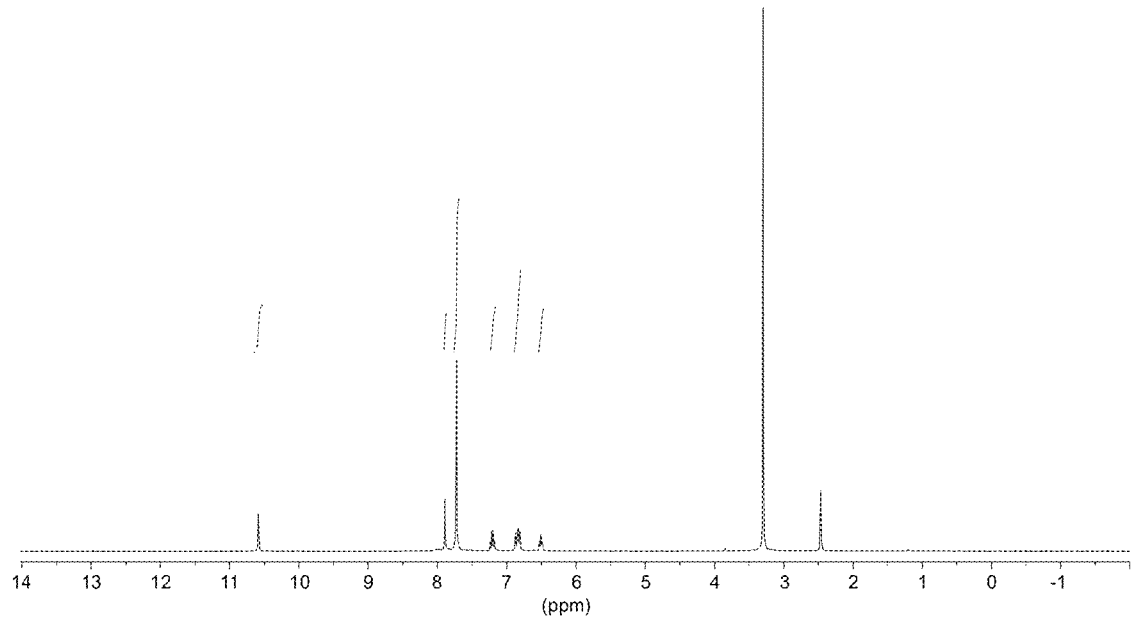
FIG. 21 shows a graph illustrating $^1$H NMR spectrum for compound 12b in $(CD_3)_2SO$ (400 MHz).
Figure 22:
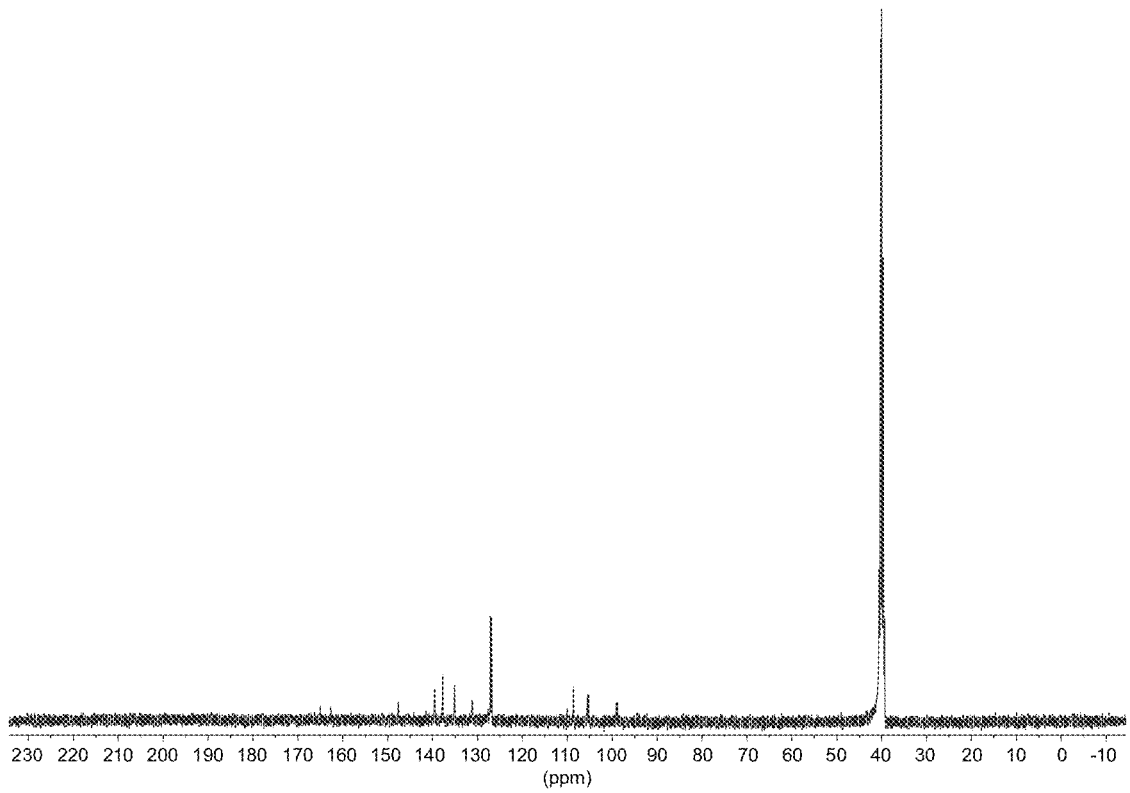
FIG. 22 shows a graph illustrating $^{13}$C NMR spectrum for compound 12b in $(CD_3)_2SO$ (100 MHz).

To a solution of [1,1'-biphenyl]-4,4'-dicarboxaldehyde (150 mg, 0.71 mmol) in EtOH (10 mL), 3-fluorophenylhydrazine hydrochloride (347 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 12b (200 mg, 66%) as a yellow solid: $^1$H NMR (400 MHz, (CD$_3$)$_2$SO, FIG. 21) δ 10.59 (s, 2H), 7.89 (s, 2H), 7.73 (m, 8H), 7.20 (td, J$_1$=11.7 Hz, J$_2$=8.2 Hz, 2H), 6.86 (dt, J$_1$=11.7 Hz, J$_2$=2.2 Hz, 2H), 6.82 (ddd, J$_1$=8.2 Hz, J$_2$=2.2 Hz, J$_3$=0.9 Hz, 2H), 6.51 (td, J$_1$=8.2 Hz, J$_2$=2.2 Hz, 2H); $^{13}$C NMR (100 MHz, (CD$_3$)$_2$SO, FIG. 22) δ 165.0, 162.6, 147.7, 147.6, 139.6, 137.7, 135.1, 131.2, 131.1, 127.1, 126.9, 108.6, 105.4, 105.2, 99.1, 98.8.

Preparation of Compound 13b

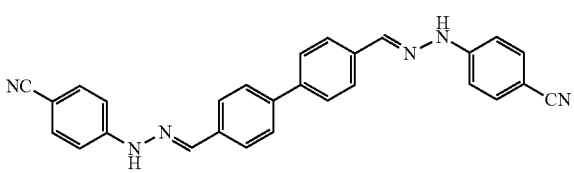 [SMILES: N#Cc1ccc(N/N=C/c2ccc(-c3ccc(/C=N/Nc4ccc(C#N)cc4)cc3)cc2)cc1]

Figure 23:
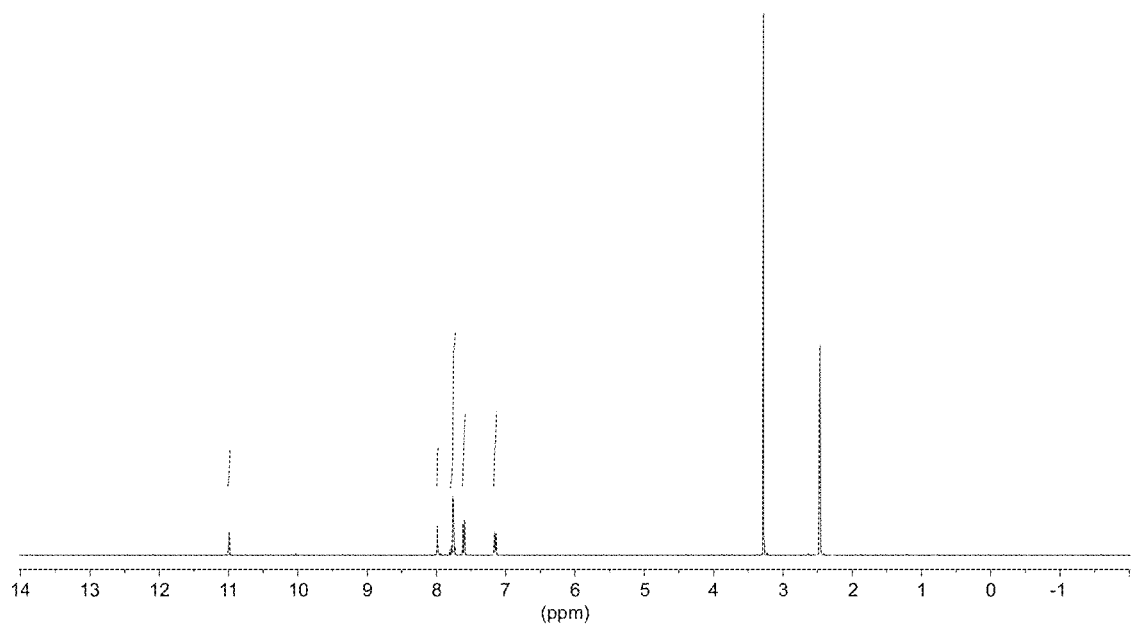
FIG. 23 shows a graph illustrating $^1$H NMR spectrum for compound 13b in $(CD_3)_2SO$ (400 MHz).
Figure 24:
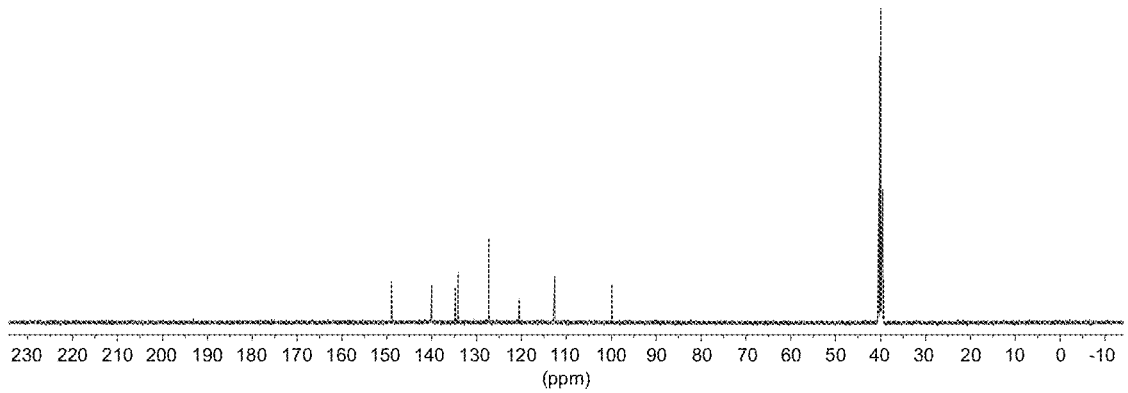
FIG. 24 shows a graph illustrating $^{13}$C NMR spectrum for compound 13b in $(CD_3)_2SO$ (100 MHz).

To a solution of [1,1'-biphenyl]-4,4'-dicarboxaldehyde (100 mg, 0.48 mmol) in EtOH (5 mL), 4-cyanophenylhydrazine hydrochloride (201 mg, 1.19 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 13b (142 mg, 67%) as a yellow solid: $^1$H NMR (400 MHz, $(CD_3)_2SO$, FIG. 23) δ 10.99 (s, 2H), 7.98 (s, 2H), 7.77 (d, J=8.8 Hz, 4H), 7.74 (d, J=8.8 Hz, 4H), 7.60 (d, J=8.8 Hz, 4H), 7.15 (d, J=8.8 Hz, 4H), $^{13}$C NMR (100 MHz, $(CD_3)_2SO$, FIG. 24) δ 149.0, 140.04, 140.00, 134.8, 134.1, 127.3, 127.2, 120.5, 112.6, 99.8.

Preparation of Compound 14a

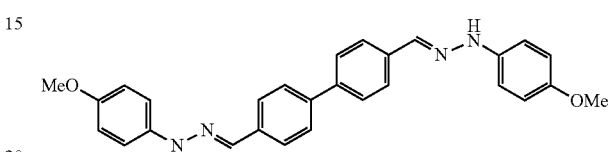

To a solution of [1,1'-biphenyl]-3,4'-dicarboxaldehyde (40 mg, 0.19 mmol) in EtOH (3 mL), 4-trifluoromethylphenylhydrazine (100 mg, 0.57 mmol) and a catalytic amount of concentrated HCl (0.04 mL) were added. The reaction mixture was stirred at 80° C. for 30 min and the resulting solution quenched with $H_2O$ (20 mL) and filtered. The residue obtained was washed with hot EtOH (20 mL) to afford compound 14a (61 mg, 60%) as a yellow solid, which was insoluble.

Preparation of Compound 15a

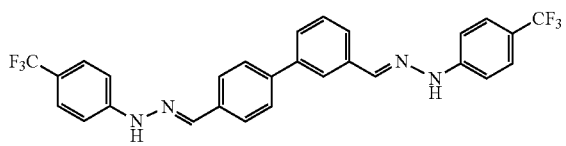 [SMILES: FC(F)(F)c1ccc(N/N=C/c2ccc(-c3cccc(/C=N/Nc4ccc(C(F)(F)F)cc4)c3)cc2)cc1]

Figure 25:
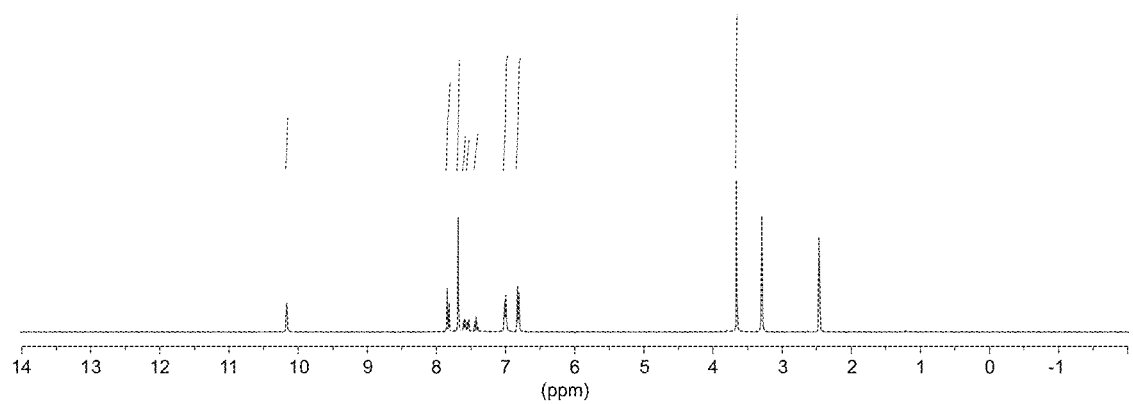
FIG. 25 shows a graph illustrating $^1$H NMR spectrum for compound 15a in $(CD_3)_2SO$ (400 MHz).
Figure 26:
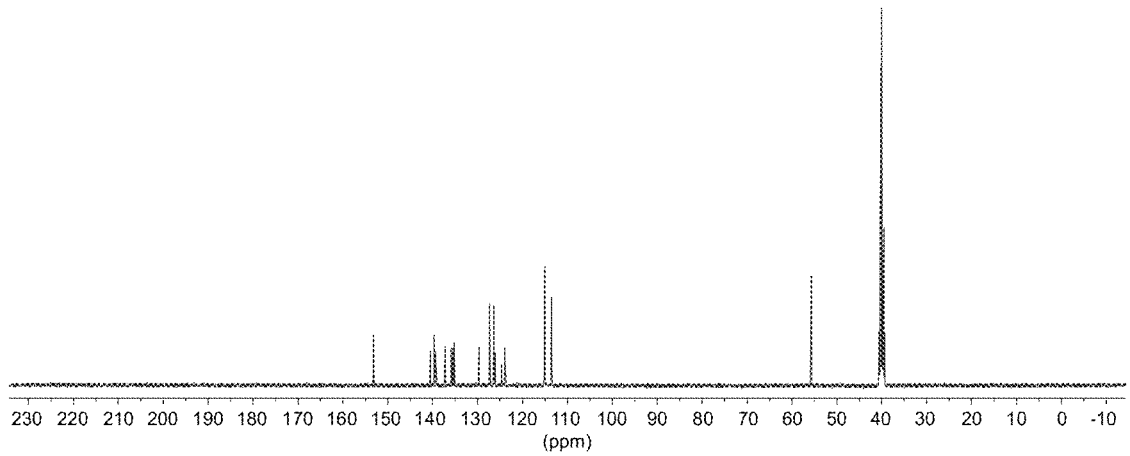
FIG. 26 shows a graph illustrating $^{13}$C NMR spectrum for compound 15a in $(CD_3)_2SO$ (100 MHz).

To a solution of [1,1'-biphenyl]-3,4'-dicarboxaldehyde (40 mg, 0.19 mmol) in EtOH (3 mL), 4-methoxyphenylhydrazine hydrochloride (99 mg, 0.57 mmol) and a catalytic amount of concentrated HCl (0.04 mL) were added. The reaction mixture was stirred at 80° C. for 30 min and the resulting solution quenched with $H_2O$ (20 mL) and filtered. The residue obtained was washed with hot EtOH (20 mL) to afford compound 15a (32 mg, 38%) as a yellow solid: $^1$H NMR (400 MHz, $(CD_3)_2SO$, FIG. 25) δ 10.16 (s, 2H), 7.85 (br s, 2H), 7.82 (m, 1H), 7.68 (m, 4H), 7.59 (d, J=7.7 Hz, 1H), 7.54 (d, J=7.4 Hz, 1H), 7.43 (t, J=7.7 Hz, 1H), 7.00 (dd, J=7.9 Hz, $J_1$=1.8 Hz, 4H), 6.82 (d, J=9.0 Hz, 4H), 3.66 (s, 6H); $^{13}$C NMR (100 MHz, $(CD_3)_2SO$, FIG. 26) δ 153.1, 140.5, 139.73, 139.71, 139.3, 137.2, 135.8, 135.5, 135.2, 129.7, 127.3, 126.4, 126.1, 124.7, 123.9, 115.1, 113.51, 113.47, 55.70, 55.69.

Preparation of Compound 15b

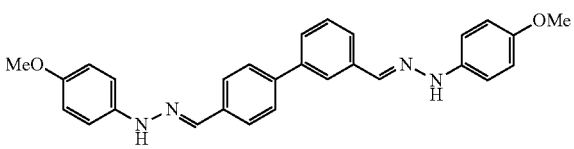 [SMILES: COc1ccc(N/N=C/c2ccc(-c3cccc(/C=N/Nc4ccc(OC)cc4)c3)cc2)cc1]

Figure 27:
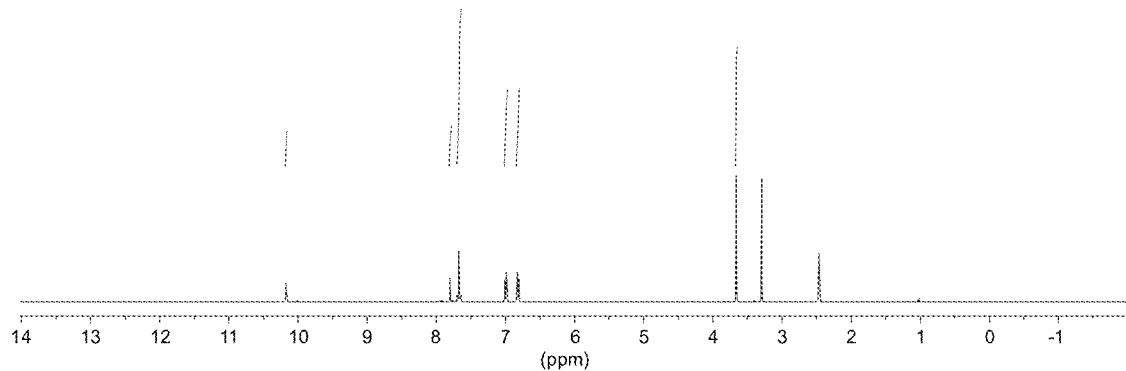
FIG. 27 shows a graph illustrating $^1$H NMR spectrum for compound 15b in $(CD_3)_2SO$ (400 MHz).
Figure 28:
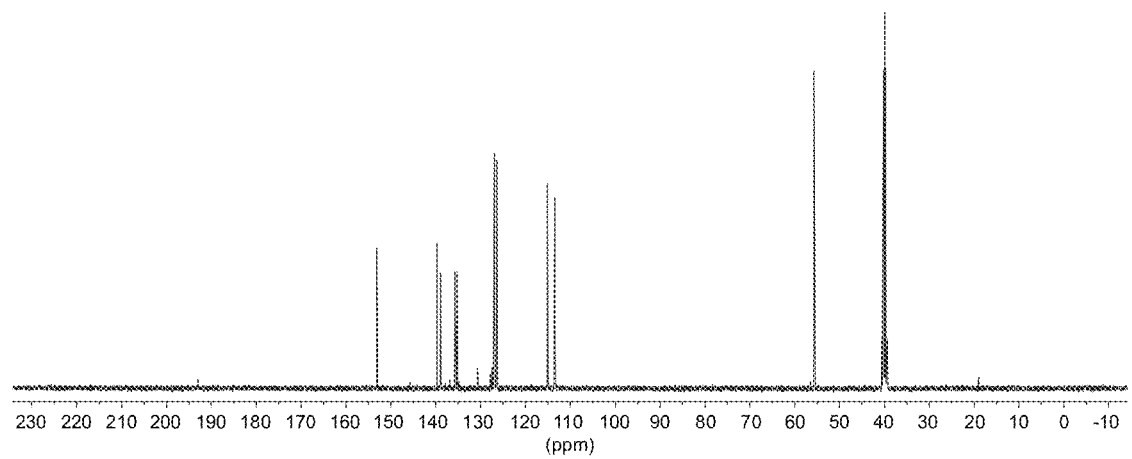
FIG. 28 shows a graph illustrating $^{13}$C NMR spectrum for compound 15b in $(CD_3)_2SO$ (100 MHz).

To a solution of [1,1'-biphenyl]-4,4'-dicarboxaldehyde (200 mg, 0.95 mmol) in EtOH (10 mL), 4-methoxyphenylhydrazine hydrochloride (415 mg, 2.38 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 15b (312 mg, 72%) as a yellow solid: $^1$H NMR (400 MHz, $(CD_3)_2SO$, FIG. 27) δ 10.17 (s, 2H), 7.80 (s, 2H), 7.69 (d, J=8.6 Hz, 4H), 7.66 (d, J=8.6 Hz, 4H), 6.99 (d, J=8.9 Hz, 4H), 6.82 (d, J=8.9 Hz, 4H), 3.66 (s, 6H); $^{13}$C NMR (100 MHz, $(CD_3)_2SO$, FIG. 28) δ 153.1, 139.7, 138.9, 135.7, 135.2, 127.0, 126.4, 115.1, 113.5, 55.7.

Preparation of Compound 15c

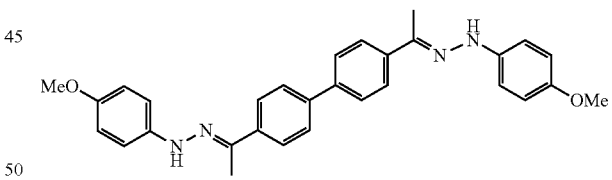

Figure 29:
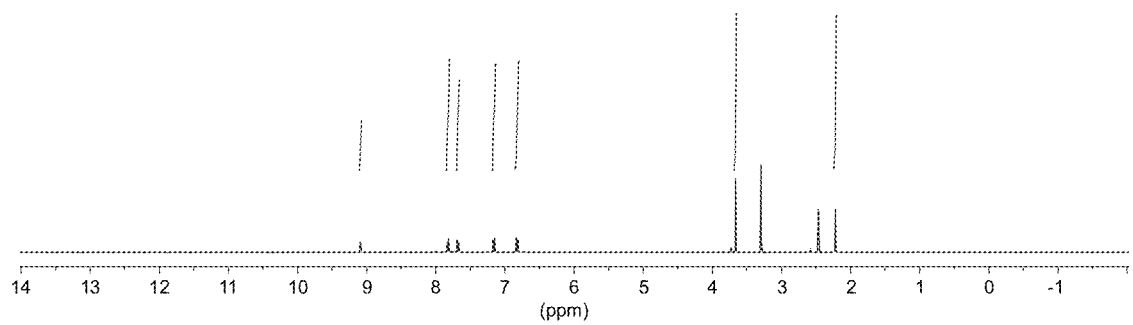
FIG. 29 shows a graph illustrating $^1$H NMR spectrum for compound 15c in $(CD_3)_2SO$ (400 MHz).
Figure 30:
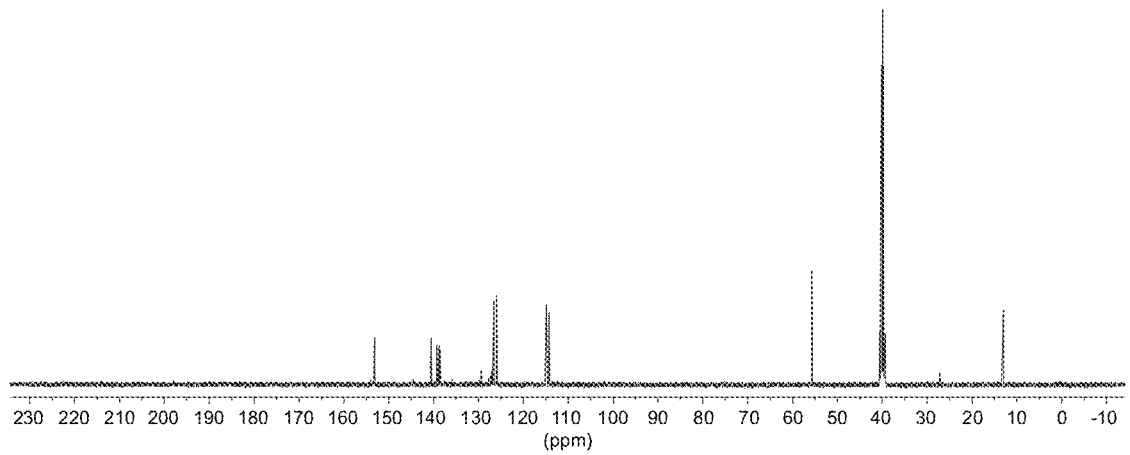
FIG. 30 shows a graph illustrating $^{13}$C NMR spectrum for compound 15c in $(CD_3)_2SO$ (100 MHz).

To a solution of 4,4'-diacetylbiphenyl (200 mg, 0.84 mmol) in EtOH (10 mL), 4-methoxyphenylhydrazine hydrochloride (366 mg, 2.09 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 15c (295 mg, 73%) as a yellow solid: $^1$H NMR (400 MHz, $(CD_3)_2SO$, FIG. 29) δ 9.09 (s, 2H), 7.82 (d, J=8.6 Hz, 4H), 7.68 (d, J=8.6 Hz, 4H), 7.16 (d, J=9.0 Hz, 4H), 6.82 (d, J=9.0 Hz, 4H), 3.67 (s, 6H), 2.22 (s, 6H); $^{13}$C NMR (100 MHz, $(CD_3)_2SO$, FIG. 30) δ 153.1, 140.5, 139.3, 138.8, 138.6, 126.6, 125.9, 114.8, 114.2, 55.7, 13.0.

Preparation of Compound 16b

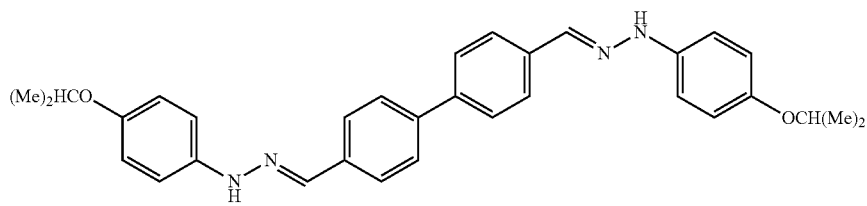

Figure 31:
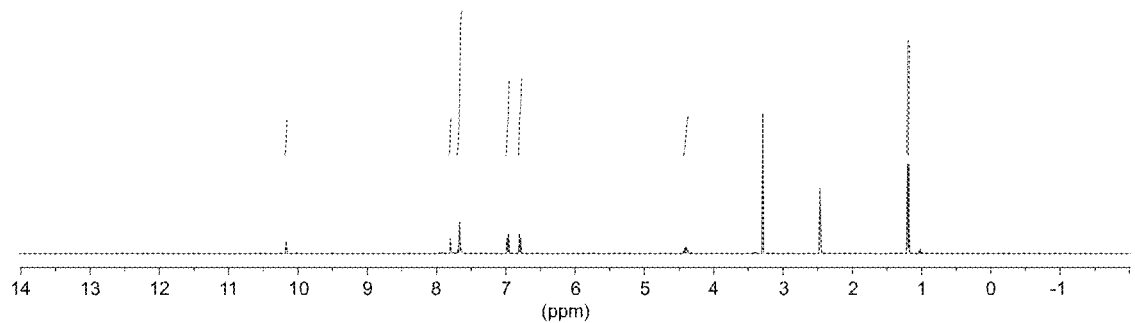
FIG. 31 shows a graph illustrating $^1$H NMR spectrum for compound 16b in $(CD_3)_2SO$ (400 MHz).
Figure 32:
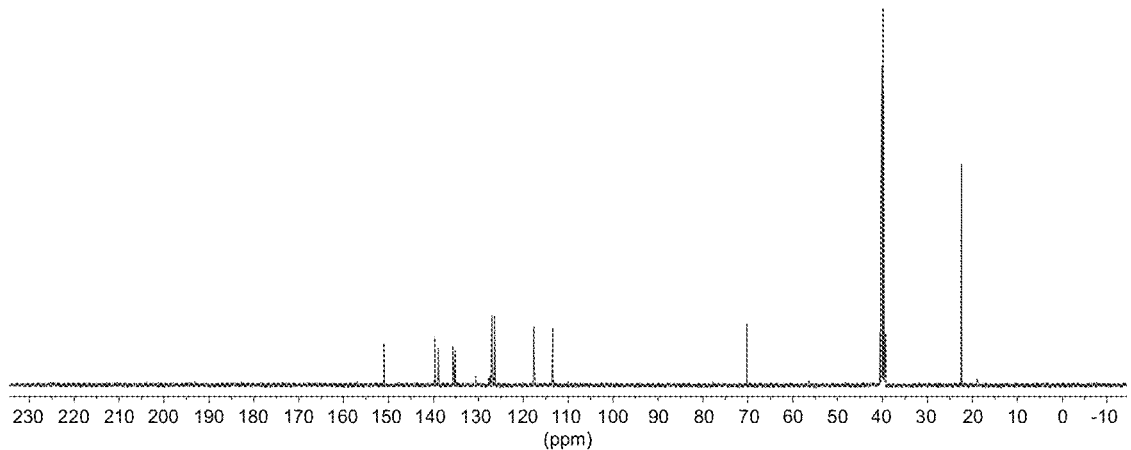
FIG. 32 shows a graph illustrating $^{13}$C NMR spectrum for compound 16b in $(CD_3)_2SO$ (100 MHz).

To a solution of [1,1'-biphenyl]-4,4'-dicarboxaldehyde (50 mg, 0.24 mmol) in EtOH (3 mL), 4-isopropoxyphenylhydrazine hydrochloride (121 mg, 0.59 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 16b (21 mg, 18%) as a yellow solid: $^1$H NMR (400 MHz, (CD$_3$)$_2$SO, FIG. 31) δ 10.17 (s, 2H), 7.80 (s, 2H), 7.68 (d, J=8.8 Hz, 4H), 7.65 (d, J=8.8 Hz, 4H), 6.97 (d, J=8.9 Hz, 4H), 6.79 (d, J=8.9 Hz, 4H), 4.40 (p, J=6.1 Hz, 2H), 1.20 (s, 6H), 1.19 (s, 6H); $^{13}$C NMR (100 MHz, (CD$_3$)$_2$SO, FIG. 32) δ 151.0, 139.7, 138.9, 135.7, 135.2, 127.0, 126.4, 117.6, 113.5, 70.2, 22.4.

Preparation of Compound 17a

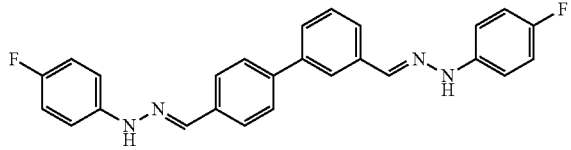 [SMILES: Fc1ccc(N/N=C/c2ccc(-c3cccc(/C=N/Nc4ccc(F)cc4)c3)cc2)cc1]

Figure 33:
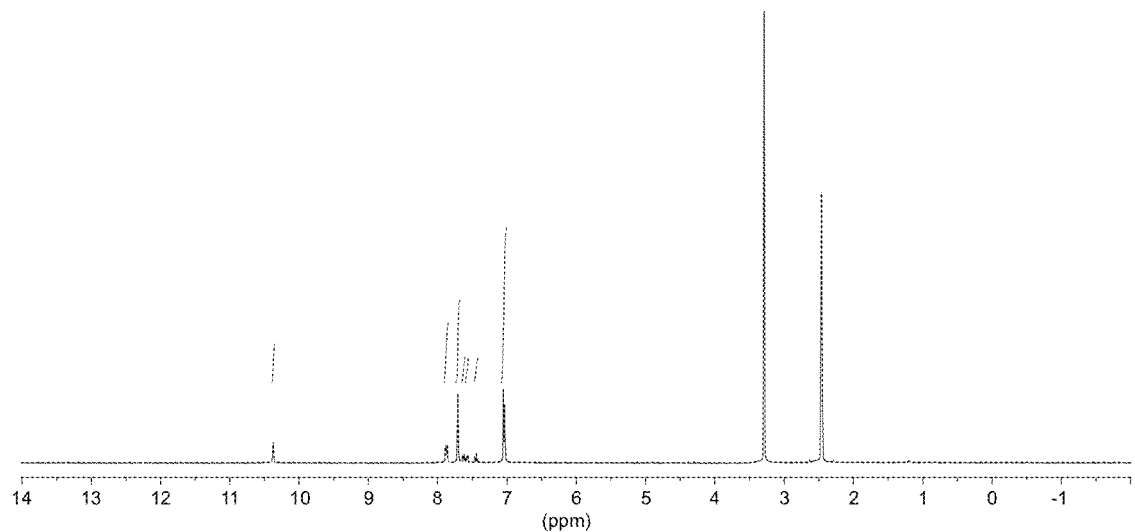
FIG. 33 shows a graph illustrating $^1$H NMR spectrum for compound 17a in $(CD_3)_2SO$ (400 MHz).
Figure 34:
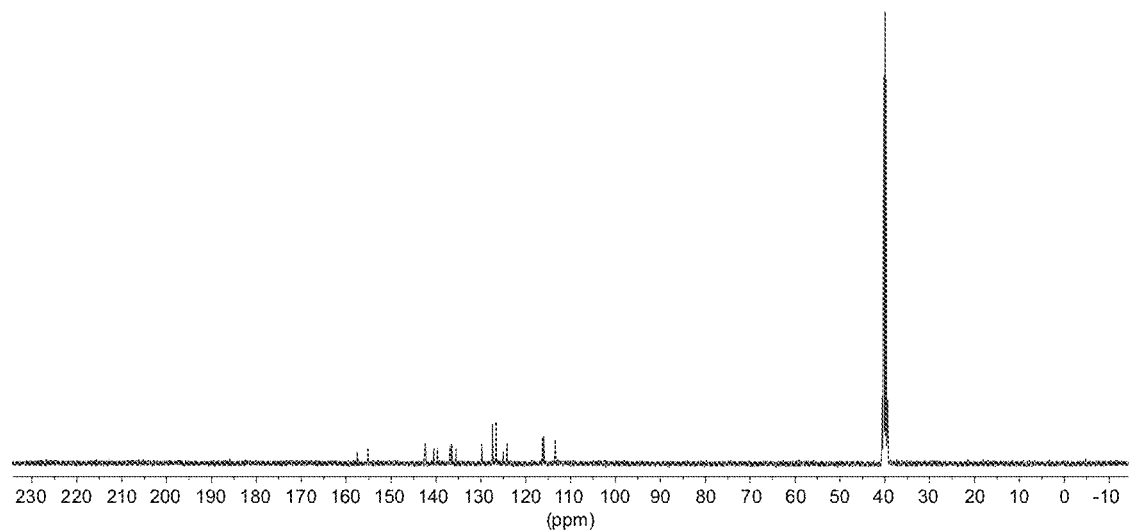
FIG. 34 shows a graph illustrating $^{13}$C NMR spectrum for compound 17a in $(CD_3)_2SO$ (100 MHz).

To a solution of [1,1'-biphenyl]-3,4'-dicarboxyaldehyde (344 mg, 1.64 mmol) in 1,4-dioxane (7.5 mL), 4-flurophenylhydrazine hydrochloride (146 mg, 0.82 mmol) and 1 N HCl (0.75 mL) were added. The reaction mixture was stirred at 90° C. for 3 h and the resulting solution was neutralized by the addition of Et$_3$N (0.244 mL) and the volatile components of the reaction mixture were evaporated under vacuum. Purification by flash column chromatography (SiO$_2$, CH$_2$Cl$_2$ containing 0.5 v/v of Et$_3$N) afforded compound 17a (39 mg, 9%) as a yellow solid: $^1$H NMR (400 MHz, (CD$_3$)$_2$SO, FIG. 33) δ 10.38 (s, 1H), 10.37 (s, 1H), 7.89 (s, 1H), 7.88 (s, 1H), 7.86 (s, 1H), 7.70 (m, 4H), 7.63 (d, J=7.8 Hz, 1H), 7.57 (d, J=7.5 Hz, 1H), 7.44 (t, J=7.8 Hz, 1H), 7.04 (d, J=7.6 Hz, 8H); $^{13}$C NMR (100 MHz, (CD$_3$)$_2$SO, FIG. 34) δ 157.5, 155.2, 142.35, 142.33, 140.5, 139.6, 136.9, 136.7, 136.4, 135.5, 129.7, 127.4, 126.6, 126.5, 125.0, 124.2, 116.2, 116.0, 113.45, 113.41.

Preparation of Compound 17b

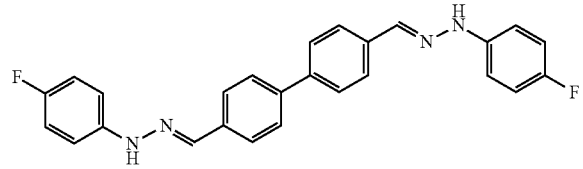 [SMILES: Fc1ccc(N/N=C/c2ccc(-c3ccc(/C=N/Nc4ccc(F)cc4)cc3)cc2)cc1]

Figure 35:
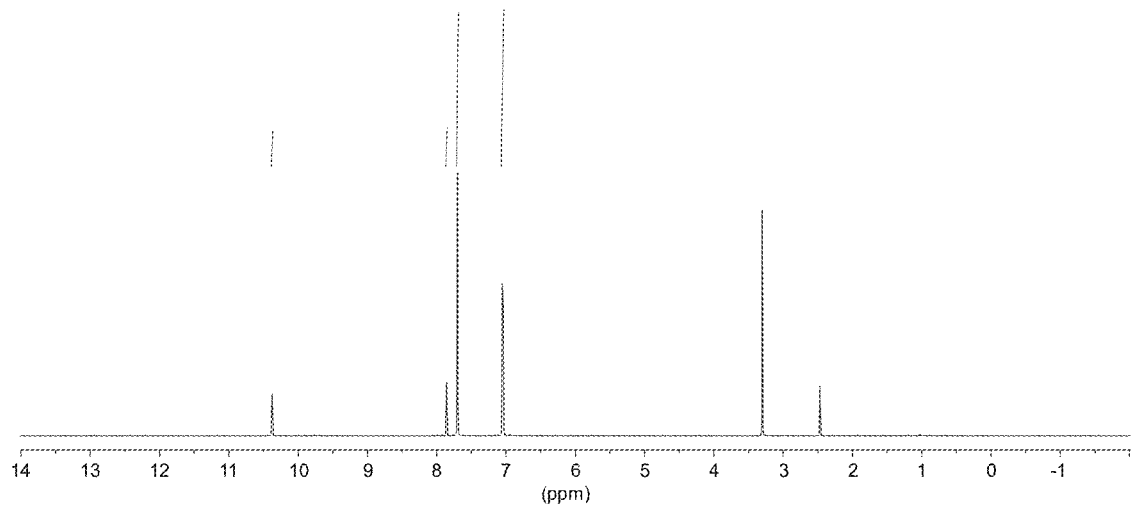
FIG. 35 shows a graph illustrating $^1$H NMR spectrum for compound 17b in $(CD_3)_2SO$ (400 MHz).
Figure 36:
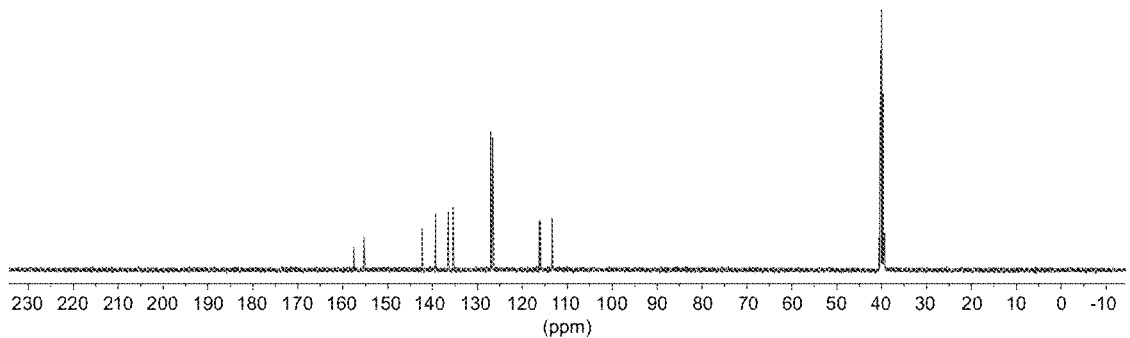
FIG. 36 shows a graph illustrating $^{13}$C NMR spectrum for compound 17b in $(CD_3)_2SO$ (100 MHz).

To a solution of [1,1'-biphenyl]-4,4'-dicarboxaldehyde (150 mg, 0.71 mmol) in EtOH (10 mL), 4-fluorophenylhydrazine hydrochloride (347 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 17b (103 mg, 34%) as a yellow solid: $^1$H NMR (400 MHz, (CD$_3$)$_2$SO, FIG. 35) δ 10.37 (s, 2H), 7.86 (s, 2H), 7.70 (br s, 8H), 7.05 (d, J=6.7 Hz, 8H); $^{13}$C NMR (100 MHz, (CD$_3$)$_2$SO, FIG. 36) δ 157.5, 155.2, 142.4, 142.3, 139.3, 136.5, 135.4, 127.1, 126.6, 116.2, 116.0, 113.4, 113.3.

Preparation of Compound 17c

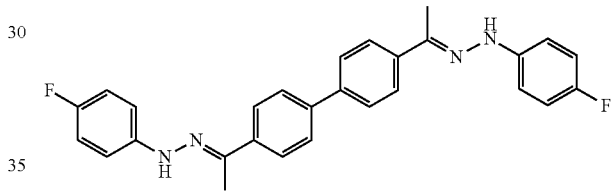

Figure 37:
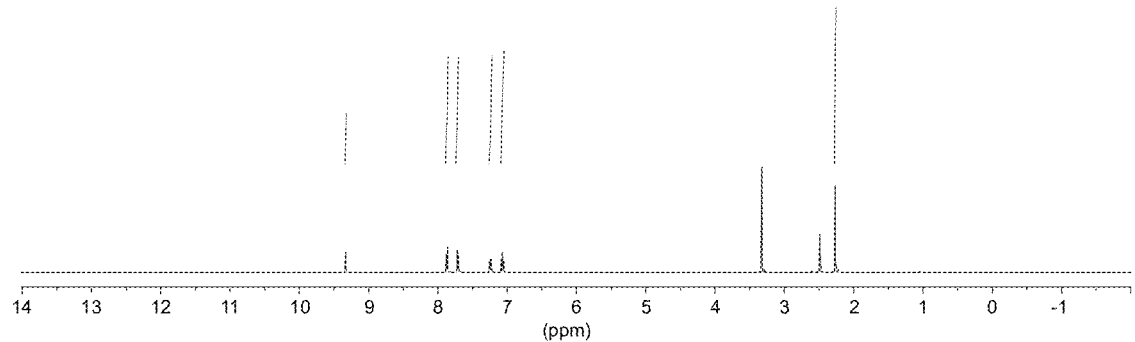
FIG. 37 shows a graph illustrating $^1$H NMR spectrum for compound 17c in $(CD_3)_2SO$ (500 MHz).
Figure 38:
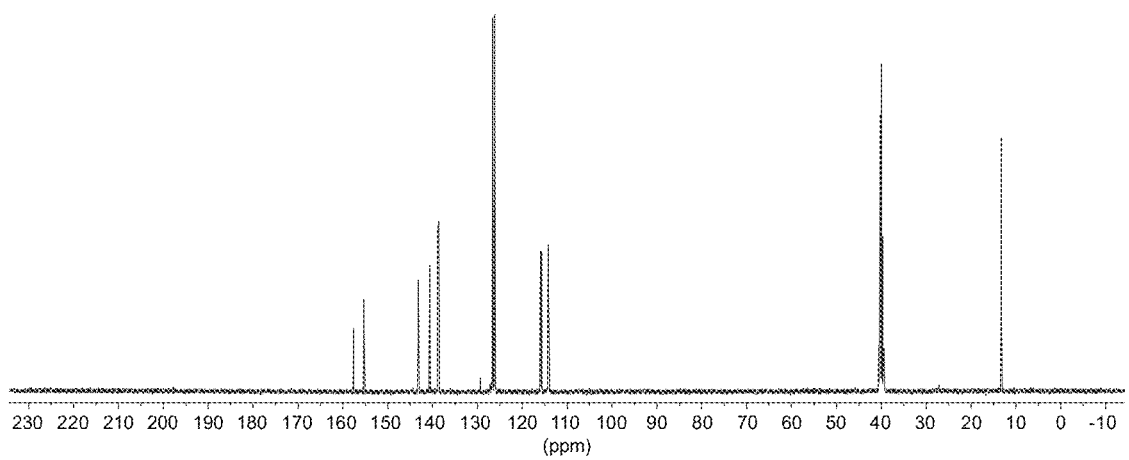
FIG. 38 shows a graph illustrating $^{13}$C NMR spectrum for compound 17c in $(CD_3)_2SO$ (100 MHz).

To a solution of 4,4'-diacetylbiphenyl (80 mg, 0.34 mmol) in EtOH (4 mL), 4-fluorophenylhydrazine hydrochloride (164 mg, 1.01 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 17c (68 mg, 44%) as a yellow solid: $^1$H NMR (500 MHz, (CD$_3$)$_2$SO, FIG. 37) δ 9.33 (s, 2H), 7.87 (d, J=8.6 Hz, 4H), 7.72 (d, J=8.6 Hz, 4H), 7.24 (dd, J$_1$=9.1 Hz, J$_2$=4.8 Hz, 4H), 7.07 (t, J=9.1 Hz, 4H), 2.27 (s, 6H); $^{13}$C NMR (100 MHz, (CD$_3$)$_2$SO, FIG. 38) δ 157.6, 155.3, 143.17, 143.15, 140.6, 138.9, 138.6, 126.6, 126.1, 115.9, 115.7, 114.3, 114.2.13.2.

Preparation of Compound 18a

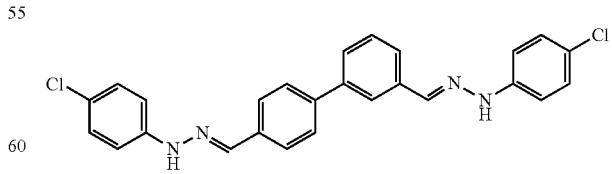

Figure 39:
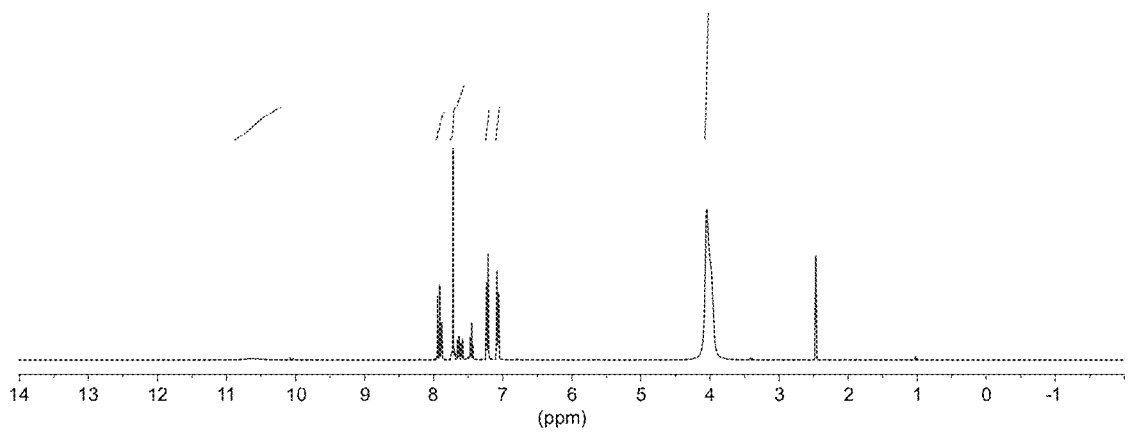
FIG. 39 shows a graph illustrating $^1$H NMR spectrum for compound 18a in $(CD_3)_2SO$ (400 MHz).
Figure 40:
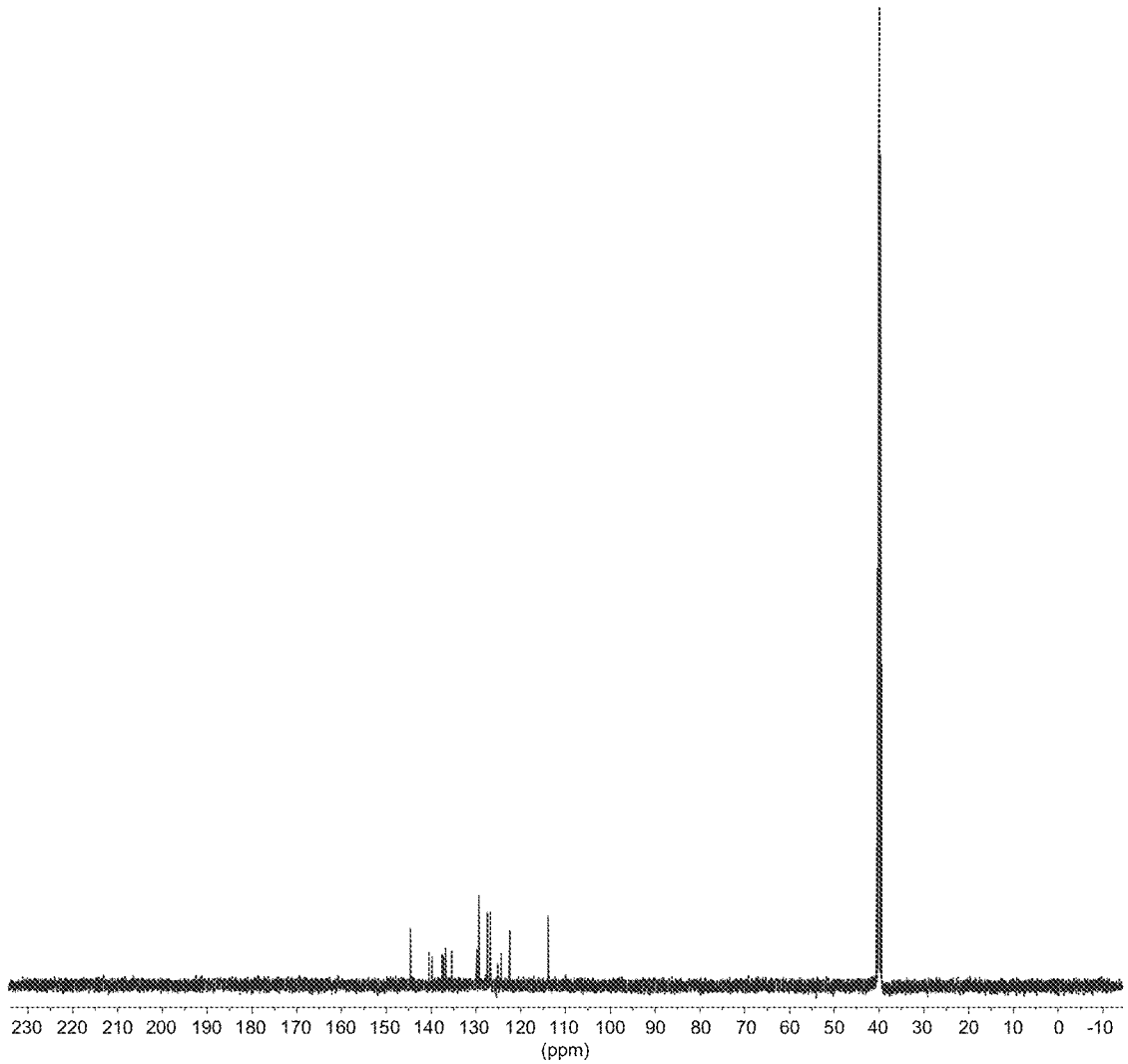
FIG. 40 shows a graph illustrating $^{13}$C NMR spectrum for compound 18a in $(CD_3)_2SO$ (100 MHz).

To a solution of [1,1'-biphenyl]-3,4'-dicarboxaldehyde (210 mg, 1 mmol) in EtOH (20 mL), 4-chlorophenylhydrazine hydrochloride (347 mg, 2.14 mmol) and a catalytic amount of concentrated HCl (0.04 mL) were added. The reaction mixture was stirred at 90° C. for 1 h and the resulting solution was filtered. The residue obtained was washed with CH$_2$Cl$_2$ (5 mL), EtOAc (5 mL), MeOH (5 mL), and hot EtOH (5 mL) to afford compound 18a (422 mg, 92%) as a yellow solid: $^1$H NMR (400 MHz, (CD$_3$)$_2$SO, FIG. 39) δ 10.59 (br s, 2H), 7.96 (s, 1H), 7.93 (s, 2H), 7.80-7.72 (m, 4H), 7.68 (d, J=8.0 Hz, 1H), 7.63 (d, J=8.4 Hz, 1H), 7.49 (t, J 8.0 Hz, 1H), 7.264 (d, J=8.8 Hz, 2H), 7.258 (d, J=8.8 Hz, 2H), 7.11 (d, J=8.8, Hz, 2H), 7.10 (d, J=8.8, Hz, 2H); $^{13}$C NMR (100 MHz, (CD$_3$)$_2$SO, FIG. 40) δ 144.2, 140.1, 139.4, 137.1, 136.8, 136.3, 135.0, 129.4, 128.9, 127.0, 126.3 (2 carbons), 124.7, 124.0, 122.0, 113.51, 113.47.

Preparation of Compound 18b

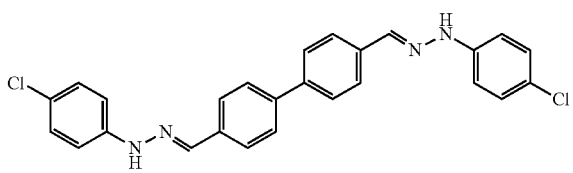 [SMILES: Clc1ccc(N/N=C/c2ccc(-c3ccc(/C=N/Nc4ccc(Cl)cc4)cc3)cc2)cc1]

Figure 41:
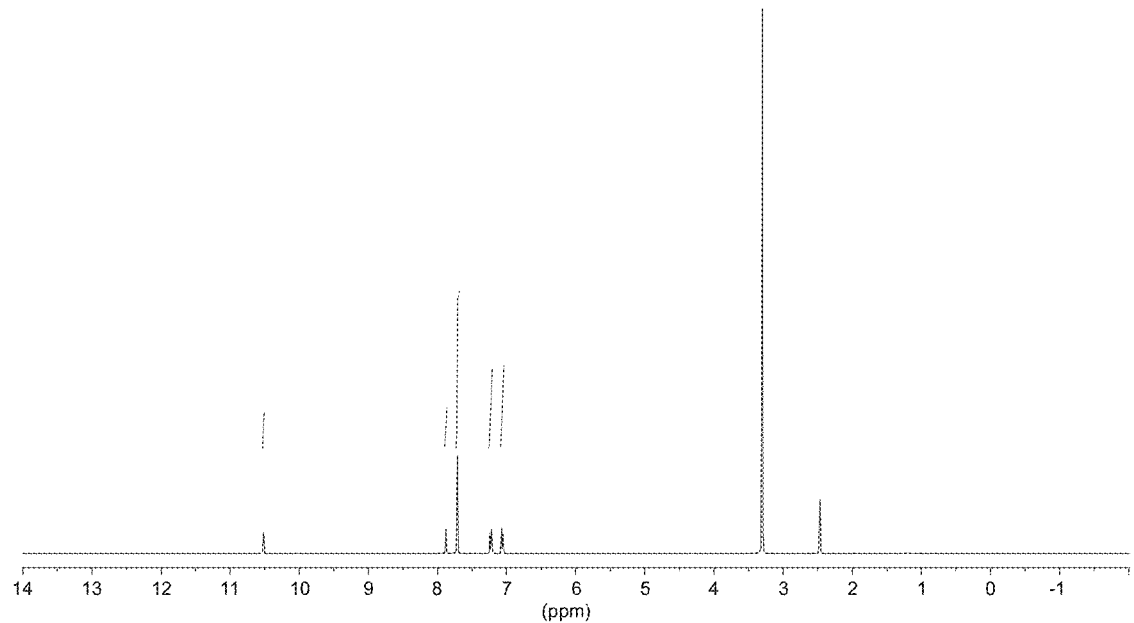
FIG. 41 shows a graph illustrating $^1$H NMR spectrum for compound 18b in $(CD_3)_2SO$ (400 MHz).
Figure 42:
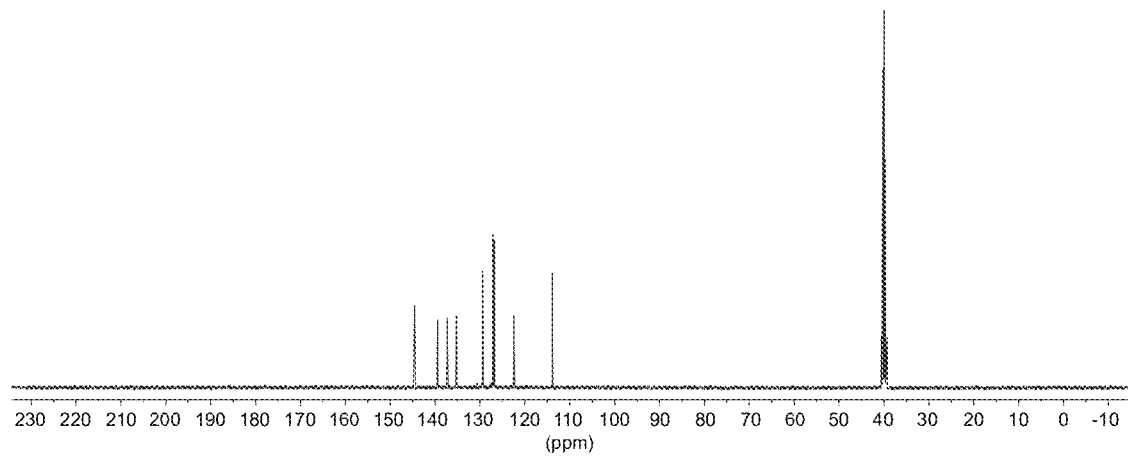
FIG. 42 shows a graph illustrating $^{13}$C NMR spectrum for compound 18b in $(CD_3)_2SO$ (100 MHz).

To a solution of [1,1'-biphenyl]-4,4'-dicarboxaldehyde (150 mg, 0.71 mmol) in EtOH (10 mL), 4-chlorophenylhydrazine hydrochloride (383 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 18b (250 mg, 77%) as a yellow solid: $^1$H NMR (400 MHz, (CD$_3$)$_2$SO, FIG. 41) δ 10.52 (s, 2H), 7.88 (s, 2H), 7.71 (br s, 8H), 7.23 (d, J=8.5 Hz, 4H), 7.06 (d, J=8.5 Hz, 4H); $^{13}$C NMR (100 MHz, (CD$_3$)$_2$SO, FIG. 42) δ 144.6, 139.4, 137.3, 135.2, 129.4, 127.1, 126.8, 122.5, 113.9.

Preparation of Compound 19a

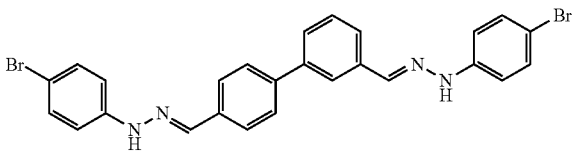 [SMILES: Brc1ccc(N/N=C/c2ccc(-c3cccc(/C=N/Nc4ccc(Br)cc4)c3)cc2)cc1]

Figure 43:
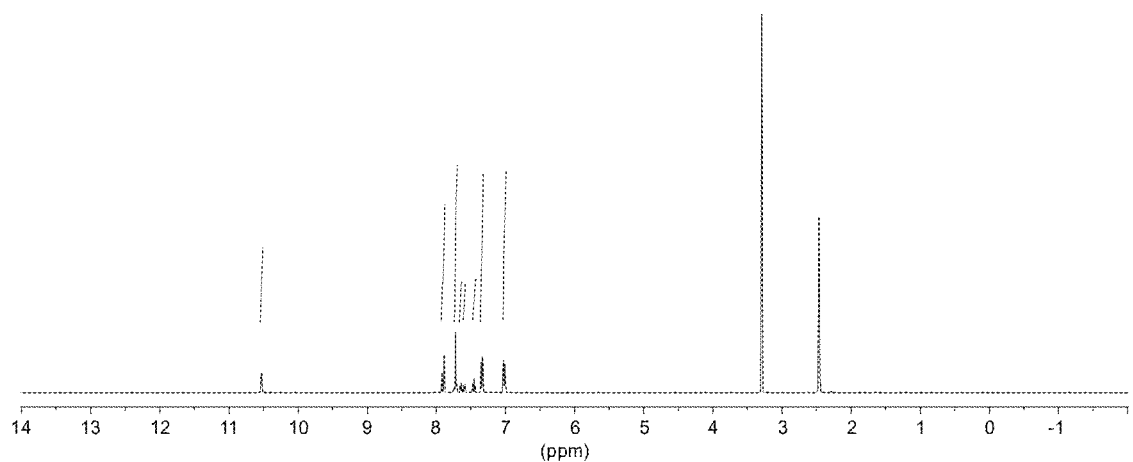
FIG. 43 shows a graph illustrating $^1$H NMR spectrum for compound 19a in $(CD_3)_2SO$ (400 MHz).
Figure 44:
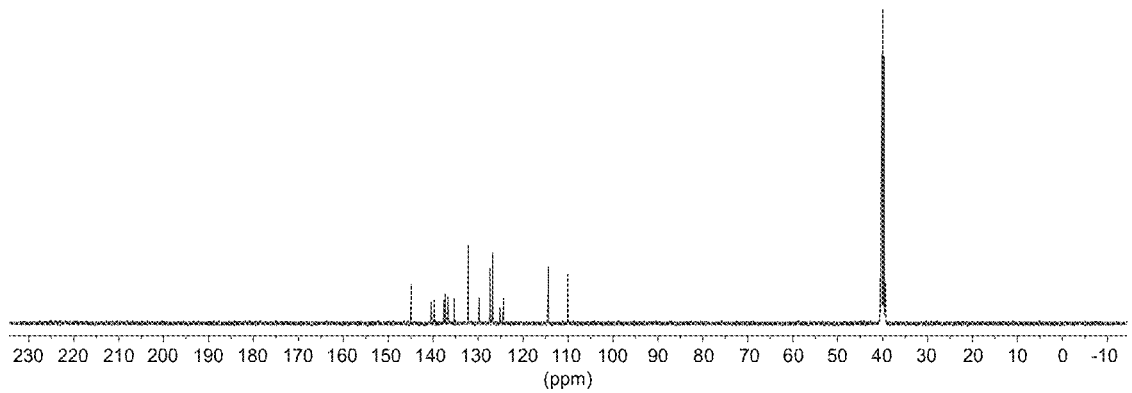
FIG. 44 shows a graph illustrating $^{13}$C NMR spectrum for compound 19a in $(CD_3)_2SO$ (100 MHz).

To a solution of [1,1'-biphenyl]-3,4'-dicarboxaldehyde (105 mg, 0.5 mmol) in a 1:4/EtOH:H$_2$O solution (5 mL), 4-bromophenylhydrazine hydrochloride (315 mg, 1.41 mmol) and a catalytic amount of concentrated HCl (0.04 mL) were added. The reaction mixture was stirred at 80° C. for 2 h and the resulting solution was filtered. The residue obtained was washed with hot EtOH (25 mL) to afford compound 19a (236 mg, 72%) as a yellow solid: $^1$H NMR (400 MHz, (CD$_3$)$_2$SO, FIG. 43) δ 10.54 (s, 1H), 10.53 (s, 1H), 7.92 (s, 1H), 7.89 (s, 2H), 7.73 (d, J=8.8 Hz, 2H), 7.70 (d, J=8.8 Hz, 2H), 7.64 (dt, J$_1$=7.7 Hz, J$_2$=1.3 Hz, 1H), 7.60 (dt, J=8.1 Hz, J$_2$=1.3 Hz, 1H), 7.45 (t, J=7.7 Hz, 1H), 7.34 (dd, J$_1$=8.9 Hz, J$_2$=2.4 Hz, 4H), 7.02 (dd, J$_1$=8.9 Hz, J$_2$=2.8 Hz, 4H); $^{13}$C NMR (100 MHz, (CD$_3$)$_2$SO, FIG. 44) δ 144.9, 140.5, 139.8, 137.7, 137.4, 136.7, 135.2, 132.2, 129.8, 127.4, 126.8, 125.2, 124.4, 114.42, 114.38, 110.0.

Preparation of Compound 19b

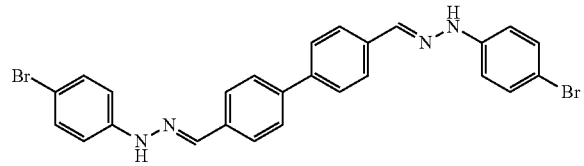

Figure 45:
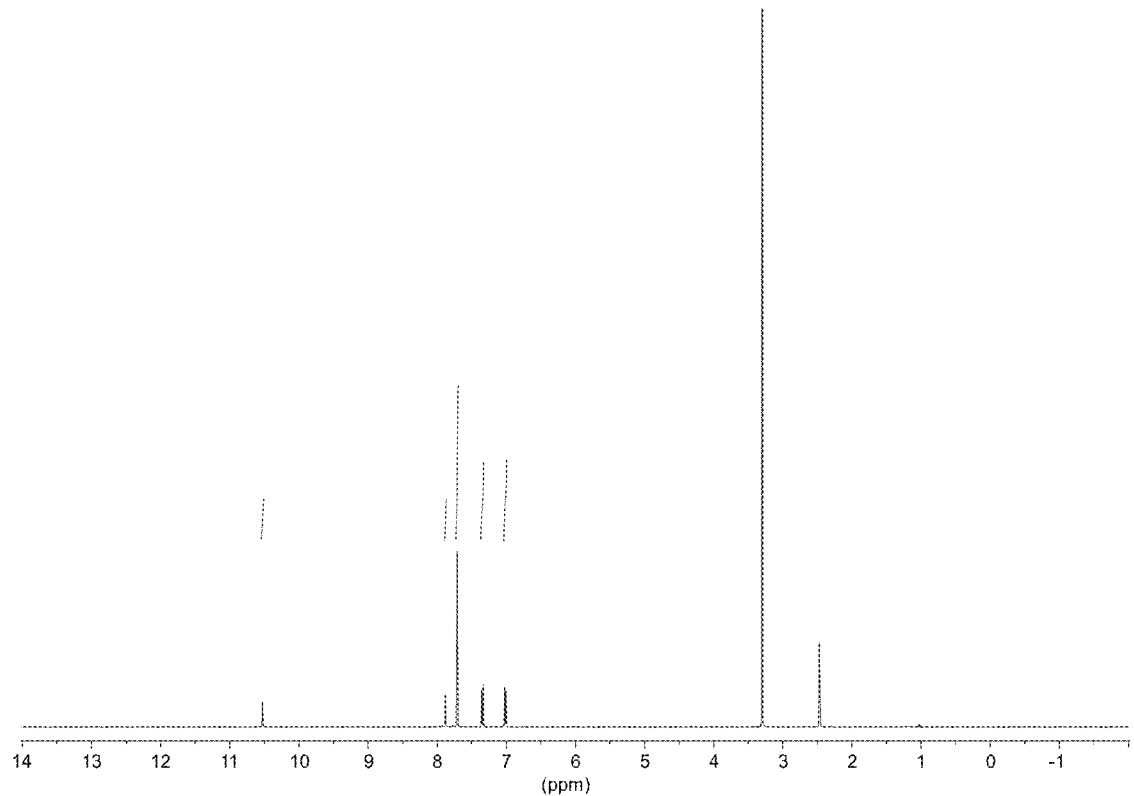
FIG. 45 shows a graph illustrating $^1$H NMR spectrum for compound 19b in $(CD_3)_2SO$ (400 MHz).
Figure 46:
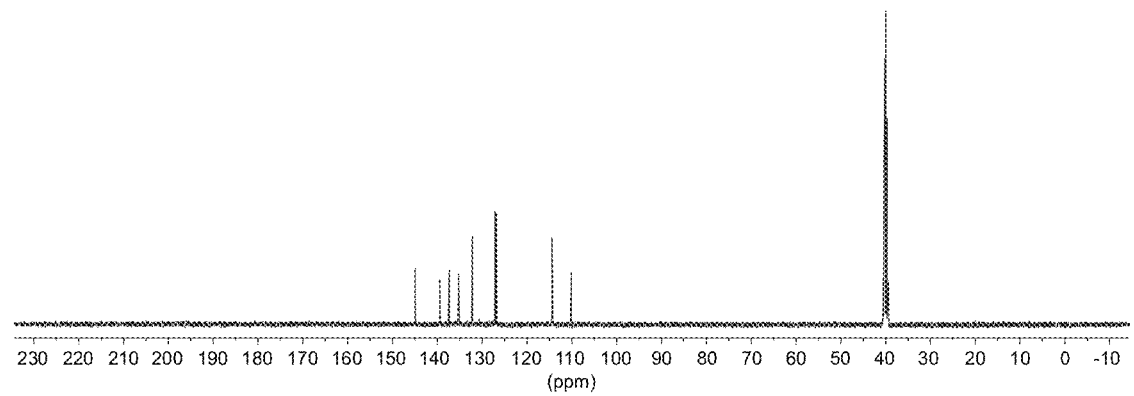
FIG. 46 shows a graph illustrating $^{13}$C NMR spectrum for compound 19b in $(CD_3)_2SO$ (100 MHz).

To a solution of [1,1'-biphenyl]-4,4'-dicarboxaldehyde (200 mg, 0.95 mmol) in EtOH (10 mL), 4-bromophenylhydrazine hydrochloride (637 mg, 2.85 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 19b (380 mg, 73%) as a yellow solid: $^1$H NMR (400 MHz, (CD$_3$)$_2$SO, FIG. 45) δ 10.53 (s, 2H), 7.88 (s, 2H), 7.71 (br s, 8H), 7.35 (d, J=8.8 Hz, 4H), 7.02 (d, J=8.8 Hz, 4H); $^{13}$C NMR (100 MHz, (CD$_3$)$_2$SO, FIG. 46) δ 144.9, 139.5, 137.4, 135.2, 132.2, 127.1, 126.8, 114.4, 110.1.

Preparation of Compound 20a

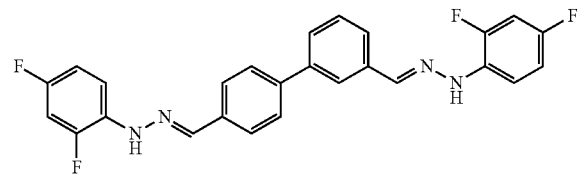 [SMILES: Fc1ccc(N/N=C/c2ccc(-c3cccc(/C=N/Nc4ccc(F)cc4F)c3)cc2)c(F)c1]

Figure 47:
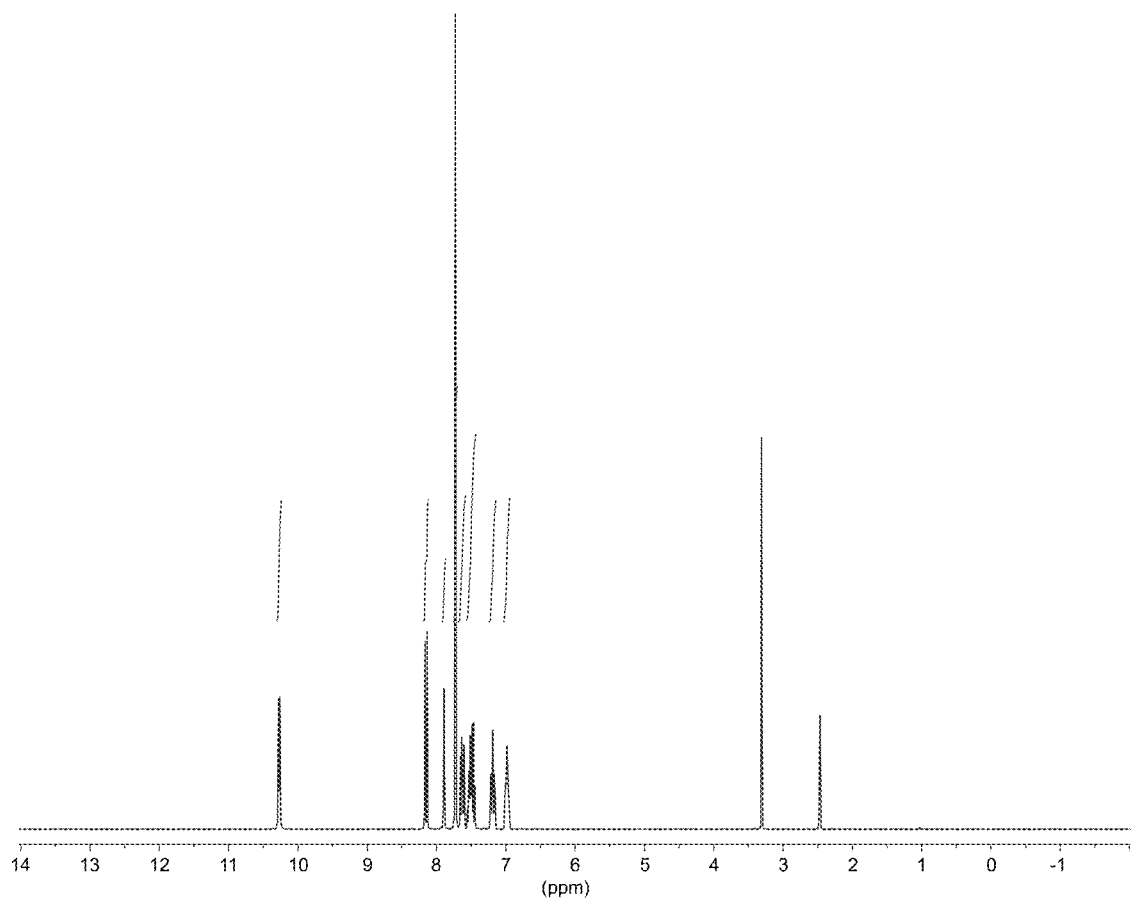
FIG. 47 shows a graph illustrating $^1$H NMR spectrum for compound 20a in $(CD_3)_2SO$ (400 MHz).
Figure 48:
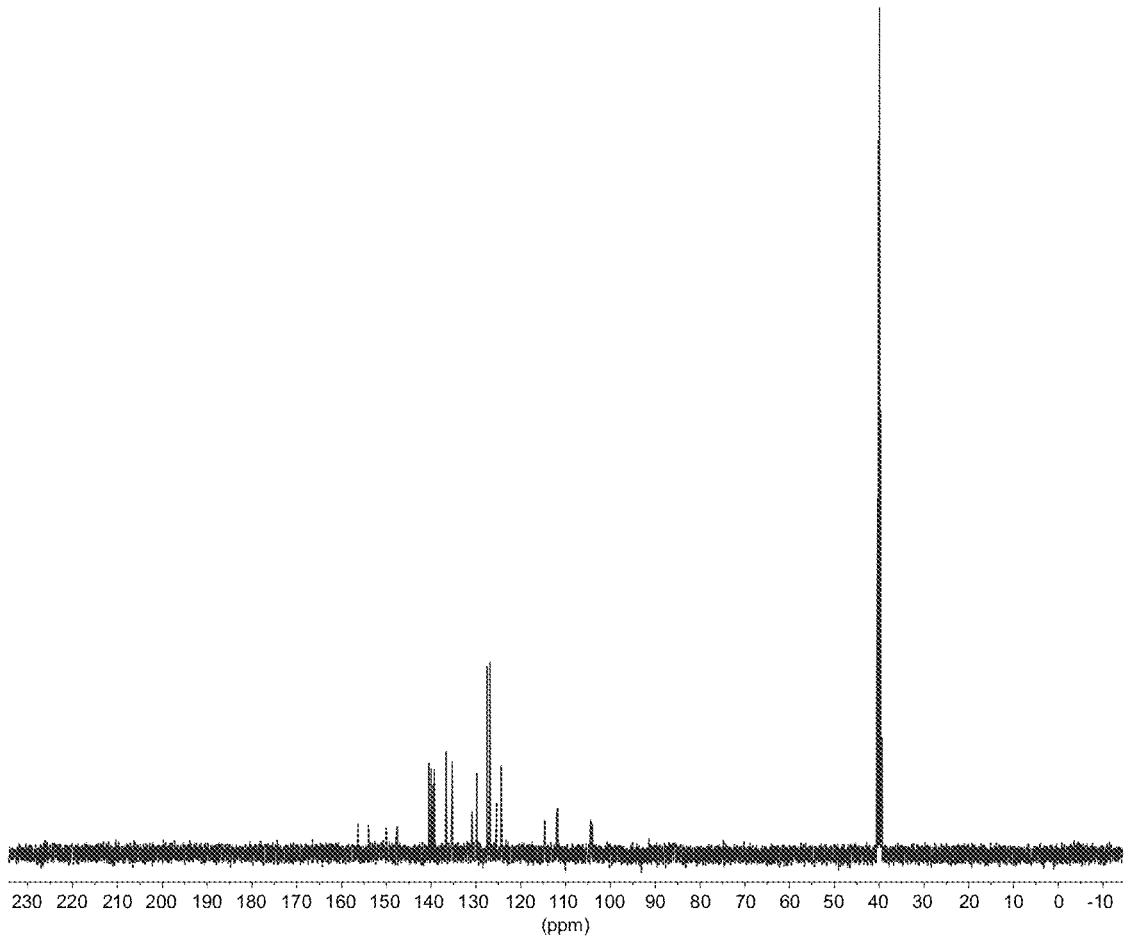
FIG. 48 shows a graph illustrating $^{13}$C NMR spectrum for compound 20a in $(CD_3)_2SO$ (100 MHz).

To a solution of [1,1'-biphenyl]-3,4'-dicarboxaldehyde (210 mg, 1 mmol) in EtOH (20 mL), 2,4-difluorophenylhydrazine hydrochloride (540 mg, 3 mmol) and a catalytic amount of concentrated HCl (0.04 mL) were added. The reaction mixture was stirred at 90° C. for 1 h and the resulting solution was filtered. The residue obtained was washed with 2 N HCl (20 mL) and hot EtOH (20 mL) to afford compound 20a (127 mg, 27%) as a yellow solid: $^1$H NMR (400 MHz, (CD$_3$)$_2$SO, FIG. 47) δ 10.31 (s, 1H), 10.29 (s, 1H), 8.19 (s, 1H), 8.16 (s, 1H), 7.92 (s, 1H), 7.76 (m, 4H), 7.67 (t, J=8.4 Hz, 2H), 7.58-7.52 (m, 2H), 7.51 (t, J=8.0 Hz, 1H), 7.25-7.19 (m, 2H), 7.06-6.98 (m, 2H); $^{13}$C NMR (100 MHz, (CD$_3$)$_2$SO, FIG. 48) δ 156.0, 155.9, 153.6, 153.5, 149.7, 149.5, 147.2, 147.1, 140.1, 139.6, 139.2, 138.9, 136.2, 134.9, 130.44, 130.36, 129.4, 127.1, 126.6, 126.5, 125.0, 124.0, 114.2, 111.6, 111.3, 104.1, 103.9, 103.6.

Preparation of Compound 20b

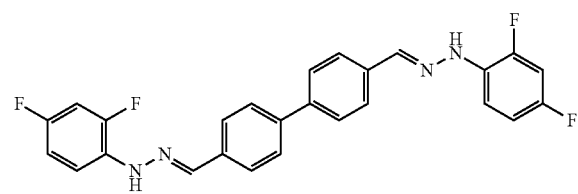 [SMILES: Fc1ccc(N/N=C/c2ccc(-c3ccc(/C=N/Nc4ccc(F)cc4F)cc3)cc2)c(F)c1]

Figure 49:
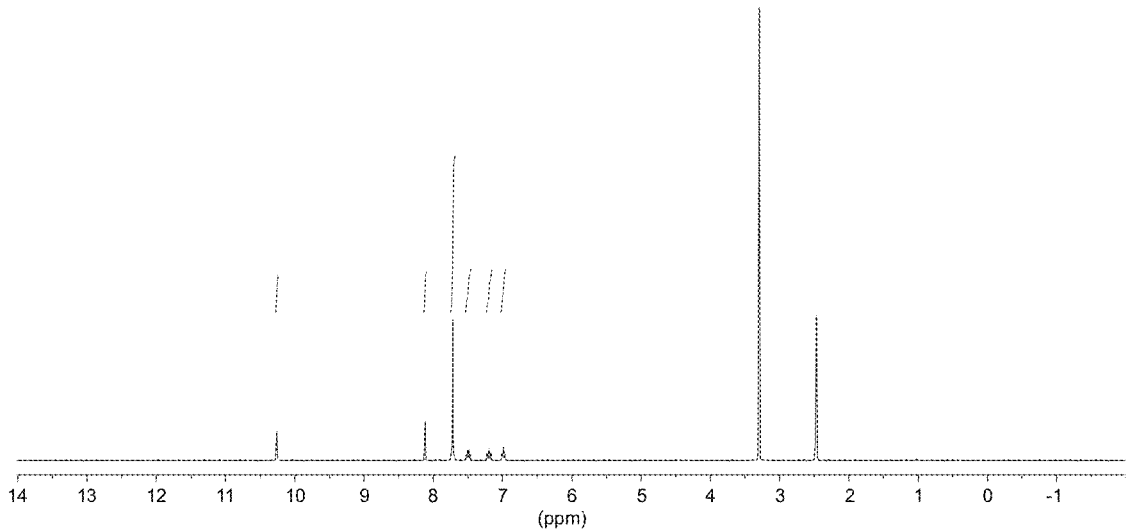
FIG. 49 shows a graph illustrating $^1$H NMR spectrum for compound 20b in $(CD_3)_2SO$ (400 MHz).
Figure 50:
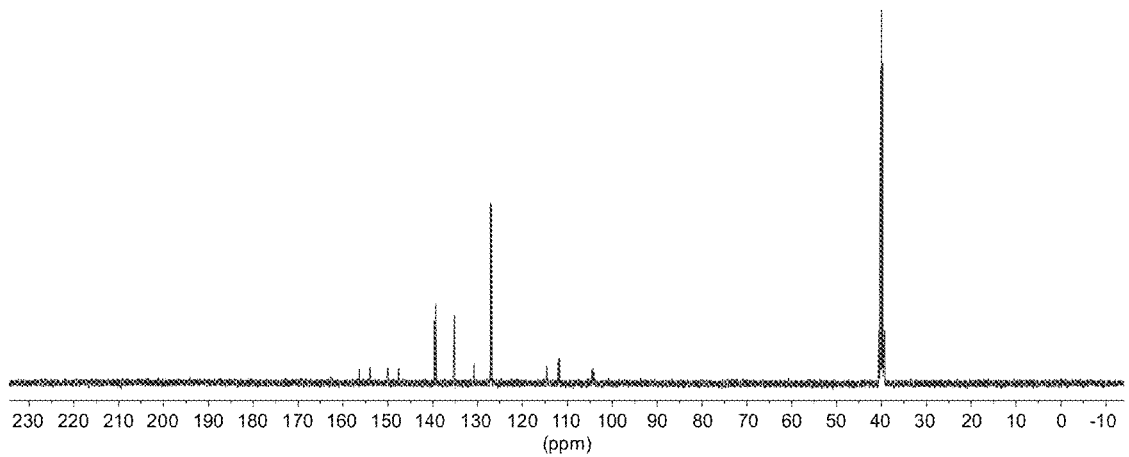
FIG. 50 shows a graph illustrating $^{13}$C NMR spectrum for compound 20b in $(CD_3)_2SO$ (100 MHz).

To a solution of [1,1'-biphenyl]-4,4'-dicarboxaldehyde (150 mg, 0.71 mmol) in EtOH (10 mL), 2,4-difluorophenylhydrazine hydrochloride (386 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 20b (138 mg, 42%) as a yellow solid: $^1$H NMR (400 MHz, (CD$_3$)$_2$SO, FIG. 49) δ 10.26 (s, 2H), 8.12 (s, 2H), 7.74-7.68 (m, 8H), 7.53-7.44 (m, 2H), 7.20 (m, 2H), 6.99 (m, 2H); $^{13}$C NMR (100 MHz, (CD$_3$)$_2$SO, FIG. 50) δ 156.4, 156.3, 154.0, 153.9, 150.1, 150.0, 147.7, 147.5, 139.6, 139.3, 135.2, 130.88, 130.85, 130.8, 127.2, 126.9, 114.6, 112.0, 111.8, 104.5, 104.3, 104.0.

Preparation of Compound 21a

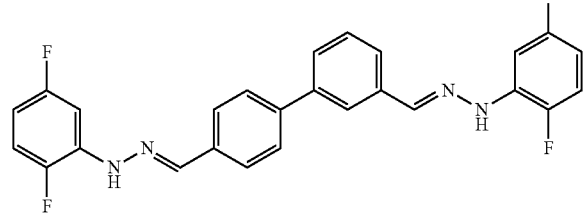

Figure 51:
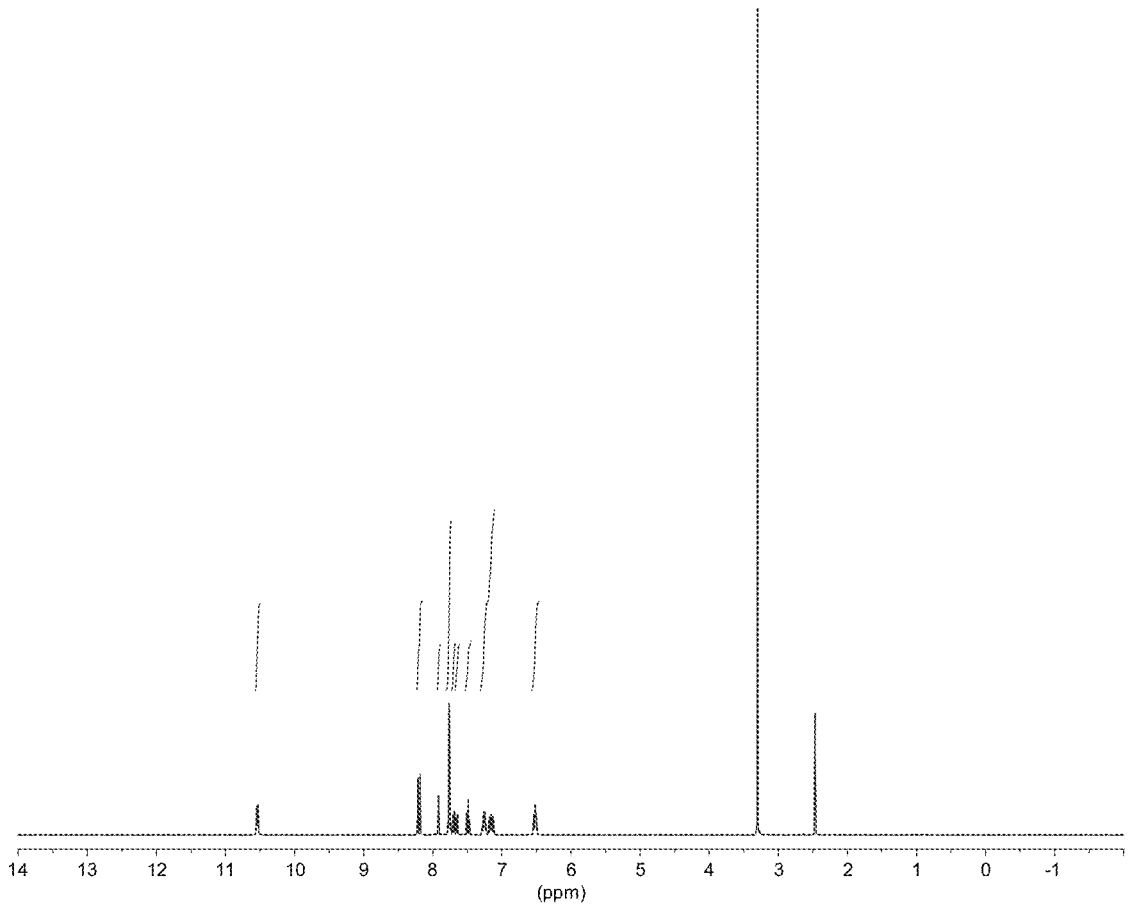
FIG. 51 shows a graph illustrating $^1$H NMR spectrum for compound 21a in $(CD_3)_2SO$ (400 MHz).
Figure 52:
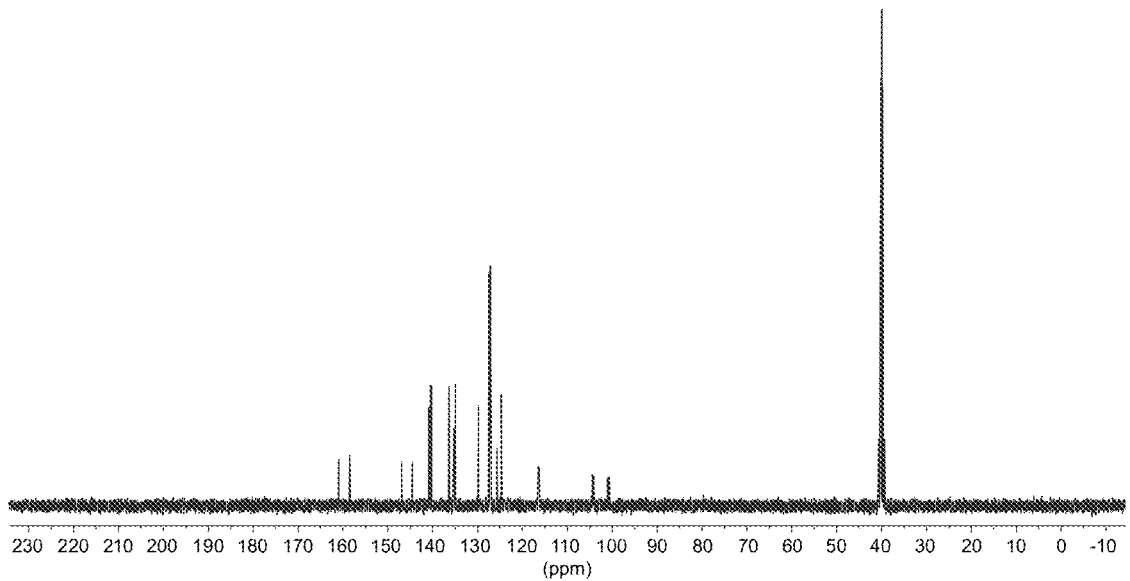
FIG. 52 shows a graph illustrating $^{13}$C NMR spectrum for compound 21a in $(CD_3)_2SO$ (100 MHz).

To a solution of [1,1'-biphenyl]-3,4'-dicarboxaldehyde (210 mg, 1 mmol) in EtOH (20 mL), 2,5-difluorophenylhydrazine hydrochloride (540 mg, 3 mmol) and a catalytic amount of concentrated HCl (0.04 mL) were added. The reaction mixture was stirred at 90° C. for 1 h and the resulting solution was filtered. The residue obtained was washed with 2 N HCl (20 mL) and hot EtOH (20 mL) to afford compound 21a (280 mg, 61%) as a yellow solid: $^1$H NMR (400 MHz, (CD$_3$)$_2$SO, FIG. 51) δ 10.58 (s, 1H), 10.56 (s, 1H), 8.25 (s, 1H), 8.22 (s, 1H), 7.95 (s, 1H), 7.79 (d, J=8.8 Hz, 2H), 7.77 (d, J=9.2 Hz, 2H), 7.73 (d, J=7.6 Hz, 1H), 7.68 (d, J=8.4 Hz, 1H), 7.52 (t, J=8.0 Hz, 1H), 7.33-7.26 (m, 2H), 7.22-7.16 (m, 2H), 6.58-6.52 (m, 2H); $^{13}$C NMR (100 MHz, (CD$_3$)$_2$SO, FIG. 52) δ 160.5, 158.1, 146.5, 144.1, 140.4, 140.12, 140.07, 139.9, 135.9, 135.0, 134.8, 134.7, 134.6, 129.4, 127.1, 126.9, 126.8, 125.3, 124.3, 116.2, 116.1, 116.0, 115.9, 104.0, 103.9, 103.8, 103.7, 100.6, 100.32, 100.29, 100.2.

Preparation of Compound 21b

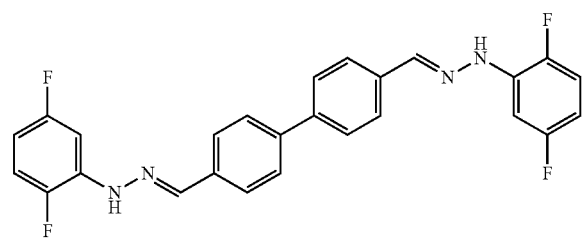 [SMILES: Fc1ccc(F)c(N/N=C/c2ccc(-c3ccc(/C=N/Nc4cc(F)ccc4F)cc3)cc2)c1]

Figure 53:
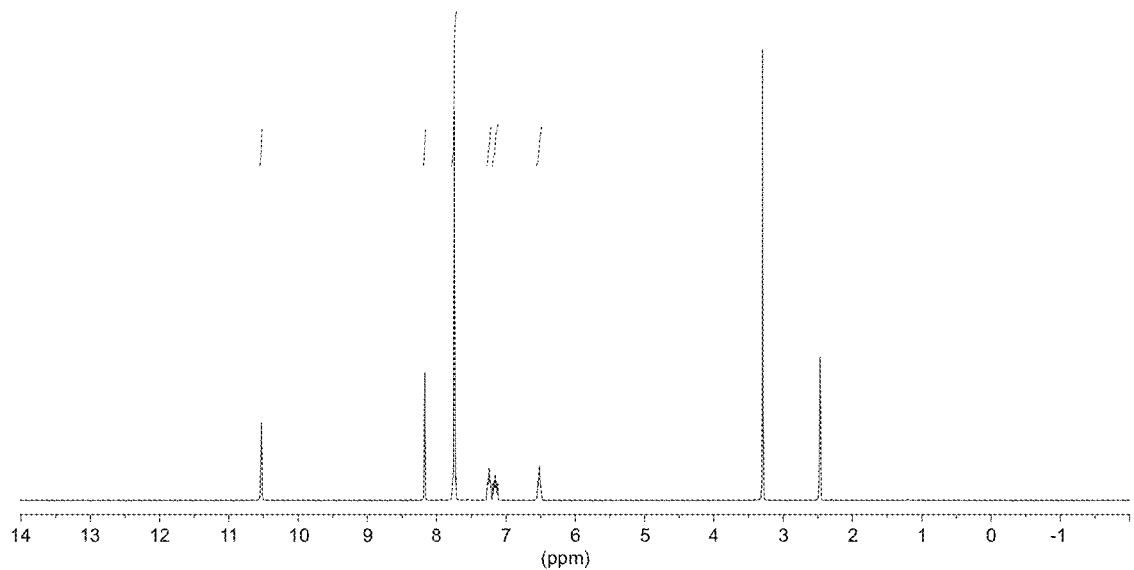
FIG. 53 shows a graph illustrating $^1$H NMR spectrum for compound 21b in $(CD_3)_2SO$ (400 MHz).
Figure 54:
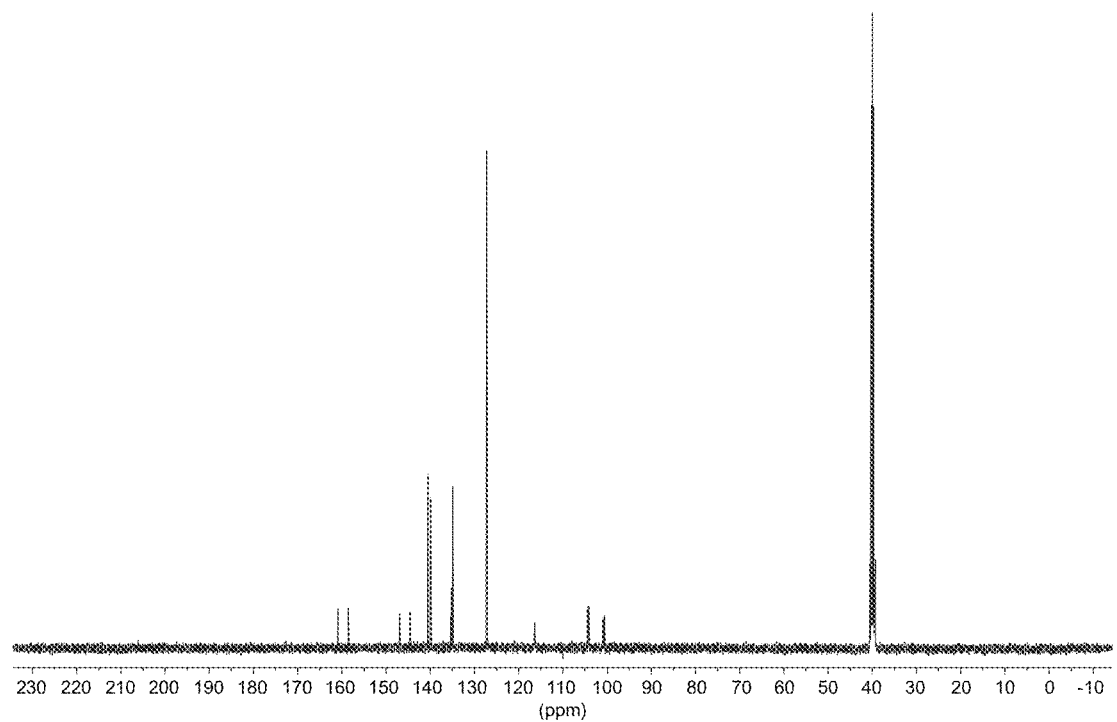
FIG. 54 shows a graph illustrating $^{13}$C NMR spectrum for compound 21b in $(CD_3)_2SO$ (100 MHz).

To a solution of [1,1'-biphenyl]-4,4'-dicarboxaldehyde (150 mg, 0.71 mmol) in EtOH (10 mL), 2,5-difluorophenylhydrazine hydrochloride (386 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 21b (130 mg, 39%) as a yellow solid: $^1$H NMR (400 MHz, (CD$_3$)$_2$SO, FIG. 53) δ 10.53 (s, 2H), 8.17 (s, 2H), 7.76 (d, J=9.1 Hz, 4H), 7.74 (d, J=9.4 Hz, 4H), 7.28-7.20 (m, 2H), 7.19-7.11 (m, 2H), 6.55-6.47 (m, 2H); $^{13}$C NMR (100 MHz, (CD$_3$)$_2$SO, FIG. 54) δ 160.9, 158.5, 146.89, 146.87, 144.55, 144.53, 140.5, 139.9, 135.3, 135.2, 135.1, 134.9, 127.22, 127.20, 116.6, 116.5, 116.4, 116.3, 104.5, 104.4, 104.2, 104.1, 100.9, 100.64, 100.60.

Preparation of Compound 22a

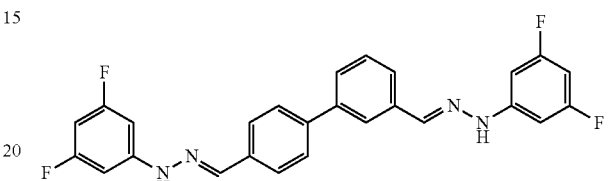

Figure 55:
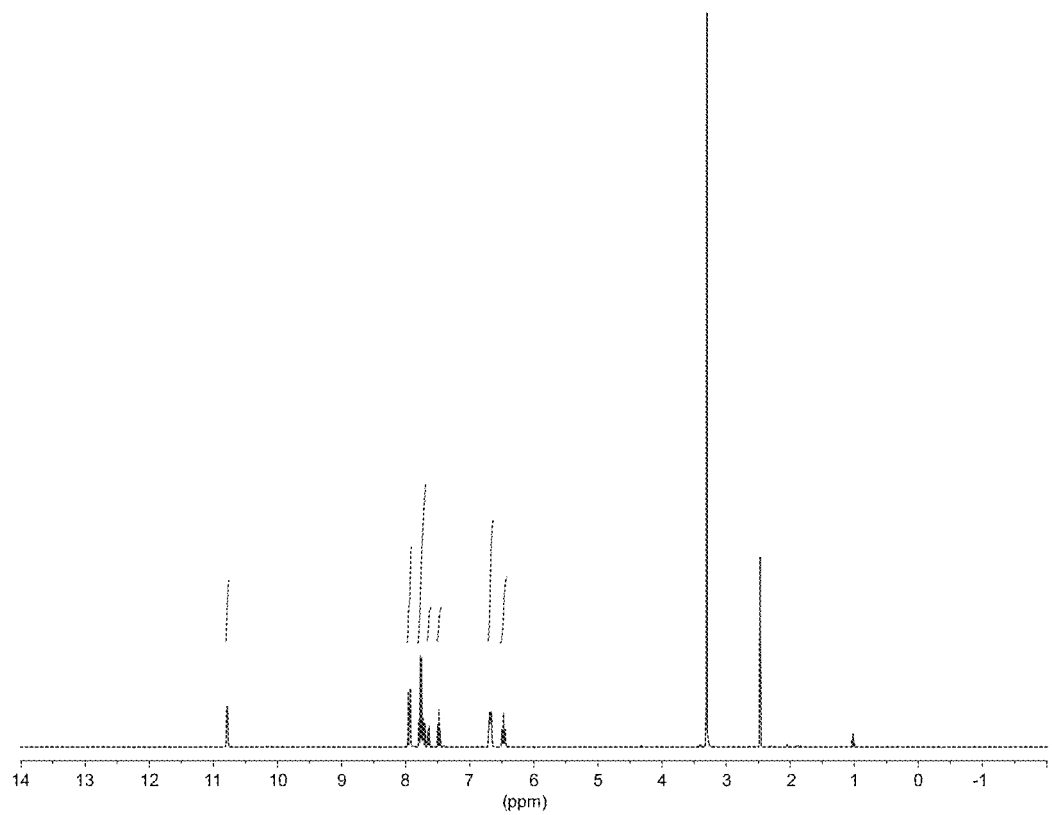
FIG. 55 shows a graph illustrating $^1$H NMR spectrum for compound 22a in $(CD_3)_2SO$ (400 MHz).
Figure 56:
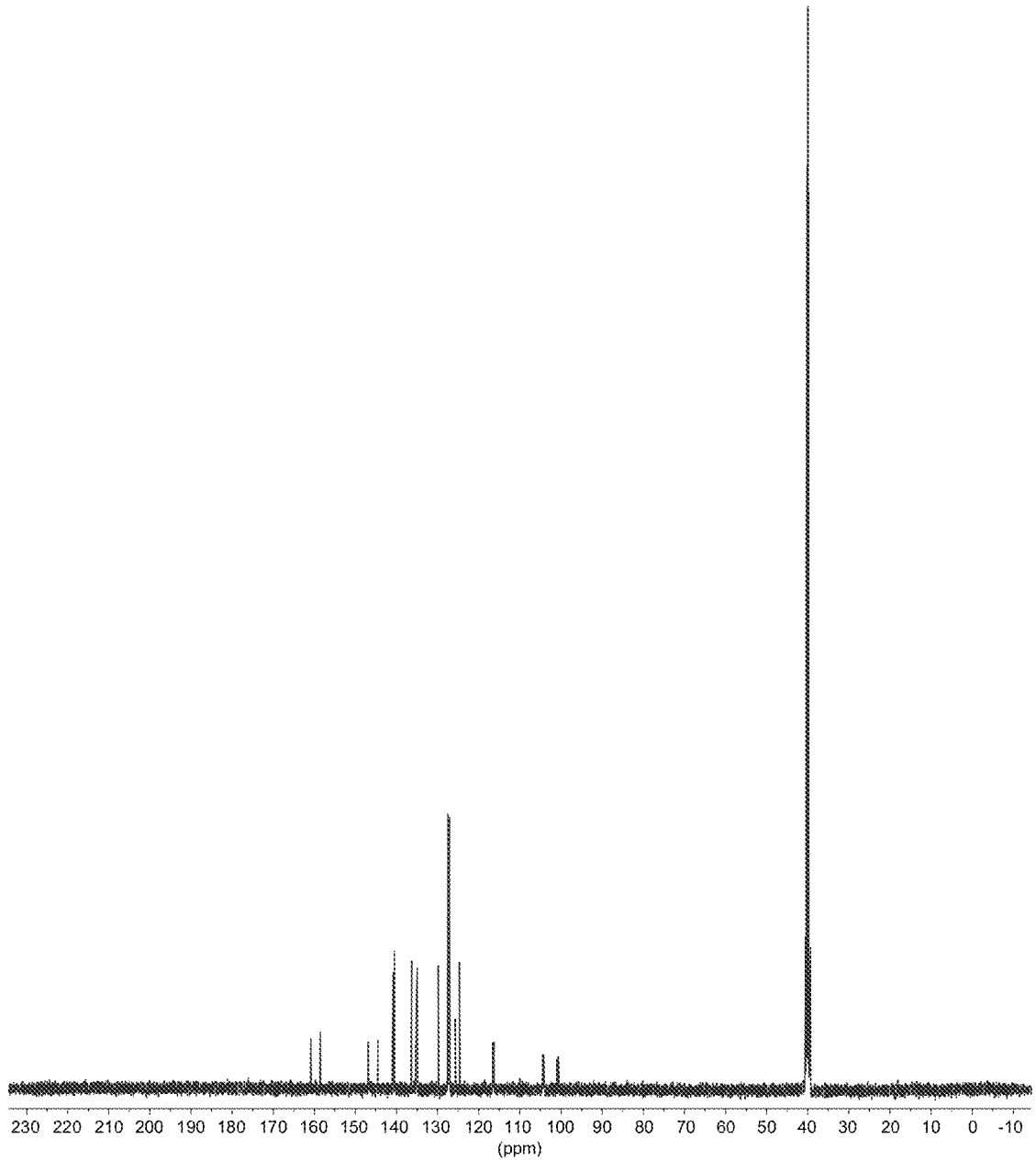
FIG. 56 shows a graph illustrating $^{13}$C NMR spectrum for compound 22a in $(CD_3)_2SO$ (100 MHz).

To a solution of [1,1'-biphenyl]-3,4'-dicarboxaldehyde (210 mg, 1 mmol) in EtOH (20 mL), 3,5-difluorophenylhydrazine hydrochloride (480 mg, 3 mmol) and a catalytic amount of concentrated HCl (0.04 mL) were added. The reaction mixture was stirred at 90° C. for 1 h and the resulting solution was filtered. The residue obtained was washed with 2 N HCl (20 mL) and hot EtOH (20 mL) to afford compound 22a (156 mg, 34%) as a yellow solid: $^1$H NMR (400 MHz, (CD$_3$)$_2$SO, FIG. 55) δ 10.82 (s, 1H), 10.81 (s, 1H), 7.99 (s, 1H), 7.97 (s, 1H), 7.96 (s, 1H), 7.81 (d, J=8.8 Hz, 2H), 7.78 (d, J 8.8 Hz, 2H), 7.74 (d, J=7.6 Hz, 1H), 7.67 (d, J=8.0 Hz, 1H), 7.51 (t, J=8.0 Hz, 1H), 6.73-6.69 (m, 4H), 6.50 (tt, J=9.6, 2.4 Hz, 2H); $^{13}$C NMR (100 MHz, (CD$_3$)$_2$SO, FIG. 56) δ 160.5, 158.12, 158.10, 146.5, 144.13, 144.11, 140.4, 140.12, 140.06, 139.8, 135.9, 134.9, 134.8, 134.7, 134.5, 129.5, 127.1, 126.9, 126.8, 125.3, 124.3, 116.2, 116.1, 116.0, 115.9, 104.0, 103.8, 100.6, 100.31, 100.27.

Preparation of Compound 22b

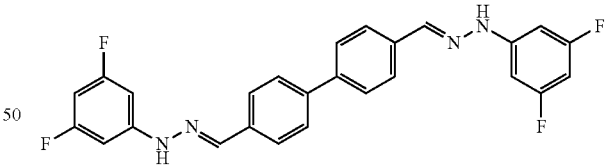

Figure 57:
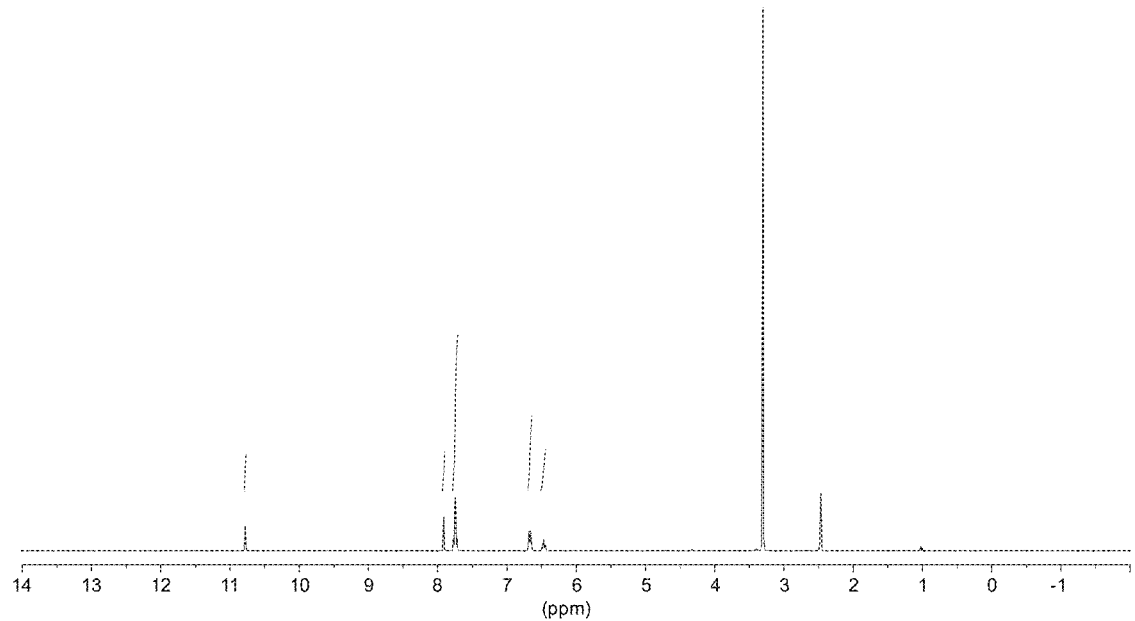
FIG. 57 shows a graph illustrating $^1$H NMR spectrum for compound 22b in $(CD_3)_2SO$ (400 MHz).
Figure 58:
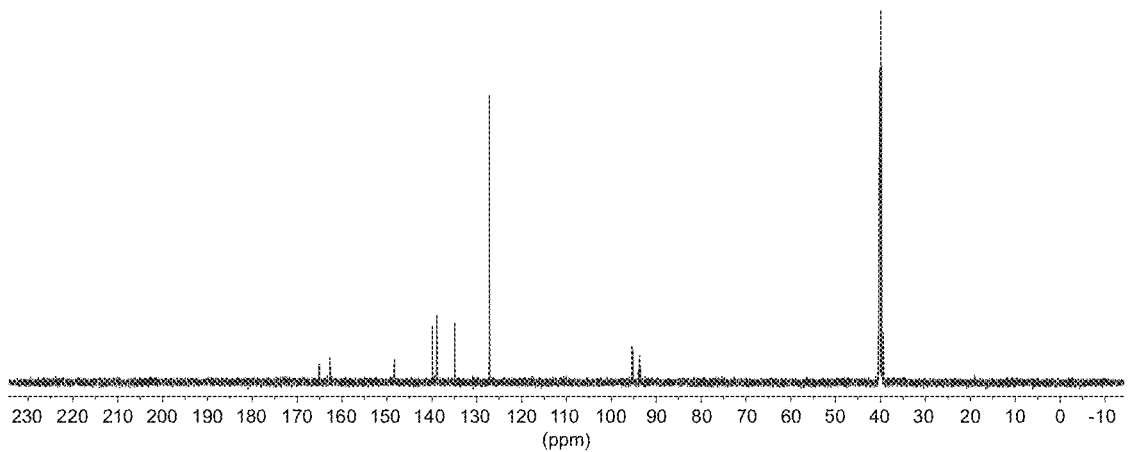
FIG. 58 shows a graph illustrating $^{13}$C NMR spectrum for compound 22b in $(CD_3)_2SO$ (100 MHz).

To a solution of [1,1'-biphenyl]-4,4'-dicarboxaldehyde (150 mg, 0.71 mmol) in EtOH (10 mL), 3,5-difluorophenylhydrazine hydrochloride (386 mg, 2.14 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 22b (135 mg, 41%) as a yellow solid: $^1$H NMR (400 MHz, (CD$_3$)$_2$SO, FIG. 57) δ 10.78 (s, 2H), 7.92 (s, 2H), 7.76 (d, J=8.6 Hz, 4H), 7.73 (d, J=8.8 Hz, 4H), 6.67 (dd, J=10.2 Hz, J$_2$=2.4 Hz, 4H), 6.47 (tt, J$_1$=9.4 Hz, J$_2$=2.4 Hz, 2H); $^{13}$C NMR (100 MHz, (CD$_3$)$_2$SO, FIG. 58) δ 165.2, 165.0, 162.8, 162.6, 148.4, 148.3, 148.2, 139.9, 138.9, 134.8, 127.2, 95.4, 95.1, 94.0, 93.7, 93.5.

Preparation of Compound 23b

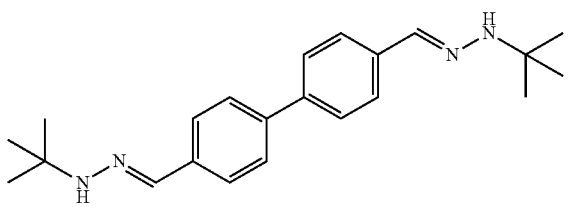 [SMILES: CC(C)(C)N/N=C/c1ccc(-c2ccc(/C=N/NC(C)(C)C)cc2)cc1]

Figure 59:
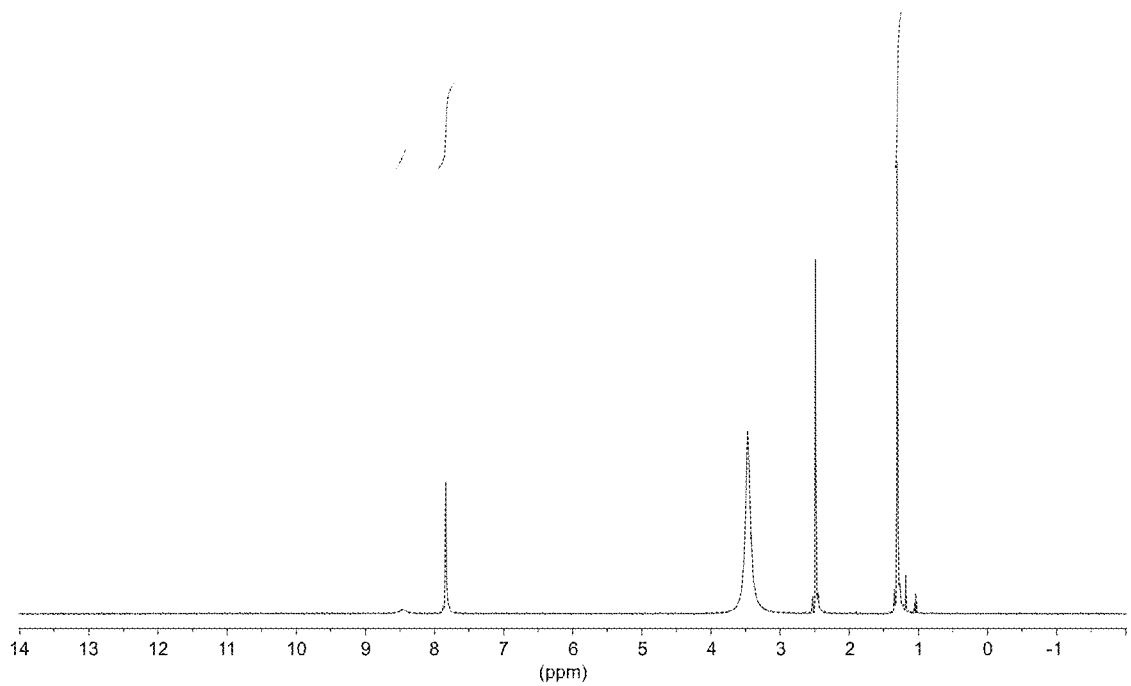
FIG. 59 shows a graph illustrating $^1$H NMR spectrum for compound 23b in $(CD_3)_2SO$ (500 MHz).
Figure 60:
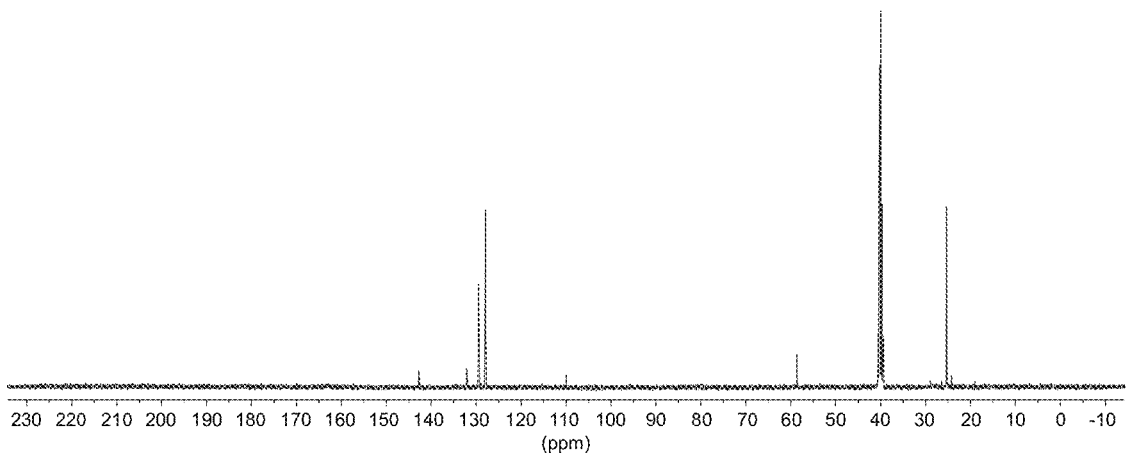
FIG. 60 shows a graph illustrating $^{13}$C NMR spectrum for compound 23b in $(CD_3)_2SO$ (100 MHz).

To a solution of [1,1'-biphenyl]-4,4'-dicarboxaldehyde (200 mg, 0.95 mmol) in EtOH (10 mL), tert-butylhydrazine hydrochloride (355 mg, 2.85 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 23b (210 mg, 63%) as a white solid: $^1$H NMR (500 MHz, (CD$_3$)$_2$SO, FIG. 59) δ 8.46 (s, 2H), 7.84 (br s, 10H), 1.31 (s, 18H); $^{13}$C NMR (100 MHz, (CD$_3$)$_2$SO, FIG. 60) δ 142.8, 132.1, 129.4, 128.0, 110.0, 58.6, 25.3.

Preparation of Compound 24a

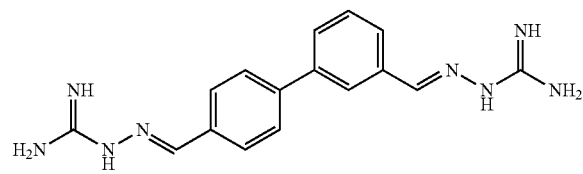 [SMILES: N=C(N)N/N=C/c1ccc(-c2cccc(/C=N/NC(=N)N)c2)cc1]

Figure 61:
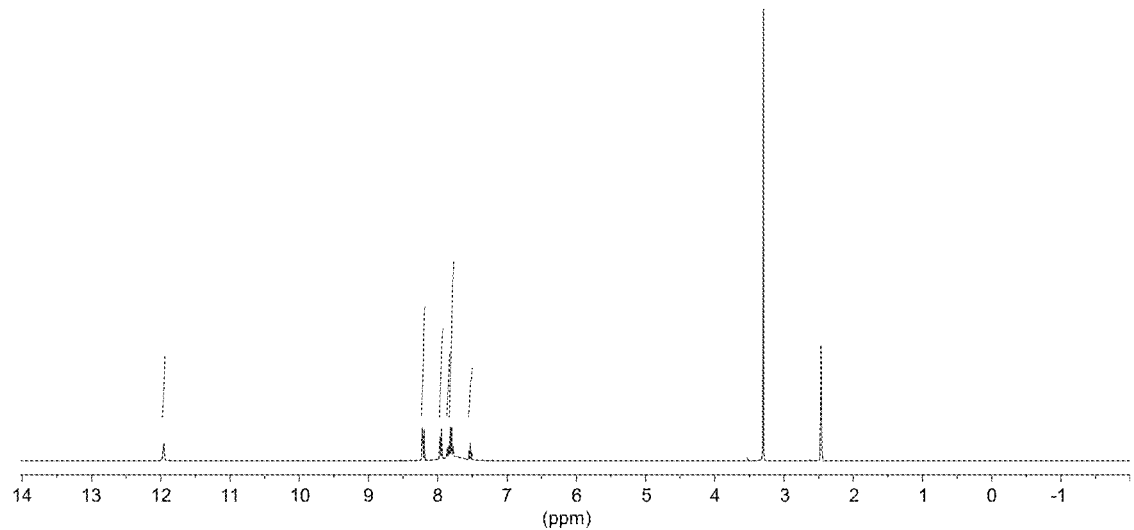
FIG. 61 shows a graph illustrating $^1$H NMR spectrum for compound 24a in $(CD_3)_2SO$ (400 MHz).
Figure 62:
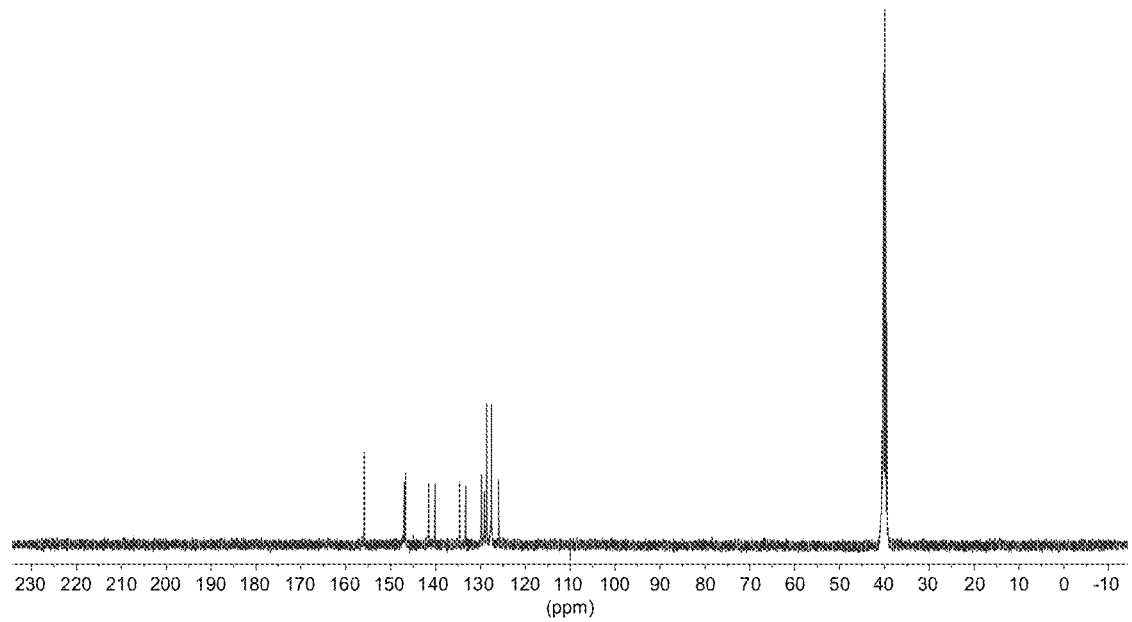
FIG. 62 shows a graph illustrating $^{13}$C NMR spectrum for compound 24a in $(CD_3)_2SO$ (100 MHz).

To a solution of [1,1'-biphenyl]-3,4'-dicarboxaldehyde (105 mg, 0.5 mmol) in 1,4-dioxane (4 mL), aminoguanidine hydrochloride (100 mg, 0.09 mmol) and 1 N HCl (0.40 mL) were added. The reaction mixture was stirred at 90° C. for 2 h and the resulting solution was filtered. The residue obtained was washed with 1,4-dioxane (25 mL) to afford compound 24a (165 mg, 93%) as a white solid: $^1$H NMR (400 MHz, (CD$_3$)$_2$SO, FIG. 61) δ 11.96 (s, 2H), 8.24-8.20 (m, 3H), 8.19 (s, 1H), 7.97-7.93 (m, 3H), 7.84 (dt, J$_1$=7.7 Hz, J$_2$=1.2 Hz, 2H), 7.80 (d, J=8.4 Hz, 4H), 7.79 (dt, J$_1$=7.7 Hz, J$_2$=1.2 Hz, 2H), 7.53 (t, J=7.7 Hz, 1H); $^{13}$C NMR (100 MHz, (CD$_3$)$_2$SO, FIG. 62) δ 155.92, 155.88, 146.9, 146.7, 141.5, 140.1, 134.6, 133.3, 129.8, 129.1, 128.6, 127.7, 127.5, 125.9.

Preparation of Compound 24b

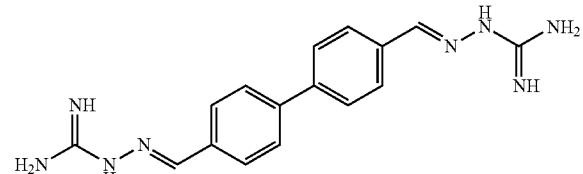

Figure 63:
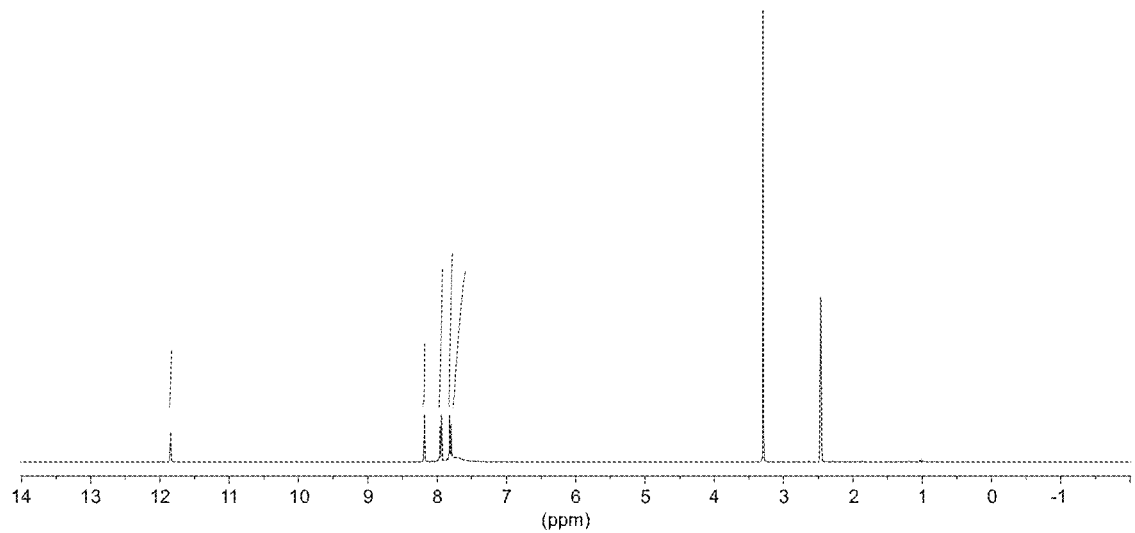
FIG. 63 shows a graph illustrating $^1$H NMR spectrum for compound 24b in $(CD_3)_2SO$ (400 MHz).
Figure 64:
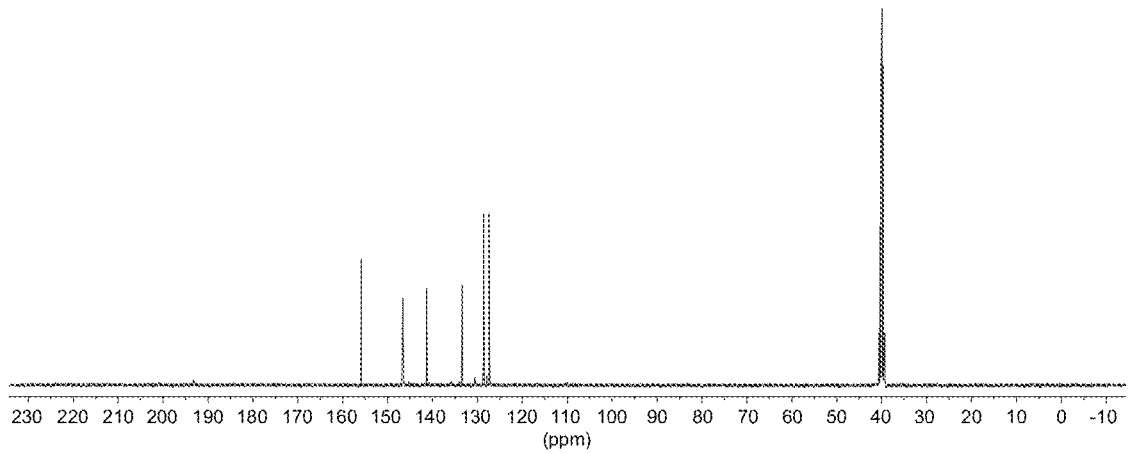
FIG. 64 shows a graph illustrating $^{13}$C NMR spectrum for compound 24b in $(CD_3)_2SO$ (100 MHz).

To a solution of [1,1'-biphenyl]-4,4'-dicarboxaldehyde (200 mg, 0.95 mmol) in EtOH (8 mL), aminoguanidine hydrochloride (263 mg, 2.34 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 24b (212 mg, 69%) as a yellow solid: $^1$H NMR (400 MHz, (CD$_3$)$_2$SO, FIG. 63) δ 11.85 (s, 2H), 8.19 (s, 2H), 7.94 (d, J=8.5 Hz, 4H), 7.80 (d, J=8.5 Hz, 4H), 7.82-7.61 (br s, 6H); $^{13}$C NMR (100 MHz, (CD$_3$)$_2$SO, FIG. 64) δ 155.9, 146.6, 141.3, 133.4, 128.6, 127.4.

Preparation of Compound 24c

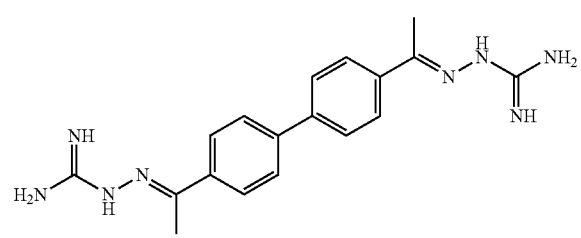 [SMILES: C/C(=N\NC(=N)N)c1ccc(-c2ccc(/C(C)=N/NC(=N)N)cc2)cc1]

Figure 65:
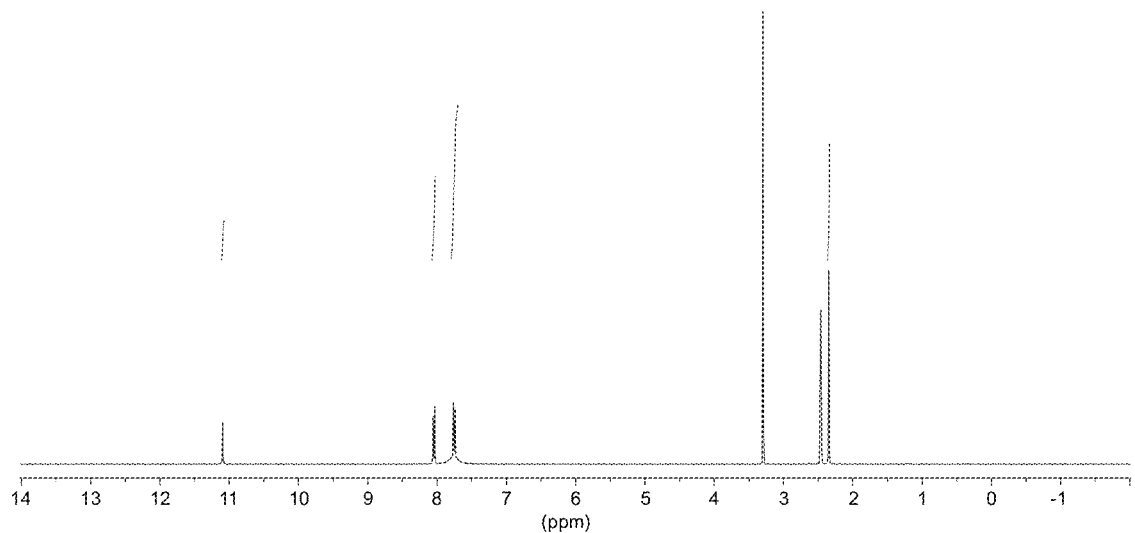
FIG. 65 shows a graph illustrating $^1$H NMR spectrum for compound 24c in $(CD_3)_2SO$ (400 MHz).
Figure 66:
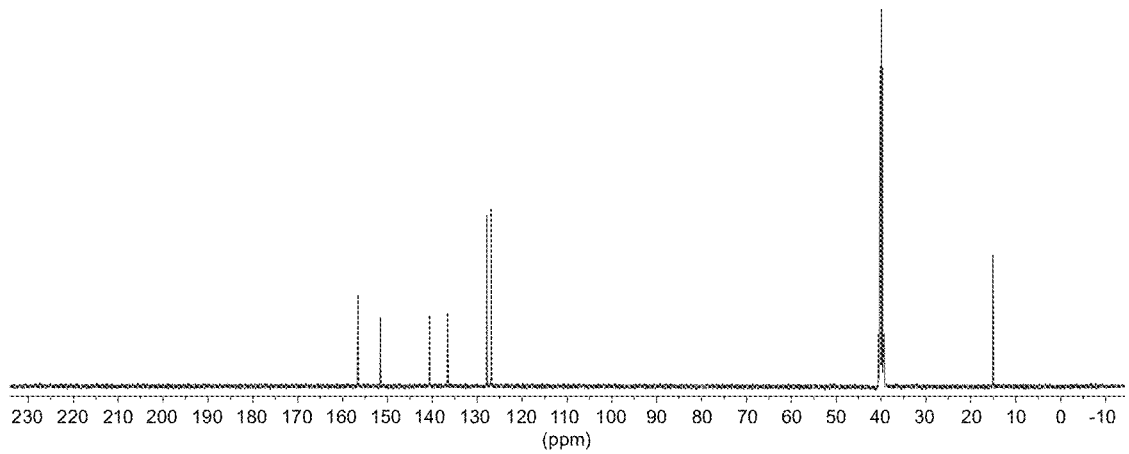
FIG. 66 shows a graph illustrating $^{13}$C NMR spectrum for compound 24c in $(CD_3)_2SO$ (100 MHz).

To a solution of 4,4'-diacetylbiphenyl (150 mg, 0.63 mmol) in EtOH (8 mL), aminoguanidine hydrochloride (173 mg, 1.57 mmol) and a catalytic amount of concentrated HCl (0.04 mL) were added. The reaction mixture was stirred at 80° C. for 30 min and the resulting solution was filtered. The residue obtained was washed with hot EtOH (25 mL) to afford compound 24c (186 mg, 85%) as a white solid: $^1$H NMR (400 MHz, (CD$_3$)$_2$SO, FIG. 65) δ 11.09 (s, 2H), 8.04 (d, J=8.5 Hz, 4H), 7.75 (d, J=8.5 Hz, 4H), 7.81-7.71 (br s, 6H), 2.35 (s, 6H); $^{13}$C NMR (100 MHz, (CD$_3$)$_2$SO, FIG. 66) δ 156.5, 151.5, 140.7, 136.6, 127.8, 126.9, 15.1.

Biological Studies:
Antifungal Agents.

A 5 mg/mL stock solution of compounds 7a-24c was prepared in DMSO and stored at −20 OC in the dark (wrapped in foil). The antifungal agent voriconazole (VOR) was obtained from AK Scientific Inc. (Mountain View, CA, USA). The antifungal agent caspofungin (CAS) was purchased from Sigma-Aldrich (St. Louis, MO, USA). CAS and VOR were dissolved in DMSO at final concentrations of 5 mg/mL and were stored at −20° C.

Organisms and Culture Conditions.

*Candida albicans* ATCC 10231 (A), *C. albicans* ATCC 64124 (B), and *C. albicans* ATCC MYA-2876 (C) were kindly provided by Dr. Jon Y. Takemoto (Utah State University, Logan, UT, USA). *C. albicans* ATCC 90819 (D), *C. albicans* ATCC MYA-2310 (E), *C. albicans* ATCC MYA-1237 (F), *C. albicans* ATCC MYA-1003 (G), *Candida glabrata* ATCC 2001 (H), *Candida krusei* ATCC 6258 (I), *Candida parapsilosis* ATCC 22019 (J), *Aspergillus flavus* ATCC MYA-3631 (K), and *Aspergillus terreus* ATCC MYA-3633 (M) were obtained from the American Type Culture Collection (ATCC; Manassas, VA, USA). *Aspergillus nidulans* ATCC 38163 (L) was received from Dr. Jon S. Thorson (University of Kentucky, Lexington, KY, USA). Filamentous fungi and yeasts were cultivated at 35° C. in RPMI 1640 medium (with 1-glutamine, without sodium biocarbonate, Sigma-Aldrich, St. Louis, MO) buffered to a pH of 7.0 with 0.165 M morpholinepropanesulfonic acid (MOPS) buffer (Sigma-Aldrich).

The human bronchus normal cell line BEAS-2B (ATCC CRL-9609) and the human lung carcinoma cell line A549 (ATCC CRL-185) were kind gifts from the laboratories of Dr. Matthew S. Gentry (University of Kentucky, Lexington, KY, USA) and Dr. David K. Orren (University of Kentucky, Lexington, KY, USA). The mammalian cells were grown in Dulbecco's Modified Eagle's Medium (DMEM) (from ATCC) with 10% fetal bovine serum (FBS) (from ATCC) and 1% Pen/Strep (from ATCC). Cell lines were cultured at 37° C. with 5% $CO_2$ and passaged by trypsinization with 0.05% trypsin:0.53 mM EDTA (from ATCC). Cell confluency was determined by using a Nikon Eclipse TS100 microscope (Minato, Tokyo, Japan).

MIC Value Determination by In Vitro Antifungal Assays.

The MIC values of compounds 7a-24c against yeast cells (strains A-J) were determined in 96-well plates as described in the CLSI document M27-A3 with minor modifications. A single colony of freshly prepared yeast cells was used to inoculate 5 mL of yeast extract peptone dextrose (YPD) broth prior to incubation overnight with shaking at 200 rpm at 35° C. From the actively growing yeast culture, 100 μL were then transferred to 900 μL of sterile dd$H_2O$ and re-adjusted to achieve $OD_{600}$ of 0.12 (~1×$10^6$ CFU/mL). The cell suspension was further diluted to achieve 2-4×$10^3$ CFU/mL in RPMI 1640 medium. 100 μL of cells (to achieve a final concentration of 1-2×$10^3$ CFU/mL) were added to the wells of a 96-well microtiter plates that contained 0.03-31.3 μg/mL of compounds 7a-24c, VOR, or CAS prior to incubation for 48 h at 35° C. The final concentration of DMSO was ensured to be <1.25% in all experiments. The MIC values for compounds 7a-24c and CAS were defined as the minimum drug concentration that yielded complete inhibition (also known as MIC-0). For VOR, the minimum drug concentration that yielded at least 50% growth inhibition (MIC-2) when compared with the growth control well was reported. One exception for the reporting of the MIC of VOR was against C. albicans ATCC 10231 (strain A), where the MIC-0 (indicating complete inhibition) was reported. These data are presented in Table 1.

Similarly, the MIC values of compounds 7a-24c, as well as that of the two control drugs against filamentous fungi (strains K-M) were determined as previously described in CLSI document M38-A2. Spores were harvested from sporulating cultures growing on potato dextrose agar (PDA) by filtration through sterile glass wool and enumerated by using a hemocytometer to obtain the desired inoculum size. Serial dilutions of compounds 7a-24c as well as VOR and CAS were made in sterile 96-well microplates in the range of 0.03-31.3 μg/mL in RPMI 1640 medium. Spore suspensions were added to the wells to afford a final concentration of 5×$10^5$ CFU/mL. The plates were incubated at 35° C. for 48 h. The MIC values of compounds 7a-24c and CAS against filamentous fungi were based on the complete inhibition of growth when compared to the growth control (MIC-0). MIC-2 values are reported for VOR. Each test was performed in triplicate. These data are also presented in Table 1.

Biofilm Disruption Assays.

Figure 67A:
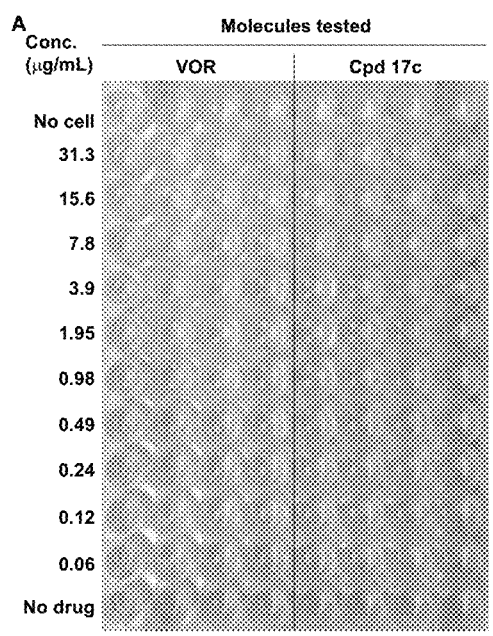
FIGS. 67A-B show images illustrating 96-well plates showing the anti-biofilm activity of VOR and compound 17c (with the corresponding concentrations used displayed on the left of the plate) against (A) *C. albicans* ATCC 10231 (strain A) and (B) *C. albicans* ATCC 64124 (strain B) determined by XTT reduction assay. The negative control (no cell) and the growth control (no drug) are also provided in the top and bottom rows, respectively.
Figure 67B:
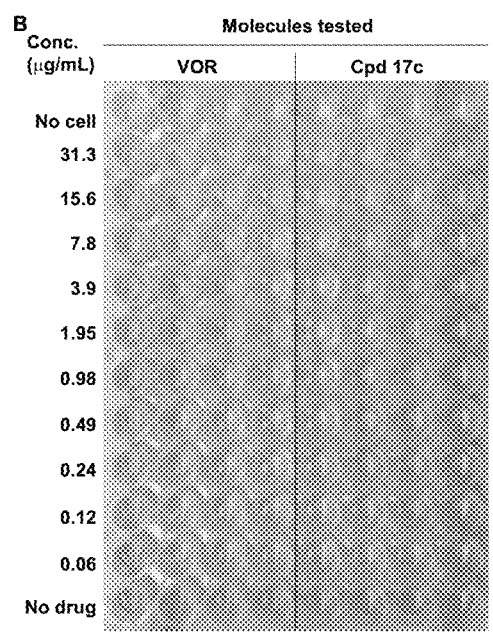

Biofilm disruption assays were performed to assess the effectiveness of compound 17c against sessile yeast cells for two representative yeast strains, C. albicans ATCC 10231 (strain A) and C. albicans ATCC 64124 (strain B). VOR was used as a positive control. Biofilm assays were performed in 96-well plates using XTT [2,3-bis(2-methoxy-4-nitro-5-sulfophenyl)-2H-tetrazolium-5-carboxanilide] to measure the viability of the biofilm as previously described. An overnight culture of the yeast cells was grown at 35° C. in YPD medium with shaking at 200 rpm. The overnight culture was diluted in RPMI 1640 medium to an $OD_{600}$ between 0.12 and 0.15 to make a working stock. The working stock was transferred to 96-well plates in 100 μL aliquots, leaving one column empty for the sterile controls. The plates were incubated at 37° C. for 24 h to allow formation of the biofilm. The medium and planktonic cells from the plate were then aspirated. Phosphate buffered saline (PBS) was then used to wash any remaining planktonic cells off of the biofilm wells. The wells were washed 3 times with PBS. After washing, RPMI 1640 medium and drug were added to the plate, in a similar fashion to that described in the MIC assays. Plates were incubated at 37° C. for 24 h. Finally, the plates were washed 3 times with PBS before adding 100 μL of XTT dye. The XTT was prepared by dissolving XTT at 0.5 mg/mL concentration in sterile PBS. Before adding XTT to the plates, 1 μL of 10 mM menadione in acetone was added to 10 mL of the 0.5 mg/mL solution of XTT. After addition of XTT (containing menadione), the plates were incubated for 3 h at 37° C. in the dark. 80 μL of liquid from each well was transferred to new plates, which were then read for absorbance at 450 nm with a SpectraMax M5 plate reader (Molecular Devices, Sunnyvale, CA, USA). For these experiments, the sessile MIC ($SMIC_{50}$ and $SMIC_{99}$) values, which are defined as the drug concentration required to inhibit the metabolic activity of biofilm by 50% and 99% compared to the growth control (Table 2), were determined. The plates used to determine the $SMIC_{50}$ and $SMIC_{99}$ are provided in FIGS. 67A-B. Each assay was performed in quadruplicate.

In Vitro Cytotoxicity Assays.

Cytotoxicity assays were performed as previously described with slight modifications. A549 and BEAS-2B cells were first thawed from stocks and grown. The confluent cells were transferred to a 96-well microtiter plates at density of 3000 cells/well. The 96-well plates were incubated at 37° C. with 5% $CO_2$ overnight. Fresh powder of compounds 7a,b, 10a, 12a,b, 15a,b, 17a-c, 20a, and 24a were prepared as 31 mg/mL stock solutions in biological DMSO (1000× the highest final concentration). The stock solutions were serially diluted in 1.5 mL eppendorf tubes to achieve concentrations of 31-0.12 mg/mL. 1 μL of these 1000× compound stock solutions was then added to 999 μL of DMEM medium in 1.5 mL eppendorf tubes to obtain final concentrations of 31-0.12 μg/mL. The medium in the 96-well plates containing the cells was aspirated and replaced by DMEM with the appropriate concentrations of compounds 7a,b, 10a, 12a,b, 15a,b, 17a-c, 20a, and 24a. The 96-well plates were further incubated for 24 h at 37° C. with 5% $CO_2$. To evaluate cell survival, each well was treated with 10 μL (25 mg/L) of resazurin sodium salt (Sigma-Aldrich, St. Louis, MO, USA) and incubated for another 6 h. Metabolically active cells can convert resazurin to the highly fluorescent dye, resorufin, and be detected at $A_{560}$ excitation and $A_{590}$ emission using a SpectraMax M5 plate reader (Molecular Devices, San Jose, CA, USA). Triton X-100® (1%, v/v) was used as the positive control, the negative control consisted of cells treated with the delivery vehicle (0.1% DMSO), and the blank control only had media with 0.1% DMSO without cells. The percentage survival rates were calculated by using the following formula: % cell survival=[(fluorescence of sample)−(fluorescence of background)]×100/[(fluorescence of negative control)−(fluorescence of background)]. Experiments were done in duplicate. Please note that FIGS. 3A-B only display data from 31 to 1.9 μg/mL as none of the compounds displayed toxicity from 0.96-0.12 μg/mL.

Hemolytic Activity Assays.

The hemolytic activity of compounds 7a,b, 12a,b, 15a,b, 17a-c, 20a, and 24a was determined by using previously described methods with minor modifications. Murine red blood cells (mRBCs) were prepared by suspending 1 mL of murine blood in 3 mL of PBS prior to centrifugation at 1,000 rpm for 5 min. The mRBCs were washed four times in PBS and resuspended in the same buffer to a final concentration of $10^7$ mRBC/mL. Compounds 7a,b, 12a,b, 15a,b, 17a-c, 20a, and 24a were serially diluted in Eppendorf tubes containing 100 µL of ddH$_2$O, and 100 µL of mRBC suspension was added to achieve a final concentration of compounds ranging from 0.48-62.5 µg/mL and $5 \times 10^6$ mRBC/mL. The tubes were incubated at 37° C. for 60 min. VOR was used as a positive control at concentration ranging from 0.48-62.5 µg/mL. Eppendorf tubes containing 200 µL of ddH$_2$O and 2 µL of 1% v/v Triton™ X-100 served as negative (blank) and positive controls, respectively. The percentage of hemolysis was calculated using the following equation: % hemolysis=[(absorbance of sample)−(absorbance of blank)]×100/(absorbance of positive control).

Time-Kill Assays.

Time-kill assays were used to assess the inhibitory efficiency of compound 17c against two yeast strains, *C. albicans* ATCC 10231 (strain A) and *C. albicans* ATCC 64124 (strain B). The protocol for time-kill assays followed methods previously described with minor modifications. Yeast cultures were grown overnight in YPD medium at 35° C. with shaking at 200 rpm. A working stock of fungal cells was made by diluting cultures in RPMI 1640 medium to an OD$_{600}$ of 0.125 (~$1 \times 10^6$ CFU/mL). From the working stock, 100 µL of cells were added to 4.9 mL of RPMI 1640 medium in sterile culture tubes, making the starting fungal cell concentration ~$1 \times 10^5$ CFU/mL. Compounds were then added to the fungal cells. The treatment conditions included sterile control, growth control, VOR (positive control), compound 17c at 0.5×, 1×, and 2×MIC. For *C. albicans* ATCC 10231 (strain A), the concentration of VOR was 0.98 µg/mL and the concentrations of compound 17c were 0.98 (0.5×MIC), 1.95 (1×MIC), and 3.9 (2×MIC) g/mL. For *C. albicans* ATCC 64124 (strain B), the concentration of VOR was 32 µg/mL and the concentrations of compound 17c were 1.95 (0.5×MIC), 3.9 (1×MIC), and 7.8 (2×MIC) g/mL. The treated fungal cultures were incubated at 35° C. with 200 rpm shaking for 24 h. Samples were aliquoted from the different treatments at regular time points (0, 3, 6, 9, 12, and 24 h) and plated in duplicate. For each time point, cultures were vortexed, 100 µL of culture were aspirated, and 10-fold serial dilutions were made in sterile ddH$_2$O. From the appropriate dilutions, 100 µL of fungal suspension was spread onto PDA plates and incubated at 35° C. for 48 h before colony were counted. At 24 h, 50 µL of 1 mM resazurin in PBS was added to the treatments and incubated at 35° C. with 200 rpm shaking for 2 h in the dark for visual inspection (FIGS. 5A-D). Experiments were performed in duplicate.

hERG Binding Studies.

Materials.

The HEK-293 cell line stably expressing the hERG potassium channel (accession number U04270) referred to as hERG-HEK cells were received at passage 11 from Millipore (CYL3006, lot 2, Billerica, MA). [$^3$H]-Dofetilide (specific activity of 80 Ci/mmol; labeled on the N-methyl group) was obtained from American Radiolabeled Chemicals, St. Louis, MO Other chemicals and solvents were obtained from Sigma-Aldrich (Milwaukee, WI) with exceptions of polyethylenimine (PEI), which was obtained from Fluka/Sigma-Aldrich (St. Louis, MO), and Minimium Essential Medium (MEM) with GlutaMAX™ and phenol red, MEM non-essential amino acids solution (NEAA, 100×), G418 disulfate salt solution, fetal bovine serum (FBS), 0.05% Trypsin-EDTA 1× with phenol red, and Hank's balanced salt solution (HBSS), which were obtained from Life Technologies (Carlsbad, CA).

hERG-HEK Cell Culture.

The hERG-HEK cells were cultured according to the protocol provided by Millipore. Cells were maintained in MEM (with GlutaMAX™ and phenol red) supplemented with 10% FBS, 1% NEAA and 400 µg/mL G418 disulfate salt, and incubated at 37° C. in a humidified atmosphere with 5% CO$_2$. Frozen aliquots of cells were transferred into T-75 cm$^2$ flasks and allowed to adhere for 4-8 h. The medium was replaced every 2 days. Passages were carried out at least 3 times after thawing at 6-day intervals. Cells were dissociated with trypsin/EDTA and seeded into new 150×25 mm dishes at $2-3 \times 10^6$ cells per dish and placed at 30° C., 5% CO$_2$, for 40-48 h prior to membrane preparation. Membrane preparation occurred 6 days after the last passage (passage 20).

Membrane Preparation.

Cell membrane preparation was based on previous methods. Cells were rinsed twice with HBSS at 37° C. and collected by scraping the dishes in ~20 mL of ice-cold 0.32 M sucrose and homogenized on ice with a Teflon pestle using a Maximal Digital homogenizer (Fisher Scientific, Pittsburgh, PA) at ~280 rpm for 30 sec. Homogenates were centrifuged at 300 g and 800 g for 4 min each at 4° C. Pellets were resuspended in 9 mL of ice-cold Milli-Q H$_2$O and osmolarity restored by addition of 1 mL of 500 mM Tris buffer (pH 7.4) followed by suspension and centrifugation at 20,000 g for 30 min at 4° C. Pellets were homogenized in 2 mL assay buffer (50 mM Tris, 10 mM KCl, and 1 mM MgCl$_2$, 4° C.) and aliquots of cell membrane suspensions were stored at −80° C. and thawed the day of the [$^3$H]-dofetilide binding assay. Protein content was determined prior to the assay using a Bradford protein assay with bovine albumin as the standard.

[$^3$H]-Dofetilide Binding Assay.

[$^3$H]-Dofetilide binding assays using hERG-HEK293 cell membranes were based on previous methods. Assays determining concentration-response were conducted in duplicate, and three independent assays were performed for each analogue evaluated. Cell membrane suspension (5 µg) was added to duplicate tubes containing assay buffer, 25 µL of a single concentration of N,N-dialkylaminostilbene agent (FIDAS agent) (concentration range of 10 nM-100 µM for each experiment), and 25 µL of [$^3$H]-dofetilide (5 nM, final concentration) for an assay volume of 250 µL. Binding occurred for 60 min at 25° C. and was terminated by rapid filtration through Whatman GF/B filters, which were pre-soaked in 0.25% PEI overnight, using a Brandel cell/membrane harvester (M-48; Brandel Inc., Gaithersburg, MD). Filters were washed three times with ~1 mL of ice-cold assay buffer. Radioactivity was determined by liquid scintillation spectrometry using the Tri-Carb 2100-TR Liquid Scintillation Analyzer (Perkin-Elmer Life and Analytical Sciences).

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

[1] Hahn, T., McCarthy, P. L., Jr., Hassebroek, A., Bredeson, C., Gajewski, J. L., Hale, G. A., Isola, L. M., Lazarus, H. M., Lee, S. J., Lemaistre, C. F., Loberiza, F., Maziarz, R. T., Rizzo, J. D., Joffe, S., Parsons, S., and Majhail, N. S. (2013) Significant improvement in survival after allogeneic hematopoietic cell transplantation during a period of significantly increased use, older recipient age, and use of unrelated donors, *J. Clin. Oncol.* 31, 2437-2449.

[2] Van Thiel, D. H., George, M., and Moore, C. M. (2012) Fungal infections: their diagnosis and treatment in transplant recipients, *Int. J. Hepatol.* 2012, 106923.

[3] Eggimann, P., Que, Y. A., Revelly, J. P., and Pagani, J. L. (2015) Preventing invasive *Candida* infections. Where could we do better?, *J. Hosp. Infect.* 89, 302-308.

[4] Mavor, A. L., Thewes, S., and Hube, B. (2005) Systemic fungal infections caused by *Candida* species: epidemiology, infection process and virulence attributes, *Curr. Drug Targets* 6, 863874.

[5] Girishkumar, H., Yousuf, A. M., Chivate, J., and Geisler, E. (1999) Experience with invasive *Candida* infections, *Postgrad. Med. J.* 75, 151-153.

[6] Nolla-Salas, J., Sitges-Serra, A., Leon-Gil, C., Martinez-Gonzalez, J., Leon-Regidor, M. A., Ibanez-Lucia, P., and Torres-Rodriguez, J. M. (1997) Candidemia in non-neutropenic critically ill patients: analysis of prognostic factors and assessment of systemic antifungal therapy. Study Group of Fungal Infection in the ICU, *Intensive Care Med.* 23, 23-30.

[7] Leon, C., Ostrosky-Zeichner, L., and Schuster, M. (2014) What's new in the clinical and diagnostic management of invasive candidiasis in critically ill patients, *Intensive Care Med.* 40, 808-819.

[8] Denning, D. W. (1996) Therapeutic outcome in invasive aspergillosis, *Clin. Infect. Dis.* 23, 608-615.

[9] Denning, D. W., and Stevens, D. A. (1990) Antifungal and surgical treatment of invasive aspergillosis: review of 2,121 published cases, *Rev. Infect. Dis.* 12, 1147-1201.

[10] Mousavi, S. A., and Robson, G. D. (2003) Entry into the stationary phase is associated with a rapid loss of viability and an apoptotic-like phenotype in the opportunistic pathogen *Aspergillus fumigatus*, *Fungal Genet. Biol.* 39, 221-229.

[11] Rautemaa-Richardson, R., and Richardson, M. D. (2017) Systemic fungal infections, *Medicine* 45, 757-762.

[12] Dodds Ashley, E. S., Lewis, R., Lewis, J. S., Martin, C., and Andes, D. (2006) Pharmacology of systemic antifungal agents, *Clin. Infect. Dis.* 43, S28-S39.

[13] Perlin, D. S., Rautemaa-Richardson, R., and Alastruey-Izquierdo, A. (2017) The global problem of antifungal resistance: prevalence, mechanisms, and management, *Lancet Infect. Dis.* 17, e383-e392.

[14] Thamban Chandrika, N., and Garneau-Tsodikova, S. (2018) Comprehensive review of chemical strategies for the preparation of new aminoglycosides and their biological activities, *Chem. Soc. Rev.* 47, 1189-1249.

[15] Ngo, H. X., Garneau-Tsodikova, S., and Green, K. D. (2016) A complex game of hide and seek: the search for new antifungals, *Med Chem Comm* 7, 1285-1306.

[16] Chandrika, N. T., and Garneau-Tsodikova, S. (2016) A review of patents (2011-2015) towards combating resistance to and toxicity of aminoglycosides, *Med Chem Comm* 7, 50-68.

[17] Fosso, M. Y., Li, Y., and Garneau-Tsodikova, S. (2014) New trends in aminoglycosides use, *Med Chem Comm* 5, 1075-1091.

[18] Fosso, M. Y., Shrestha, S. K., Green, K. D., and Garneau-Tsodikova, S. (2015) Synthesis and bioactivities of kanamycin B-derived cationic amphiphiles, *J. Med. Chem.* 58, 9124-9132.

[19] Shrestha, S. K., Fosso, M. Y., and Garneau-Tsodikova, S. (2015) A combination approach to treating fungal infections, *Sci. Rep.* 5, 17070.

[20] Shrestha, S. K., Fosso, M. Y., Green, K. D., and Garneau-Tsodikova, S. (2015) Amphiphilic tobramycin analogues as antibacterial and antifungal agents, *Antimicrob. Agents Chemother.* 59, 4861-4869.

[21] Thamban Chandrika, N., Shrestha, S. K., Ranjan, N., Sharma, A., Arya, D. P., and Garneau-Tsodikova, S. (2018) New application of neomycin B-bisbenzimidazole hybrids as antifungal agents, *ACS Infect. Dis.* 4, 196-207.

[22] Shrestha, S. K., Grilley, M., Anderson, T., Dhiman, C., Oblad, J., Chang, C. W., Sorensen, K. N., and Takemoto, J. Y. (2015) In vitro antifungal synergy between amphiphilic aminoglycoside $K_2O$ and azoles against *Candida* species and *Cryptococcus neoformans*, *Med. Mycol.* 53, 837-844.

[23] Benhamou, R. I., Steinbuch, K. B., and Fridman, M. (2016) Antifungal imidazole-decorated cationic amphiphiles with markedly low hemolytic activity, *Chem. Eur. J.* 22, 1148-1151.

[24] Shrestha, S. K., Chang, C. W., Meissner, N., Oblad, J., Shrestha, J. P., Sorensen, K. N., Grilley, M. M., and Takemoto, J. Y. (2014) Antifungal amphiphilic aminoglycoside $K_{20}$: bioactivities and mechanism of action, *Front. Microbiol.* 5, 671.

[25] Shrestha, S., Grilley, M., Fosso, M. Y., Chang, C. W., and Takemoto, J. Y. (2013) Membrane lipid-modulated mechanism of action and non-cytotoxicity of novel fungicide aminoglycoside FG08, *PLoS One* 8, e73843.

[26] Fosso, M., AlFindee, M. N., Zhang, Q., Nziko Vde, P., Kawasaki, Y., Shrestha, S. K., Bearss, J., Gregory, R., Takemoto, J. Y., and Chang, C. W. (2015) Structure-activity relationships for antibacterial to antifungal conversion of kanamycin to amphiphilic analogues, *J. Org. Chem.* 80, 4398-4411.

[27] Thamban Chandrika, N., Shrestha, S. K., Ngo, H. X., and Garneau-Tsodikova, S. (2016) Synthesis and investigation of novel benzimidazole derivatives as antifungal agents, *Bioorg. Med. Chem.* 24, 3680-3686.

[28] Keller, P., Muller, C., Engelhardt, I., Hiller, E., Lemuth, K., Eickhoff, H., Wiesmuller, K. H., Burger-Kentischer, A., Bracher, F., and Rupp, S. (2015) An antifungal benzimidazole derivative inhibits ergosterol biosynthesis and reveals novel sterols, *Antimicrob. Agents Chemother.* 59, 6296-6307.

[29] Shrestha, S. K., Garzan, A., and Garneau-Tsodikova, S. (2017) Novel alkylated azoles as potent antifungals, *Eur. J Med. Chem.* 133, 309-318.

[30] Thamban Chandrika, N., Shrestha, S. K., Ngo, H. X., Tsodikov, O. V., Howard, K. C., and Garneau-Tsodikova, S. (2018) Alkylated piperazines and piperazine-azole hybrids as antifungal agents, *J. Med. Chem.* 61, 158-173.

[31] Thamban Chandrika, N., Shrestha, S. K., Ngo, H. X., Howard, K. C., and Garneau-Tsodikova, S. (2018) Novel fluconazole derivatives with promising antifungal activity, *Bioorg. Med. Chem.* 26, 573-580.

[32] Allen, D., Wilson, D., Drew, R., and Perfect, J. (2015) Azole antifungals: 35 years of invasive fungal infection management, *Expert Rev. Anti Infect. Ther.* 13, 787-798.

[33] Bendaha, H., Yu, L., Touzani, R., Souane, R., Giaever, G., Nislow, C., Boone, C., El Kadiri, S., Brown, G. W., and Bellaoui, M. (2011) New azole antifungal agents with novel modes of action: synthesis and biological studies of new tridentate ligands based on pyrazole and triazole, *Eur. J. Med. Chem.* 46, 4117-4124.

[34] Fakhim, H., Emami, S., Vaezi, A., Hashemi, S. M., Faeli, L., Diba, K., Dannaoui, E., and Badali, H. (2017) In vitro activities of novel azole compounds ATTAF-1 and ATTAF-2 against fluconazole-susceptible and -resistant isolates of *Candida* species, *Antimicrob. Agents Chemother.* 61, e01106-01116.

[35] Holbrook, S. Y. L., Garzan, A., Dennis, E. K., Shrestha, S. K., and Garneau-Tsodikova, S. (2017) Repurposing antipsychotic drugs into antifungal agents: Synergistic combinations of azoles and bromperidol derivatives in the treatment of various fungal infections, *Eur. J. Med. Chem.* 139, 12-21.

[36] Ngo, H. X., Shrestha, S. K., and Garneau-Tsodikova, S. (2016) Identification of ebsulfur analogues with broad-spectrum antifungal activity, *Chem Med Chem* 11, 1507-1516.

[37] Thangamani, S., Eldesouky, H. E., Mohammad, H., Pascuzzi, P. E., Avramova, L., Hazbun, T. R., and Seleem, M. N. (2017) Ebselen exerts antifungal activity by regulating glutathione (GSH) and reactive oxygen species (ROS) production in fungal cells, *Biochim. Biophys. Acta* 1861, 3002-3010.

[38] Venturini, T. P., Chassot, F., Loreto, E. S., Keller, J. T., Azevedo, M. I., Zeni, G., Santurio, J. M., and Alves, S. H. (2016) Antifungal activities of diphenyl diselenide and ebselen alone and in combination with antifungal agents against *Fusarium* spp, *Med. Mycol.* 54, 550-555.

[39] Shrestha, S. K., Kril, L. M., Green, K. D., Kwiatkowski, S., Sviripa, V. M., Nickell, J. R., Dwoskin, L. P., Watt, D. S., and Garneau-Tsodikova, S. (2017) Bis(N-amidinohydrazones) and N-(amidino)-N-aryl-bishydrazones: New classes of antibacterial/antifungal agents, *Bioorg. Med. Chem.* 25, 58-66.

[40] Kumar, D. E. P. (2010) *Principles and practice of clinical cardiovascular genetics*, Oxford University Press, New York.

[41] Trabelsi, M., Salem, M., and Champagne, B. (2003) Investigation of the configuration of alkyl phenyl ketone phenylhydrazones from ab initio 1H NMR chemical shifts, *Org. Biomol. Chem.* 1, 3839-3844.

[42] Bellamy, A. J., and Hunter, J. (1976) EZ-isomerism in alkyl phenyl ketone phenylhydrazones and acetaldehyde phenylhydrazone, *J. Chem. Soc., Perkin Trans.* 1 4, 456-458.

[43] Balkovec, J. M., Bouffard, F. A., and Black, R. M. (1995) AZA cyclohexapeptide compounds, (Patent, U., Ed.), USA.

[44] Donnelly, J. P., and De Pauw, B. E. (2004) Voriconazole—a new therapeutic agent with an extended spectrum of antifungal activity, *Clin. Microbiol. Infect.* 10 Suppl 1, 107-117.

[45] Ramage, G., Rajendran, R., Sherry, L., and Williams, C. (2012) Fungal biofilm resistance, *Int. J. Microbiol.* 2012, 528521.

[46] Borghi, E., Morace, G., Borgo, F., Rajendran, R., Sherry, L., Nile, C., and Ramage, G. (2015) New strategic insights into managing fungal biofilms, *Front. Microbiol.* 6, 1077.

[47] Fanning, S., and Mitchell, A. P. (2012) Fungal biofilms, *PLoS Pathog.* 8, e1002585.

[48] Nett, J. E., Cain, M. T., Crawford, K., and Andes, D. R. (2011) Optimizing a *Candida* biofilm microtiter plate model for measurement of antifungal susceptibility by tetrazolium salt assay, *J. Clin. Microbiol.* 49, 1426-1433.

[49] Pierce, C. G., Uppuluri, P., Tristan, A. R., Wormley, F. L., Jr., Mowat, E., Ramage, G., and Lopez-Ribot, J. L. (2008) A simple and reproducible 96-well plate-based method for the formation of fungal biofilms and its application to antifungal susceptibility testing, *Nat. Protoc.* 3, 1494-1500.

[50] Klepser, M. E., Malone, D., Lewis, R. E., Ernst, E. J., and Pfaller, M. A. (2000) Evaluation of voriconazole pharmacodynamics using time-kill methodology, *Antimicrob. Agents Chemother.* 44, 1917-1920.

[51] Teschemacher, A. G., Seward, E. P., Hancox, J. C., and Witchel, H. J. (1999) Inhibition of the current of heterologously expressed HERG potassium channels by imipramine and amitriptyline, *Br. J. Pharmacol.* 128, 479-485.

[52] Clinical and Laboratory Standards Institute. (2008) *Reference method for broth dilution antifungal susceptibility testing of yeasts-Approved standard. CLSI document M27-A3*. Wayne, PA

[53] Clinical and Laboratory Standards Institute. (2008) *Reference method for broth dilution antifungal susceptibility testing of filamentous fungi-$2^{nd}$ Edition: CLSI document M38-A2*. Wayne, PA

[54] Pierce, C. G., Uppuluri, P., Tristan, A. R., Wormley, F. L., Jr., Mowat, E., Ramage, G., and Lopez-Ribot, J. L. (2008) A simple and reproducible 96-well plate-based method for the formation of fungal biofilms and its application to antifungal susceptibility testing, *Nat. Protoc.* 3, 1494-1500.

[55] Shrestha, S. K., Fosso, M. Y., Green, K. D., and Garneau-Tsodikova, S. (2015) Amphiphilic tobramycin analogues as antibacterial and antifungal agents, *Antimicrob. Agents Chemother.* 59, 4861-4869.

[56] Fosso, M. Y., Shrestha, S. K., Green, K. D., and Garneau-Tsodikova, S. (2015) Synthesis and bioactivities of kanamycin B-derived cationic amphiphiles, *J. Med. Chem.* 58, 9124-9132.

[57] Klepser, M. E., Malone, D., Lewis, R. E., Ernst, E. J., and Pfaller, M. A. (2000) Evaluation of voriconazole pharmacodynamics using time-kill methodology, *Antimicrob. Agents Chemother.* 44, 1917-1920.

[58] Shrestha, S. K., Fosso, M. Y., and Garneau-Tsodikova, S. (2015) A combination approach to treating fungal infections, *Sci. Rep.* 5, 17070.

[59] Holbrook, S. Y. L., Garzan, A., Dennis, E. K., Shrestha, S. K., and Garneau-Tsodikova, S. (2017) Repurposing antipsychotic drugs into antifungal agents: Synergistic combinations of azoles and bromperidol derivatives in the treatment of various fungal infections, *Eur. J. Med. Chem.* 139, 12-21.

[60] Biswas, T., Resto-Roldan, E., Sawyer, S. K., Artsimovitch, I., and Tsodikov, O. V. (2013) A novel non-radioactive primase-pyrophosphatase activity assay and its application to the discovery of inhibitors of *Mycobacterium tuberculosis* primase DnaG, *Nucl. Acids Res.* 41, e56.

[61] Jo, S. H., Youm, J. B., Lee, C. O., Earm, Y. E., and Ho, W. K. (2000) Blockade of the HERG human cardiac K(+) channel by the antidepressant drug amitriptyline, *Br. J. Pharmacol.* 129, 1474-1480.

[62] Chen, T. (2010) *A practical guide to assay development and high-throughput screening in drug discovery*, CRC Press Taylor and Francis Group, Boca Raton, FL

[63] Clinical and Laboratory Standards Institute. (2008) *Reference method for broth dilution antifungal susceptibility testing of yeasts-Approved standard. CLSI document M27-A3*. Wayne, PA

[64] Clinical and Laboratory Standards Institute. (2008) *Reference method for broth dilution antifungal susceptibility testing of filamentous fungi-2<sup>nd</sup> Edition: CLSI document M38-A2.* Wayne, PA

[65] Pierce, C. G., Uppuluri, P., Tristan, A. R., Wormley, F. L., Jr., Mowat, E., Ramage, G., and Lopez-Ribot, J. L. (2008) A simple and reproducible 96-well plate-based method for the formation of fungal biofilms and its application to antifungal susceptibility testing, *Nat. Protoc.* 3, 1494-1500.

[66] Shrestha, S. K., Fosso, M. Y., Green, K. D., and Garneau-Tsodikova, S. (2015) Amphiphilic tobramycin analogues as antibacterial and antifungal agents, *Antimicrob. Agents Chemother.* 59, 4861-4869.

[67] Fosso, M. Y., Shrestha, S. K., Green, K. D., and Garneau-Tsodikova, S. (2015) Synthesis and bioactivities of kanamycin B-derived cationic amphiphiles, *J. Med. Chem.* 58, 9124-9132.

[68] Klepser, M. E., Malone, D., Lewis, R. E., Ernst, E. J., and Pfaller, M. A. (2000) Evaluation of voriconazole pharmacodynamics using time-kill methodology, *Antimicrob. Agents Chemother.* 44, 1917-1920.

[69] Shrestha, S. K., Fosso, M. Y., and Garneau-Tsodikova, S. (2015) A combination approach to treating fungal infections, *Sci. Rep.* 5, 17070.

[70] Holbrook, S. Y. L., Garzan, A., Dennis, E. K., Shrestha, S. K., and Garneau-Tsodikova, S. (2017) Repurposing antipsychotic drugs into antifungal agents: Synergistic combinations of azoles and bromperidol derivatives in the treatment of various fungal infections, *Eur. J. Med. Chem.* 139, 12-21.

[71] Biswas, T., Resto-Roldan, E., Sawyer, S. K., Artsimovitch, I., and Tsodikov, O. V. (2013) A novel non-radioactive primase-pyrophosphatase activity assay and its application to the discovery of inhibitors of *Mycobacterium tuberculosis* primase DnaG, *Nucl. Acids Res.* 41, e56.

[72] Jo, S. H., Youm, J. B., Lee, C. O., Earm, Y. E., and Ho, W. K. (2000) Blockade of the HERG human cardiac K(+) channel by the antidepressant drug amitriptyline, *Br. J. Pharmacol.* 129, 1474-1480.

[73] Chen, T. (2010) *A practical guide to assay development and high-throughput screening in drug discovery*, CRC Press Taylor and Francis Group, Boca Raton, FL.

It will be understood that various details of the presently disclosed subject matter can be changed without departing from the scope of the subject matter disclosed herein. Furthermore, the foregoing description is for the purpose of illustration only, and not for the purpose of limitation.

Finally, for further explanation of the features, benefits and advantages of the present invention, attached hereto is Appendix A, which is incorporated herein by this reference, as are all cited references in Appendix A.

What is claimed is:

1. An antifungal composition comprising a compound according to Formula (I):

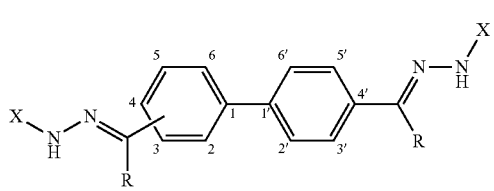

or a pharmaceutically acceptable salt thereof;
wherein each R is independently selected from the group consisting of H and a lower alkyl; and
wherein each X is independently selected from the group consisting of phenyl, a substituted phenyl, an aromatic heterocycle, and a substituted aromatic heterocycle, so long as when both R are H or methyl then at least one X is not phenyl or meta-methoxy substituted phenyl;
wherein the substituted phenyl comprises a substitution selected from the group consisting of nitro, an alkyl, an alkoxy, a halogen, cyano, a carboxylic acid, a sulfonic acid, aryl sulfoxides, aryl sulfones, a trihalomethyl, and combinations thereof; and
aromatic heterocycle or the substituted aromatic heterocycle comprises one or more heteroatoms selected from the group consisting nitrogen, oxygen, sulfur, and combinations thereof, wherein the aryl sulfoxides include $S(=O)C_6H_4Z$, with Z being selected from the group consisting of alkyl, alkoxy, and halogen.

2. An antifungal composition comprising a compound according to Formula (I):

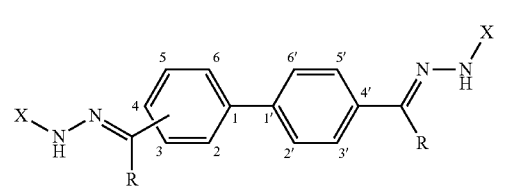

or a pharmaceutically acceptable salt thereof;
wherein each R is independently selected from the group consisting of H and a lower alkyl; and
wherein each X is independently selected from the group consisting of phenyl, a substituted phenyl, an aromatic heterocycle, and a substituted aromatic heterocycle, so long as when both R are H or methyl then at least one X is not phenyl or meta-methoxy substituted phenyl;
wherein the substituted phenyl comprises a substitution selected from the group consisting of nitro, an alkyl, an alkoxy, a halogen, cyano, a carboxylic acid, a sulfonic acid, aryl sulfoxides, aryl sulfones, a trihalomethyl, and combinations thereof; and
aromatic heterocycle or the substituted aromatic heterocycle comprises one or more heteroatoms selected from the group consisting nitrogen, oxygen, sulfur, and combinations thereof, wherein the aryl sulfones include $S(=O)_2C_6H_4Z$, with Z being selected from the group consisting of alkyl, alkoxy, and halogen.

3. An antifungal composition comprising a compound according to Formula (I):

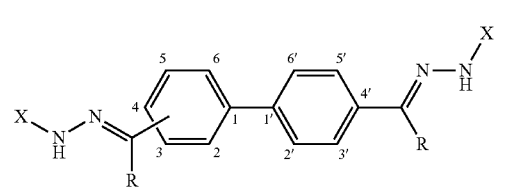

or a pharmaceutically acceptable salt thereof;
wherein each R is independently selected from the group consisting of H and a lower alkyl; and wherein each X is independently selected from the group consisting of phenyl, a substituted phenyl, an aromatic heterocycle, and a substituted aromatic heterocycle, so long as when both R are H or methyl then at least one X is not phenyl or meta-methoxy substituted phenyl;

wherein the substituted phenyl comprises a substitution selected from the group consisting of nitro, an alkyl, an alkoxy, a halogen, cyano, a carboxylic acid, a sulfonic acid, aryl sulfoxides, aryl sulfones, a trihalomethyl, and combinations thereof; and aromatic heterocycle or the substituted aromatic heterocycle comprises one or more heteroatoms selected from the group consisting nitrogen, oxygen, sulfur, and combinations thereof, wherein the substituent of the first ring according to Formula I is in the 3 position.

4. An antifungal composition comprising a compound according to Formula (I):

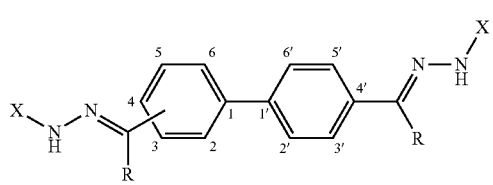

or a pharmaceutically acceptable salt thereof;

wherein each R is independently selected from the group consisting of H and a lower alkyl; and wherein each X is independently selected from the group consisting of phenyl, a substituted phenyl, an aromatic heterocycle, and a substituted aromatic heterocycle, so long as when both R are H or methyl then at least one X is not phenyl or meta-methoxy substituted phenyl;

wherein the substituted phenyl comprises a substitution selected from the group consisting of nitro, an alkyl, an alkoxy, a halogen, cyano, a carboxylic acid, a sulfonic acid, aryl sulfoxides, aryl sulfones, a trihalomethyl, and combinations thereof; and aromatic heterocycle or the substituted aromatic heterocycle comprises one or more heteroatoms selected from the group consisting nitrogen, oxygen, sulfur, and combinations thereof, wherein the substituent of the first ring according to Formula I is in the 4 position.

5. The composition of claim 4, wherein the R in the substituent of the first ring is methyl.

6. An antifungal composition comprising a compound according to Formula (I):

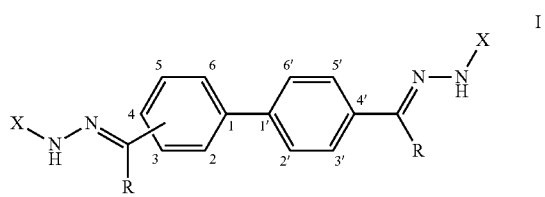

or a pharmaceutically acceptable salt thereof;

wherein each R is independently selected from the group consisting of H and a lower alkyl;

wherein X is a substituted phenyl and the substituted phenyl comprises a substitution selected from the group consisting of nitro, an alkyl, an alkoxy, a halogen, cyano, a carboxylic acid, a sulfonic acid, aryl sulfoxides, aryl sulfones, a trihalomethyl, and combinations thereof, wherein the substituted phenyl includes more than one substitution.

7. The composition of claim 6, wherein the substituted phenyl is disubstituted.

8. The composition of claim 7, wherein the disubstituted phenyl is halogen substituted.

* * * * *